(12) United States Patent
Takami et al.

(10) Patent No.: US 7,693,664 B2
(45) Date of Patent: Apr. 6, 2010

(54) METHOD AND COMPUTER PROGRAM PRODUCT FOR DETERMINING WHETHER OR NOT A TEST PROTEIN HAS THERMOSTABILITY

(75) Inventors: Hideto Takami, Kanagawa (JP); Koki Horikoshi, Kanagawa (JP); Yoshihiro Takaki, Kanagawa (JP); Gab-Joo Chee, Kanagawa (JP); Shinro Nishi, Kanagawa (JP); Shigeru Shimamura, Kanagawa (JP); Hiroko Suzuki, Kanagawa (JP); Ikuo Uchiyama, Aichi (JP); Zhijun Li, Kanagawa (JP)

(73) Assignee: Japan Agency for Marine-Earth Science and Technology, Yokosuka-shi (JP)

( * ) Notice: Subject to any disclaimer, the term of this patent is extended or adjusted under 35 U.S.C. 154(b) by 438 days.

(21) Appl. No.: 11/062,833

(22) Filed: Feb. 23, 2005

(65) Prior Publication Data

US 2005/0202409 A1 Sep. 15, 2005

(30) Foreign Application Priority Data

Feb. 23, 2004 (JP) ............................. 2004-046880
Mar. 8, 2004 (JP) ............................. 2004-064360

(51) Int. Cl.
*G01N 33/48* (2006.01)
(52) U.S. Cl. ............................... 702/19; 703/2; 703/11; 706/45; 707/6; 211/41.12
(58) Field of Classification Search ............. None
See application file for complete search history.

(56) References Cited

U.S. PATENT DOCUMENTS

2006/0142950 A1 * 6/2006 Selifonov et al. ............. 702/20

FOREIGN PATENT DOCUMENTS

JP 2003-250544 A 9/2003

OTHER PUBLICATIONS

Office Action issued in Japanese patent application No. 2005-032296 dated Oct. 20, 2009.
David P. Kreil et al., "Identification of thermophilic species by the amino acid compositions deduced from their genomes", Nucleic Acids Research, 2001, vol. 29, No. 7, pp. 1608-1615.

* cited by examiner

*Primary Examiner*—Carolyn Smith
(74) *Attorney, Agent, or Firm*—Westerman, Hattori, Daniels & Adrian, LLP

(57) ABSTRACT

The invention relates to a method of judging the thermostability of a protein, comprising the steps of calculating an analytical value specific to a test protein by a principal component analysis based on the amino acid composition of the protein calculated from the data of the amino acid sequence of the protein or the nucleotide sequence of the gene and comparing the analytical value with an analytical value of a protein which is retained by a thermostable organism and corresponds to the test protein, and further relates to a program for allowing a computer to execute processing for judging the thermostability of a protein by the method, and a computer readable recording medium having recorded the program thereon.

18 Claims, 24 Drawing Sheets

Fig. 10 A

Table 1. Prediction of thermostability of proteins possessing one-to-one correspondence among the 5 species of *Bacillus*

| GK | category | Annotation | GK PC2 | BC | BC PC2 | BH | BH PC2 | BS | BS PC2 | OI | OI PC2 |
|---|---|---|---|---|---|---|---|---|---|---|---|
| GK0001 | 3.1 | chromosomal replication initiator protein | 0.0007 | BC0001 | -0.0040 | BH0001 | -0.0030 | DNAA | -0.0030 | OB0001 | 0.0032 |
| GK0002 | 3.1 | DNA-directed DNA polymerase III (EC 2.7.7.7) beta subunit | 0.0018 | BC0002 | 0.0195 | BH0002 | 0.0157 | DNAN | 0.0072 | OB0002 | 0.0124 |
| GK0003 | 5 | unknown conserved protein | 0.0511 | BC0003 | 0.0283 | BH0003 | 0.0240 | YAAA | 0.0333 | OB0003 | 0.0333 |
| GK0004 | 3.3 | DNA replication and repair protein | -0.0004 | BC0004 | -0.0047 | BH0004 | -0.0066 | RECF | -0.0161 | OB0004 | -0.0095 |
| GK0005 | 3.4 | DNA gyrase subunit B | 0.0268 | BC0005 | 0.0275 | BH0006 | 0.0283 | GYRB | 0.0236 | OB0006 | 0.0233 |
| GK0006 | 3.4 | DNA gyrase subunit A | 0.0323 | BC0006 | 0.0260 | BH0007 | 0.0335 | GYRA | 0.0356 | OB0007 | 0.0378 |
| GK0008 | 5 | unknown conserved protein | -0.0209 | BC0012 | -0.0437 | BH0019 | -0.0102 | YAAC | -0.0133 | OB0009 | -0.0151 |
| GK0009 | 2.3 | inositol-monophosphate dehydrogenase (EC 1.1.1.205) | 0.0367 | BC0013 | 0.0302 | BH0020 | 0.0375 | GUAB | 0.0351 | OB0010 | 0.0233 |
| GK0011 | 4.2 | superoxide-inducible protein (protein required for pyridoxine synthesis) | 0.0628 | BC0015 | 0.0583 | BH0022 | 0.0564 | YAAD | 0.0507 | OB2687 | 0.0443 |
| GK0012 | 2.2 | 2-deoxy-scyllo-inosose synthase 20kDa subunit | 0.0343 | BC0016 | 0.0609 | BH0023 | 0.0362 | YAAE | 0.0299 | OB2686 | 0.0021 |
| GK0013 | 3.7.2 | seryl-tRNA synthetase (EC 6.1.1.11) | 0.0277 | BC0017 | 0.0440 | BH0024 | 0.0321 | SERS | 0.0449 | OB0012 | 0.0362 |
| GK0014 | 1.8 | spore peptidoglycan hydrolase (N-acetylglucosaminidase) | 0.0026 | BC3607 | -0.0242 | BH2292 | 0.0236 | YAAH | -0.0269 | OB0024 | -0.0286 |
| GK0016 | 5 | unknown conserved protein | 0.0262 | BC0023 | 0.0397 | BH0033 | 0.0315 | YAAJ | 0.0592 | OB0026 | 0.0161 |
| GK0017 | 3.1 | DNA-directed DNA polymerase III (EC 2.7.7.7) gamma and tau subunits | 0.0070 | BC0024 | 0.0216 | BH0034 | -0.0054 | DNAX | 0.0072 | OB0029 | -0.0114 |
| GK0018 | 5 | unknown conserved protein | 0.0207 | BC0025 | 0.0209 | BH0035 | 0.0277 | YAAK | 0.0378 | OB0030 | 0.0015 |
| GK0019 | 3.3 | DNA repair and genetic recombination protein | 0.0406 | BC0026 | 0.0375 | BH0036 | 0.0492 | RECR | 0.0270 | OB0031 | 0.0270 |
| GK0020 | 5 | unknown conserved protein | 0.0201 | BC0027 | 0.0188 | BH0037 | 0.0270 | YAAL | 0.0437 | OB0032 | 0.0258 |
| GK0022 | 5 | unknown conserved protein | -0.0203 | BC0034 | 0.0528 | BH0040 | 0.0510 | CSFB | -0.0060 | OB0034 | 0.0471 |
| GK0023 | 2.2 | lysine decarboxylase | 0.0109 | BC0035 | 0.0121 | BH0041 | -0.0118 | YAAO | | OB0035 | -0.0057 |
| GK0024 | 2.3 | thymidylate kinase (EC 2.7.4.9) | 0.0472 | BC0036 | 0.0430 | BH0042 | 0.0328 | TMK | 0.0280 | OB0036 | 0.0322 |
| GK0025 | 3.1 | DNA-directed DNA polymerase III (EC 2.7.7.7) delta' subunit | -0.0300 | BC0037 | -0.0260 | BH0044 | -0.0193 | HOLB | -0.0336 | OB0039 | -0.0371 |
| GK0026 | 1.6 | signal peptidase II | 0.0726 | BC0038 | 0.0424 | BH0045 | 0.0512 | YAAT | 0.0492 | OB0040 | 0.0578 |
| GK0027 | 5 | unknown conserved protein | 0.0089 | BC0039 | 0.0188 | BH0046 | 0.0426 | YABA | -0.0016 | OB0041 | 0.0137 |
| GK0028 | 5 | unknown conserved protein | 0.0262 | BC0040 | 0.0104 | BH0047 | -0.0011 | YABB | 0.0120 | OB0042 | 0.0082 |
| GK0029 | 5 | unknown conserved protein | 0.0191 | BC0041 | 0.0354 | BH0049 | 0.0196 | YABC | 0.0402 | OB0044 | 0.0343 |
| GK0030 | 3.5.2 | transition state regulator | 0.0609 | BC0042 | 0.0589 | BH0050 | 0.0195 | ABRB | 0.0358 | OB0045 | 0.0355 |
| GK0031 | 3.7.2 | methionyl-tRNA synthetase (Methionine--tRNA ligase) (EC 6.1.1.10) | 0.0375 | BC0043 | 0.0351 | BH0053 | 0.0211 | METS | 0.0326 | OB0046 | 0.0296 |
| GK0032 | 2.3 | deoxyribonuclease | 0.0262 | BC0044 | 0.0568 | BH0054 | 0.0644 | YABD | 0.0581 | OB0047 | 0.0379 |
| GK0034 | 5 | unknown conserved protein | 0.0598 | BC0045 | 0.0533 | BH0056 | 0.0404 | YABF | 0.0255 | OB0049 | 0.0200 |
| GK0035 | 4.2 | dimethyladenosine transferase (EC 2.1.1.-) | 0.0185 | BC0046 | 0.0293 | BH0057 | 0.0162 | KSGA | 0.0161 | OB0050 | -0.0063 |
| GK0036 | 5 | unknown conserved protein | 0.0422 | BC0047 | 0.0366 | BH0058 | 0.0317 | YABG | 0.0059 | OB0051 | 0.0165 |
| GK0037 | 4.6 | veg protein | 0.0144 | BC0048 | 0.0044 | BH0059 | 0.0420 | VEG | -0.0080 | OB0053 | 0.0230 |
| GK0038 | 1.8 | small acid-soluble spore protein (minor alpha/beta-type SASP) | 0.0541 | BC0049 | 0.0363 | BH0060 | 0.0472 | SSPF | 0.0263 | OB0054 | 0.0516 |
| GK0039 | 2.1.1 | 4-diphosphocytidyl-2-C-methyl-D-erythritol kinase (4-(cytidine-5'-diphospho)-2-C-methyl-D-erythritol kinase) | 0.0177 | BC0050 | 0.0224 | BH0061 | 0.0143 | YABH | 0.0170 | OB0055 | -0.0143 |
| GK0040 | 3.5.2 | transcriptional repressor of the purine operon | 0.0289 | BC0051 | 0.0158 | BH0062 | 0.0262 | PURR | 0.0090 | OB0056 | 0.0148 |
| GK0041 | 3.7.3 | translation initiation inhibitor | 0.0033 | BC0052 | -0.0060 | BH0063 | 0.0237 | YABJ | 0.0227 | OB3060 | 0.0170 |
| GK0042 | 1.8 | stage V sporulation protein G | 0.0533 | BC0053 | 0.0581 | BH0064 | 0.0362 | SPOVG | 0.0334 | OB0057 | 0.0472 |
| GK0043 | 1.1 | UDP-N-acetylglucosamine pyrophosphorylase (EC 2.7.7.23) | 0.0318 | BC0054 | 0.0171 | BH0065 | 0.0199 | GCAD | 0.0240 | OB0058 | 0.0219 |
| GK0044 | 2.3 | ribose-phosphate pyrophosphokinase (phosphoribosyl pyrophosphate synthetase) | 0.0233 | BC0055 | 0.0163 | BH0066 | 0.0282 | PRS | 0.0141 | OB0059 | 0.0026 |
| GK0046 | 1.8 | stage V sporulation protein C (peptidyl-tRNA hydrolase) | 0.0284 | BC0056 | 0.0200 | BH0068 | 0.0376 | SPOVC | 0.0279 | OB0061 | 0.0143 |
| GK0048 | 3.5.3 | transcription-repair coupling factor | 0.0284 | BC0058 | 0.0198 | BH0069 | 0.0204 | MFD | 0.0221 | OB0063 | 0.0176 |
| GK0049 | 3.5.2 | stage V sporulation protein T (transcriptional regulator) | 0.0681 | BC0059 | 0.0579 | BH0070 | 0.0337 | SPOVT | 0.0398 | OB0064 | 0.0379 |
| GK0051 | 5 | unknown conserved protein | 0.0365 | BC0061 | 0.0406 | BH0072 | 0.0387 | YABN | 0.0439 | OB0066 | 0.0288 |
| GK0052 | 5 | unknown conserved protein | 0.0480 | BC0062 | 0.0476 | BH0073 | 0.0911 | YABO | 0.0271 | OB0067 | 0.0613 |
| GK0053 | 5 | unknown conserved protein | 0.0261 | BC0063 | 0.0124 | BH0074 | 0.0407 | YABP | 0.0123 | OB0068 | 0.0399 |
| GK0055 | 1.7 | cell-division initiation protein | 0.0202 | BC0065 | 0.0183 | BH0076 | 0.0031 | DIVIC | 0.0201 | OB0070 | 0.0132 |
| GK0056 | 2.3 | polyribonucleotide nucleotidyltransferase | 0.0318 | BC0066 | 0.0445 | BH0077 | 0.0477 | YABR | 0.0351 | OB0071 | 0.0585 |
| GK0060 | 5 | unknown conserved protein | 0.0198 | BC0070 | 0.0171 | BH0083 | 0.0189 | YACA | -0.0112 | OB0077 | -0.0094 |
| GK0061 | 2.3 | hypoxanthine-guanine phosphoribosyltransferase (EC 2.4.2.8) | 0.0357 | BC0071 | 0.0365 | BH0084 | 0.0692 | HPRT | 0.0459 | OB0078 | 0.0384 |
| GK0062 | 1.7 | cell-division protein and general stress protein (class III heat-shock) | 0.0321 | BC0072 | 0.0253 | BH0085 | 0.0344 | FTSH | 0.0249 | OB0079 | 0.0249 |
| GK0063 | 5 | unknown conserved protein | 0.0261 | BC0073 | 0.0549 | BH0086 | 0.0151 | YACB | 0.0139 | OB0081 | 0.0086 |
| GK0064 | 4.1 | chaperonin (heat shock protein 33) (HSP33) | 0.0256 | BC0074 | 0.0388 | BH0087 | 0.0355 | YACC | 0.0341 | OB0082 | 0.0211 |
| GK0065 | 2.2 | cysteine synthase (O-acetyl-L-serine sulfhydrylase) (EC 4.2.99.8) | 0.0341 | BC0075 | 0.0421 | BH0088 | 0.0245 | CYSK | 0.0333 | OB0084 | 0.0244 |
| GK0067 | 2.5 | para-aminobenzoate synthases component II (EC 4.1.3.-) | 0.0220 | BC0077 | 0.0059 | BH0091 | 0.0248 | PABA | 0.0292 | OB0701 | 0.0069 |
| GK0069 | 2.5 | dihydropteroate synthase (EC 2.5.1.15) | 0.0464 | BC0079 | 0.0406 | BH0093 | 0.0308 | SUL | 0.0272 | OB0085 | 0.0202 |
| GK0070 | 2.5 | dihydroneopterin aldolase (EC 4.1.2.25) | 0.0612 | BC0080 | 0.0700 | BH0094 | 0.0515 | FOLA | 0.0523 | OB0086 | 0.0380 |
| GK0071 | 2.5 | 7,8-dihydro-6-hydroxymethylpterin pyrophosphokinase (2-amino-4-hydroxy-6-hydroxymethyldihydropteridine pyrophosphokinase) (EC 2.7.6.3) | 0.0064 | BC0081 | 0.0075 | BH0095 | 0.0299 | FOLK | 0.0125 | OB0087 | 0.0169 |
| GK0074 | 3.7.2 | lysyl-tRNA synthetase (lysine--tRNA ligase) (EC 6.1.1.6) | 0.0391 | BC0084 | 0.0388 | BH0098 | 0.0408 | LYSS | 0.0316 | OB0088 | 0.0355 |
| GK0075 | 3.5.2 | transcriptional regulator | 0.0244 | BC0099 | 0.0194 | BH0100 | 0.0157 | CTSR | 0.0158 | OB0090 | -0.0014 |
| GK0076 | 5 | unknown conserved protein | -0.0162 | BC0100 | 0.0085 | BH0101 | 0.0084 | YACH | -0.0192 | OB0091 | 0.0056 |
| GK0077 | 2.2 | creatine kinase | 0.0046 | BC0101 | -0.0035 | BH0102 | -0.0063 | YACI | -0.0021 | OB0092 | 0.0036 |
| GK0079 | 3.2 | DNA repair protein | 0.0329 | BC0103 | 0.0243 | BH0104 | 0.0279 | SMS | 0.0167 | OB0094 | 0.0311 |

Fig. 10 B

| GK ID | EC | Description | val1 | col2 | val2 | col3 | val3 | col4 | val4 | col5 | val5 |
|---|---|---|---|---|---|---|---|---|---|---|---|
| GK0083 | 3.7.2 | glutamyl-tRNA synthetase (glutamate--tRNA ligase) (EC 6.1.1.17) | 0.0320 | BC0108 | 0.0381 | BH0109 | 0.0252 | GLTX | 0.0386 | OB0096 | 0.0198 |
| GK0084 | 2.2 | serine O-acetyltransferase (EC 2.3.1.30) | 0.0418 | BC0109 | 0.0381 | BH0110 | 0.0306 | CYSE | 0.0266 | OB0098 | 0.0320 |
| GK0085 | 3.7.2 | cysteinyl-tRNA synthetase (EC 6.1.1.16) | 0.0163 | BC0110 | 0.0213 | BH0111 | 0.0332 | CYSS | 0.0120 | OB0059 | 0.0093 |
| GK0086 | 5 | unknown conserved protein | 0.0512 | BC0111 | -0.0020 | BH0112 | 0.0009 | YAZC | -0.0170 | OB0100 | 0.0055 |
| GK0087 | 3.6 | tRNA/rRNA methyltransferase | 0.0280 | BC0112 | 0.0257 | BH0113 | 0.0358 | YACO | 0.0242 | OB0101 | 0.0167 |
| GK0088 | 5 | unknown conserved protein | 0.0510 | BC0113 | 0.0165 | BH0114 | 0.0541 | YACP | 0.0336 | OB0102 | 0.0610 |
| GK0089 | 3.5.1 | DNA-directed RNA polymerase sigma-H factor (sigma-30) | 0.0207 | BC0114 | 0.0284 | BH0115 | 0.0148 | SIGH | 0.0149 | OB0103 | -0.0175 |
| GK0091 | 1.6 | preprotein translocase subunit | 0.0551 | BC0115 | 0.0270 | BH0117 | 0.0762 | SECE | 0.0392 | OB0105 | 0.0262 |
| GK0092 | 3.5.4 | transcription antitermination factor | 0.0919 | BC0116 | 0.0970 | BH0118 | 0.0756 | NUSG | 0.0838 | OB0106 | 0.0761 |
| GK0093 | 3.7.1 | 50S ribosomal protein L11 (BL11) | 0.0312 | BC0117 | 0.0369 | BH0119 | 0.0394 | RPLK | 0.0449 | OB0107 | 0.0234 |
| GK0094 | 3.7.1 | 50S ribosomal protein L1 | 0.0493 | BC0118 | 0.0476 | BH0120 | 0.0470 | RPLA | 0.0509 | OB0108 | 0.0399 |
| GK0095 | 3.7.1 | 50S ribosomal protein L10 | 0.0351 | BC0119 | 0.0230 | BH0121 | 0.0363 | RPLJ | 0.0435 | OB0109 | 0.0404 |
| GK0096 | 3.7.1 | 50S ribosomal protein L7/L12 (BL13) | 0.1021 | BC0120 | 0.0175 | BH0122 | 0.1014 | RPLL | 0.0933 | OB0110 | 0.1001 |
| GK0097 | 5 | unknown conserved protein | 0.0263 | BC0121 | 0.0359 | BH0124 | 0.0144 | YBXB | 0.0189 | OB0111 | 0.0028 |
| GK0098 | 3.5.3 | DNA-directed RNA polymerase beta subunit | 0.0419 | BC0122 | 0.0393 | BH0126 | 0.0407 | RPOB | 0.0392 | OB0112 | 0.0388 |
| GK0099 | 3.5.3 | DNA-directed RNA polymerase beta' subunit | 0.0327 | BC0123 | 0.0266 | BH0127 | 0.0360 | RPOC | 0.0278 | OB0113 | 0.0283 |
| GK0101 | 3.7.1 | 30S ribosomal protein S12 | 0.0173 | BC0125 | 0.0102 | BH0129 | 0.0019 | RPSL | 0.0168 | OB0114 | 0.0108 |
| GK0102 | 3.7.1 | 30S ribosomal protein S7 (BS7) | 0.0382 | BC0126 | 0.0422 | BH0130 | 0.0429 | RPSG | 0.0388 | OB0115 | 0.0379 |
| GK0103 | 3.7.4 | translation elongation factor G (EF-G) | 0.0389 | BC0128 | 0.0499 | BH0131 | 0.0392 | FUS | 0.0462 | OB0116 | 0.0412 |
| GK0104 | 3.7.4 | translation elongation factor Tu (EF-Tu) | 0.0556 | BC0129 | 0.0560 | BH0132 | 0.0585 | TUFA | 0.0593 | OB0117 | 0.0617 |
| GK0105 | 3.7.1 | 30S ribosomal protein S10 (BS13) | 0.0248 | BC0130 | 0.0249 | BH0133 | 0.0152 | RPSJ | 0.0131 | OB0118 | 0.0337 |
| GK0106 | 3.7.1 | 50S ribosomal protein L3 | 0.0371 | BC0131 | 0.0339 | BH0134 | 0.0380 | RPLC | 0.0511 | OB0119 | 0.0343 |
| GK0107 | 3.7.1 | 50S ribosomal protein L4 | 0.0226 | BC0132 | 0.0372 | BH0135 | 0.0241 | RPLD | 0.0239 | OB0120 | 0.0103 |
| GK0108 | 3.7.1 | 50S ribosomal protein L23 | 0.0678 | BC0133 | 0.0737 | BH0136 | 0.0614 | RPLW | 0.0776 | OB0121 | 0.0555 |
| GK0109 | 3.7.1 | 50S ribosomal protein L2 | 0.0341 | BC0134 | 0.0255 | BH0137 | 0.0259 | RPLB | 0.0228 | OB0122 | 0.0299 |
| GK0110 | 3.7.1 | 30S ribosomal protein S19 (BS19) | 0.0255 | BC0135 | 0.0230 | BH0138 | 0.0462 | RPSS | 0.0258 | OB0123 | 0.0372 |
| GK0111 | 3.7.1 | 50S ribosomal protein L22 | 0.0306 | BC0136 | 0.0435 | BH0139 | 0.0326 | RPLV | 0.0116 | OB0124 | 0.0414 |
| GK0112 | 3.7.1 | 30S ribosomal protein S3 (BS2) | 0.0437 | BC0137 | 0.0458 | BH0140 | 0.0395 | RPSC | 0.0312 | OB0125 | 0.0286 |
| GK0113 | 3.7.1 | 50S ribosomal protein L16 | 0.0838 | BC0138 | 0.0670 | BH0141 | 0.0764 | RPLP | 0.0742 | OB0126 | 0.0664 |
| GK0114 | 3.7.1 | 50S ribosomal protein L29 | 0.0266 | BC0139 | 0.0545 | BH0142 | 0.0052 | RPMC | 0.0357 | OB0127 | 0.0116 |
| GK0115 | 3.7.1 | 30S ribosomal protein S17 | 0.0631 | BC0140 | 0.0483 | BH0143 | 0.0670 | RPSQ | 0.0648 | OB0128 | 0.0738 |
| GK0116 | 3.7.1 | 50S ribosomal protein L14 | 0.0673 | BC0141 | 0.0413 | BH0144 | 0.0399 | RPLN | 0.0504 | OB0129 | 0.0492 |
| GK0117 | 3.7.1 | 50S ribosomal protein L24 | 0.0614 | BC0142 | 0.0510 | BH0145 | 0.0705 | RPLX | 0.0437 | OB0130 | 0.0695 |
| GK0118 | 3.7.1 | 50S ribosomal protein L5 | 0.0327 | BC0143 | 0.0351 | BH0146 | 0.0471 | RPLE | 0.0382 | OB0131 | 0.0284 |
| GK0119 | 3.7.1 | 30S ribosomal protein S14 | 0.0170 | BC0144 | 0.0255 | BH0147 | 0.0290 | RPSN | 0.0150 | OB0132 | 0.0194 |
| GK0120 | 3.7.1 | 30S ribosomal protein S8 | 0.0507 | BC0145 | 0.0493 | BH0148 | 0.0501 | RPSH | 0.0449 | OB0133 | 0.0384 |
| GK0121 | 3.7.1 | 50S ribosomal protein L6 | 0.0774 | BC0146 | 0.0815 | BH0149 | 0.0934 | RPLF | 0.0780 | OB0134 | 0.0669 |
| GK0122 | 3.7.1 | 50S ribosomal protein L18 | 0.0337 | BC0147 | 0.0230 | BH0150 | 0.0345 | RPLR | 0.0121 | OB0135 | 0.0280 |
| GK0123 | 3.7.1 | 30S ribosomal protein S5 | 0.0669 | BC0148 | 0.0531 | BH0151 | 0.0758 | RPSE | 0.0612 | OB0136 | 0.0400 |
| GK0124 | 3.7.1 | 50S ribosomal protein L30 | 0.0358 | BC0149 | 0.0279 | BH0152 | 0.0103 | RPMD | 0.0245 | OB0137 | 0.0520 |
| GK0125 | 3.7.1 | 50S ribosomal protein L15 | 0.0422 | BC0150 | 0.0421 | BH0153 | 0.0523 | RPLO | 0.0387 | OB0138 | 0.0406 |
| GK0127 | 2.3 | adenylate kinase (ATP-AMP transphosphorylase) | 0.0295 | BC0152 | 0.0115 | BH0155 | 0.0111 | ADK | 0.0491 | OB0140 | 0.0235 |
| GK0129 | 3.7.3 | translation initiation factor IF-1 | 0.0645 | BC0154 | 0.0604 | BH0158 | 0.0736 | INFA | 0.0640 | OB0141 | 0.0536 |
| GK0130 | 3.7.1 | 50S ribosomal protein L36 | 0.0699 | BC0155 | 0.0763 | BH0159 | 0.0685 | RPMJ | 0.0757 | OB0142 | 0.0719 |
| GK0131 | 3.7.1 | 30S ribosomal protein S13 | 0.0675 | BC0156 | 0.0641 | BH0160 | 0.0591 | RPSM | 0.0556 | OB0143 | 0.0360 |
| GK0132 | 3.7.1 | 30S ribosomal protein S11 | 0.0051 | BC0157 | 0.0006 | BH0161 | 0.0085 | RPSK | 0.0018 | OB0144 | 0.0093 |
| GK0133 | 3.5.3 | DNA-directed RNA polymerase alpha subunit (EC 2.7.7.6) | 0.0459 | BC0158 | 0.0467 | BH0162 | 0.0439 | RPOA | 0.0398 | OB0145 | 0.0447 |
| GK0134 | 3.7.1 | 50S ribosomal protein L17 | 0.0096 | BC0159 | 0.0143 | BH0163 | 0.0381 | RPLQ | 0.0213 | OB0146 | 0.0214 |
| GK0135 | 1.2 | ABC transporter (ATP-binding protein) | 0.0321 | BC0160 | 0.0041 | BH0164 | 0.0110 | YBXA | 0.0220 | OB0147 | 0.0107 |
| GK0136 | 1.2 | ABC transporter (ATP-binding protein) | 0.0343 | BC0161 | 0.0343 | BH0165 | -0.0001 | YBAE | 0.0156 | OB0148 | 0.0047 |
| GK0138 | 3.6 | pseudouridylate synthase I (EC 4.2.1.70) | 0.0114 | BC0163 | 0.0120 | BH0167 | 0.0109 | TRUA | 0.0090 | OB0150 | 0.0094 |
| GK0139 | 3.7.1 | 50S ribosomal protein L13 | 0.0362 | BC0164 | 0.0145 | BH0168 | 0.0264 | RPLM | 0.0238 | OB0151 | 0.0296 |
| GK0140 | 3.7.1 | 30S ribosomal protein S9 | 0.0407 | BC0165 | 0.0291 | BH0169 | 0.0239 | RPSI | 0.0252 | OB0152 | -0.0076 |
| GK0142 | 1.1 | germination-specific N-acetylmuramoyl-L-alanine amidase (cell wall hydrolase) (autolysin) (EC 3.5.1.28) | -0.0059 | BC0167 | 0.0019 | BH0239 | -0.0109 | CWLD | 0.0037 | OB0195 | -0.0051 |
| GK0143 | 1.7 | ATPase involved in chromosome partitioning | 0.0380 | BC0168 | 0.0424 | BH0240 | 0.0454 | YBAL | 0.0544 | OB0196 | 0.0503 |
| GK0144 | 1.9 | spore germination protein precursor (C-term divided by IS) | 0.0050 | BC0169 | 0.0102 | BH0241 | 0.0059 | GERD | 0.0025 | OB0197 | -0.0226 |
| GK0148 | 2.1.1 | polysaccharide deacetylase | 0.0034 | BC0171 | -0.0282 | BH0243 | -0.0007 | YBAN | -0.0151 | OB0199 | 0.0289 |
| GK0153 | 5 | unknown conserved protein | 0.0435 | BC0187 | -0.0044 | BH0266 | 0.0595 | YBBR | -0.0150 | OB0231 | 0.0423 |
| GK0154 | 2.1.2 | phosphoglucomutase (glycolysis) | 0.0312 | BC0188 | 0.0339 | BH0267 | 0.0203 | YBFT | 0.0331 | OB0232 | 0.0280 |
| GK0155 | 2.2 | L-glutamine-D-fructose-6-phosphate amidotransferase (EC 2.6.1.16) | 0.0173 | BC0190 | 0.0189 | BH0268 | 0.0198 | GLMS | 0.0179 | OB0215 | 0.0139 |
| GK0188 | 2.2 | ornithine aminotransferase (EC 2.6.1.13) | 0.0279 | BC1149 | 0.0293 | BH3943 | 0.0321 | ROCD | 0.0265 | OB2287 | 0.0267 |
| GK0224 | 1.1 | UDP-N-acetylmuramoylalanyl-D-glutamyl-2,6-diaminopimelate-D-alanyl-D-alanyl ligase (EC 6.3.2.15) | 0.0254 | BC0258 | 0.0202 | BH2570 | 0.0112 | MURF | 0.0059 | OB1467 | -0.0033 |
| GK0226 | 3.6 | ATP-dependent RNA helicase | 0.0345 | BC0259 | 0.0266 | BH2384 | 0.0228 | YDBR | 0.0056 | OB0609 | 0.0178 |
| GK0228 | 2.4 | holo-[acyl-carrier protein] synthase | 0.0351 | BC0262 | 0.0580 | BH0518 | 0.0356 | YDCB | 0.0032 | OB0619 | 0.0457 |
| GK0229 | 5 | unknown conserved protein | 0.0129 | BC0263 | -0.0084 | BH0519 | 0.0086 | YDCC | -0.0106 | OB0621 | 0.0096 |
| GK0232 | 5 | unknown conserved protein | 0.0377 | BC0265 | 0.0211 | BH0521 | 0.0192 | YDCD | 0.0393 | OB0622 | 0.0341 |
| GK0233 | 5 | unknown conserved protein | 0.0155 | BC0266 | 0.0188 | BH0522 | -0.0037 | YDCE | 0.0092 | OB0623 | 0.0066 |
| GK0234 | 5 | unknown conserved protein | 0.0467 | BC0267 | 0.0445 | BH0531 | 0.0455 | YDCI | 0.0367 | OB0632 | 0.0220 |
| GK0235 | 5 | unknown conserved protein | 0.0006 | BC0268 | 0.0495 | BH0532 | 0.0075 | YDCK | 0.0023 | OB0634 | 0.0271 |
| GK0236 | 5 | unknown conserved protein | 0.0533 | BC0286 | 0.0472 | BH0545 | 0.0431 | YDIB | 0.0363 | OB0645 | 0.0479 |
| GK0237 | 3.8 | glycoprotein endopeptidase | 0.0268 | BC0287 | 0.0200 | BH0546 | 0.0144 | YDIC | -0.0066 | OB0646 | 0.0148 |
| GK0238 | 3.8 | ribosomal-protein (S18)-alanine acetyltransferase | 0.0193 | BC0288 | 0.0328 | BH0547 | 0.0513 | YDID | 0.0210 | OB0647 | 0.0195 |
| GK0239 | 3.8 | glycoprotein endopeptidase | 0.0156 | BC0289 | 0.0313 | BH0548 | 0.0166 | YDIE | 0.0144 | OB0648 | 0.0214 |
| GK0240 | 1.2 | ABC transporter (ATP-binding protein) | -0.0001 | BC0290 | -0.0013 | BH0550 | 0.0029 | YDIH | 0.0015 | OB0651 | 0.0138 |
| GK0242 | 5 | unknown conserved protein | 0.0000 | BC0291 | -0.0128 | BH0551 | -0.0114 | YDIJ | -0.0077 | OB0652 | -0.0025 |
| GK0245 | 5 | unknown conserved protein | -0.0496 | BC0293 | -0.0579 | BH0559 | -0.0303 | YDIK | -0.0415 | OB0653 | -0.0119 |

Fig. 10 C

| Gene | Val | Description | V1 | Col | V2 | Col | V3 | Col | V4 | Col | V5 |
|---|---|---|---|---|---|---|---|---|---|---|---|
| GK0248 | 3.9 | chaperonin (GroES protein) | 0.1018 | BC0294 | 0.0826 | BH0561 | 0.1012 | GROES | 0.0940 | OB0655 | 0.0988 |
| GK0249 | 3.9 | chaperonin (GroEL protein) | 0.0545 | BC0295 | 0.0533 | BH0562 | 0.0516 | GROEL | 0.0549 | OB0656 | 0.0487 |
| GK0250 | 2.1.3 | fumarate hydratase (EC 4.2.1.2) | 0.0034 | BG1712 | 0.0042 | BH1445 | -0.0268 | CITG | -0.0083 | OB1132 | -0.0153 |
| GK0251 | 2.1.1 | methanol dehydrogenase regulatory protein (MoxR protein) | 0.0113 | BC2117 | -0.0013 | BH0604 | 0.0228 | YEAG | 0.0114 | OB0713 | 0.0080 |
| GK0254 | 2.3 | GMP synthetase (glutamine amidotransferase) (EC 6.3.5.2) | 0.0352 | BC0296 | 0.0455 | BH0607 | 0.0318 | GUAA | 0.0397 | OB0716 | 0.0290 |
| GK0257 | 2.3 | phosphoribosylaminoimidazole carboxylase I (EC 4.1.1.21) catalytic chain | 0.0222 | BC0323 | 0.0237 | BH0623 | 0.0337 | PURE | 0.0054 | OB0739 | 0.0144 |
| GK0258 | 2.3 | phosphoribosylaminoimidazole carboxylase II (EC 4.1.1.21) carbon dioxide-fixation chain | 0.0264 | BC0324 | 0.0132 | BH0624 | 0.0289 | PURK | 0.0217 | OB0740 | 0.0101 |
| GK0259 | 2.3 | adenylosuccinate lyase (glutamyl-tRNA synthetase regulatory factor) (EC 4.3.2.2) | 0.0387 | BC0325 | 0.0346 | BH0625 | 0.0462 | PURB | 0.0284 | OB0741 | 0.0309 |
| GK0260 | 2.3 | phosphoribosylaminoimidazole succinocarboxamide synthetase | 0.0221 | BC0326 | 0.0410 | BH0626 | 0.0316 | PURC | 0.0323 | OB0742 | 0.0071 |
| GK0261 | 2.3 | phosphoribosylformylglycinamidine (FGAM) synthase (EC 6.3.5.3) PurS component | 0.0929 | BC0327 | 0.0644 | BH0627 | 0.0630 | YEXA | 0.0616 | OB0743 | 0.0554 |
| GK0262 | 2.3 | phosphoribosylformylglycinamidine (FGAM) synthase (EC 6.3.5.3) component I (glutamine amidotransferase domain) | 0.0321 | BC0328 | 0.0247 | BH0628 | 0.0311 | PURL | 0.0224 | OB0744 | 0.0146 |
| GK0263 | 2.3 | phosphoribosylformylglycinamidine (FGAM) synthase (EC 6.3.5.3) component II (synthetase domain) | 0.0302 | BC0329 | 0.0357 | BH0629 | 0.0294 | PURQ | 0.0241 | OB0745 | 0.0101 |
| GK0264 | 2.3 | phosphoribosylpyrophosphate amidotransferase (EC 2.4.2.14) | 0.0086 | BC0330 | 0.0341 | BH0630 | 0.0148 | PURF | 0.0105 | OB0746 | 0.0309 |
| GK0265 | 2.3 | phosphoribosylaminoimidazole synthetase (phosphoribosylformylglycinamidine cyclo-ligase) (EC 6.3.3.1) | 0.0467 | BC0331 | 0.0600 | BH0631 | 0.0371 | PURM | 0.0494 | OB0747 | 0.0431 |
| GK0266 | 2.3 | phosphoribosylglycinamide formyltransferase (EC 2.1.2.2) | 0.0395 | BC0332 | 0.0275 | BH0632 | 0.0292 | PURN | 0.0199 | OB0748 | 0.0163 |
| GK0267 | 2.3 | phosphoribosylaminoimidazolecarboxamide formyltransferase; IMP cyclohydrolase (bifunctional purine biosynthesis protein) | 0.0144 | BC0333 | 0.0252 | BH0633 | 0.0322 | PURH | 0.0222 | OB0749 | -0.0012 |
| GK0268 | 2.3 | phosphoribosylglycinamide synthetase (glycinamide ribonucleotide synthetase) (phosphoribosylglycinamide synthetase) | 0.0361 | BC0334 | 0.0391 | BH0634 | 0.0386 | PURD | 0.0412 | OB0750 | 0.0220 |
| GK0271 | 2.3 | adenine deaminase | 0.0131 | BG3012 | 0.0052 | BH0637 | 0.0093 | YERA | 0.0027 | OB0751 | -0.0026 |
| GK0274 | 5 | unknown conserved protein | 0.0318 | BC0339 | 0.0468 | BH0647 | 0.0202 | YERE | 0.0445 | OB0758 | 0.0388 |
| GK0275 | 3.1 | ATP-dependent DNA helicase | 0.0101 | BC0340 | 0.0100 | BH0648 | 0.0141 | YERF | 0.0042 | OB0759 | 0.0098 |
| GK0276 | 3.1 | DNA ligase (polydeoxyribonucleotide synthase [NAD+]) (EC 6.5.1.2.) | 0.0388 | BC0341 | 0.0445 | BH0649 | 0.0381 | YERG | 0.0421 | OB0760 | 0.0254 |
| GK0277 | 5 | unknown conserved protein | 0.0177 | BC0342 | 0.0307 | BH0650 | 0.0272 | YERH | 0.0141 | OB0761 | 0.0351 |
| GK0278 | 5 | unknown conserved protein | 0.0197 | BC5046 | 0.0541 | BH3084 | 0.0183 | YVDD | 0.0302 | OB0339 | 0.0113 |
| GK0281 | 3.7.2 | aspartyl/glutamyl-tRNA(Asn/Gln) amidotransferase (EC 6.3.5.-) subunit C (Glu-ADT subunit C) | 0.0202 | BC0350 | 0.0245 | BH0665 | 0.0448 | YERL | 0.0580 | OB0764 | 0.0170 |
| GK0282 | 3.7.2 | aspartyl/glutamyl-tRNA(Asn/Gln) amidotransferase (EC 6.3.5.-) subunit A (Glu-ADT subunit A) | 0.0124 | BC0351 | 0.0072 | BH0666 | 0.0048 | YERM | 0.0091 | OB0765 | 0.0222 |
| GK0283 | 3.7.2 | aspartyl/glutamyl-tRNA(Asn/Gln) amidotransferase (EC 6.3.5.-) subunit B (Asp/Glu-ADT subunit B) | 0.0317 | BC0352 | 0.0276 | BH0667 | 0.0335 | YERN | 0.0411 | OB0766 | 0.0286 |
| GK0325 | 5 | unknown conserved protein | 0.0051 | BC4801 | 0.0046 | BH1196 | 0.0306 | YVQH | 0.0182 | OB0940 | 0.0246 |
| GK0340 | 4.6 | epidermal surface antigen | 0.0343 | BC0558 | 0.0489 | BH3500 | 0.0414 | YUAG | 0.0334 | OB0205 | 0.0259 |
| GK0341 | 5 | unknown conserved protein | 0.0382 | BC0353 | 0.0216 | BH0676 | 0.0170 | YERQ | 0.0108 | OB0767 | 0.0169 |
| GK0342 | 3.6 | RNA methyltransferase | 0.0523 | BC0364 | 0.0369 | BH0687 | 0.0360 | YEFA | 0.0401 | OB0768 | 0.0183 |
| GK0393 | 5 | unknown conserved protein | -0.0111 | BC1305 | 0.0194 | BH1834 | 0.0160 | YVBY | 0.0116 | OB0372 | 0.0069 |
| GK0394 | 5 | unknown conserved protein | 0.0239 | BC1304 | 0.0217 | BH1833 | 0.0100 | YVBW | 0.0277 | OB0371 | 0.0200 |
| GK0395 | 2.1.1 | glycolate oxidase | 0.0279 | BC1303 | 0.0378 | BH1832 | 0.0356 | YVBV | 0.0235 | OB0370 | 0.0356 |
| GK0396 | 3.5.2 | transcriptional regulator (GntR family) | 0.0055 | BC1302 | 0.0047 | BH1835 | 0.0066 | YVBU | 0.0077 | OB0369 | -0.0018 |
| GK0402 | 5 | unknown conserved protein | 0.0794 | BC0430 | 0.0289 | BH0859 | 0.0433 | YFLB | 0.0287 | OB0398 | 0.0055 |
| GK0404 | 2.5 | siroheme synthase | 0.0660 | BC1428 | 0.0339 | BH1497 | 0.0112 | YLNF | 0.0338 | OB1657 | 0.0142 |
| GK0407 | 5 | unknown conserved protein | 0.0239 | BC3461 | 0.0324 | BH3320 | 0.0151 | YOJG | 0.0670 | OB2485 | 0.0403 |
| GK0408 | 5 | unknown conserved protein | 0.0035 | BC3462 | 0.0232 | BH3319 | -0.0148 | YOJF | 0.0319 | OB2486 | 0.0131 |
| GK0416 | 2.2 | phosphoadenylyl-sulfate reductase (thioredoxin-dependent) (EC 1.8.4.8) | 0.0208 | BC1421 | 0.0307 | BH1486 | 0.0143 | CYSH | 0.0210 | OB1652 | -0.0094 |
| GK0418 | 5 | unknown conserved protein | 0.0317 | BC0449 | 0.0691 | BH2488 | 0.0503 | YFKK | -0.0050 | OB1527 | 0.0025 |
| GK0419 | 3.8 | protein-tyrosine phosphatase | 0.0423 | BC0450 | 0.0313 | BH2238 | 0.0222 | YFKJ | 0.0044 | OB0873 | -0.0197 |
| GK0424 | 5 | unknown conserved protein | -0.0027 | BC0463 | -0.0233 | BH0888 | -0.0154 | YFKD | -0.0058 | OB0878 | -0.0060 |
| GK0427 | 2.1.1 | nodulation protein | -0.0014 | BC0467 | 0.0047 | BH0895 | 0.0201 | YFIS | -0.0084 | OB0880 | -0.0096 |
| GK0432 | 5 | unknown conserved protein | 0.0165 | BC1437 | 0.0345 | BH1198 | 0.0124 | YVQF | -0.0007 | OB2824 | 0.0065 |
| GK0433 | 1.3 | two-component sensor histidine kinase | -0.0003 | BC1438 | 0.0227 | BH1199 | -0.0005 | YVQE | 0.0072 | OB2823 | 0.0037 |
| GK0438 | 3.5.2 | transcriptional activator | 0.0273 | BC4968 | 0.0181 | BH0408 | 0.0124 | MTA | 0.0077 | OB0382 | -0.0081 |
| GK0451 | 1.7 | cell-division inhibitor | -0.0066 | BC0497 | -0.0264 | BH3889 | 0.0053 | YFHF | -0.0076 | OB0892 | -0.0201 |
| GK0452 | 5 | unknown conserved protein | 0.0181 | BC0498 | 0.0323 | BH0924 | 0.0219 | YFHG | 0.0213 | OB0893 | 0.0010 |
| GK0453 | 5 | unknown conserved protein | 0.0562 | BC0499 | 0.0498 | BH0925 | 0.0324 | YFHH | 0.0256 | OB0894 | 0.0302 |
| GK0463 | 3.2 | adenine glycosylase | 0.0471 | BC0504 | 0.0395 | BH0931 | 0.0130 | YFHQ | 0.0242 | OB0896 | -0.0123 |
| GK0464 | 5 | unknown conserved protein | 0.0419 | BC0505 | 0.0344 | BH0937 | 0.0203 | YFHS | 0.0153 | OB0897 | -0.0010 |
| GK0468 | 5 | unknown conserved protein | 0.0357 | BC0508 | 0.0205 | BH0940 | 0.0221 | YGAC | 0.0038 | OB0899 | 0.0040 |
| GK0471 | 2.5 | glutamate-1-semialdehyde 2,1-aminomutase 2 (GSA) (EC 5.4.3.8) | 0.0242 | BC0512 | 0.0262 | BH0943 | 0.0059 | GSAB | 0.0282 | OB0901 | 0.0200 |
| GK0477 | 4.2 | bacterioferritin comigratory protein | 0.0274 | BC0517 | 0.0639 | BH0948 | 0.0460 | YGAF | 0.0185 | OB0903 | 0.0311 |
| GK0478 | 3.5.2 | transcriptional regulator (Fur family) | 0.0125 | BC0518 | 0.0524 | BH0951 | 0.0209 | YGAG | 0.0227 | OB0905 | 0.0033 |
| GK0482 | 5 | unknown conserved protein | 0.0162 | BC0544 | 0.0124 | BH1020 | 0.0129 | YHBA | 0.0140 | OB1085 | 0.0076 |
| GK0483 | 5 | unknown conserved protein | 0.0099 | BC0545 | 0.0018 | BH1022 | -0.0061 | YHBB | 0.0175 | OB1086 | 0.0055 |
| GK0484 | 3.6 | rRNA methylase | -0.0108 | BC0546 | 0.0137 | BH1023 | -0.0154 | GSPR | -0.0203 | OB1087 | 0.0036 |
| GK0486 | 3.8 | serine protein kinase (EC 2.7.1.37) | 0.0413 | BC0548 | 0.0287 | BH1029 | 0.0342 | PRKA | 0.0369 | OB2654 | 0.0320 |

Fig. 10 D

| GK0487 | 5 | unknown conserved protein | 0.0232 | BC0551 | 0.0248 | BH1031 | 0.0282 | YHBH | 0.0086 | OB2647 | 0.0238 |
|---|---|---|---|---|---|---|---|---|---|---|---|
| GK0567 | 5 | unknown conserved protein | -0.0108 | BC0778 | 0.0095 | BH1942 | 0.0200 | YOLJ | 0.0283 | OB1164 | 0.0109 |
| GK0568 | 3.9 | protein-disulfide oxidoreductase | -0.0239 | BC0779 | -0.0056 | BH1941 | -0.0279 | YVGU | 0.0005 | OB1163 | -0.0103 |
| GK0608 | 3.9 | chaperone | -0.0017 | BC4214 | -0.0114 | BH0685 | -0.0271 | YKKD | -0.0147 | OB3263 | 0.0068 |
| GK0614 | 2.5 | thiamine biosynthesis protein | 0.0197 | BC1806 | 0.0218 | BH1763 | 0.0205 | YKPD | 0.0229 | OB3273 | -0.0064 |
| GK0615 | 2.1.1 | exo-alpha-1,4-glucosidase (EC 3.2.1.20) | 0.0064 | BC0413 | 0.0199 | BH3868 | 0.0119 | YUGT | 0.0010 | OB2556 | -0.0045 |
| GK0616 | 5 | unknown conserved protein | -0.0042 | BC2708 | 0.0100 | BH0277 | -0.0324 | YFIT | -0.0097 | OB0782 | 0.0042 |
| GK0631 | 1.2 | sugar ABC transporter (ATP-binding protein) | 0.0305 | BC4016 | 0.0110 | BH1140 | 0.0199 | MSMX | 0.0331 | OB1134 | 0.0312 |
| GK0640 | 5 | unknown conserved protein | -0.0268 | BC0880 | -0.0293 | BH1149 | -0.0253 | YHFA | 0.0162 | OB1136 | 0.0148 |
| GK0644 | 1.2 | ABC transporter (ATP-binding protein) (Na+ exclusion) | 0.0343 | BC4510 | 0.0041 | BH1166 | 0.0199 | YHAQ | 0.0229 | OB1138 | 0.0263 |
| GK0646 | 5 | unknown conserved protein | 0.0261 | BC1021 | 0.0170 | BH1175 | 0.0006 | YHAM | 0.0081 | OB1146 | 0.0275 |
| GK0648 | 5 | unknown conserved protein | 0.0833 | BC1028 | 0.0827 | HH1176 | 0.0282 | YHAL | 0.0516 | OB1147 | 0.0386 |
| GK0657 | 4.1 | Hit-like protein (cell-cycle regulation histidine triad) | -0.0255 | BC1049 | -0.0194 | BH1189 | -0.0106 | HIT | 0.0050 | OB1154 | -0.0008 |
| GK0658 | 1.2 | ABC transporter (ATP-binding protein) | 0.0234 | BC1050 | 0.0099 | BH1191 | 0.0280 | ECSA | 0.0145 | OB1155 | 0.0060 |
| GK0661 | 2.5 | uroporphyrinogen decarboxylase (EC 4.1.1.37) | 0.0180 | BC1068 | 0.0222 | BH1202 | 0.0130 | HEMR | 0.0098 | OB1167 | 0.0114 |
| GK0663 | 2.5 | protoporphyrinogen IX /coproporphyrinogen III oxidase | 0.0198 | BC1070 | 0.0060 | BH1204 | 0.0234 | HEMY | 0.0003 | OB1169 | 0.0014 |
| GK0667 | 5 | unknown conserved protein | 0.0056 | BC1085 | -0.0153 | BH3002 | -0.0032 | YHFI | -0.0161 | OB1173 | 0.0022 |
| GK0682 | 3.3 | ATP-dependent deoxyribonuclease subunit A | 0.0251 | BC1138 | 0.0294 | BH2980 | 0.0109 | ADDA | 0.0152 | OB1182 | -0.0008 |
| GK0695 | 5 | unknown conserved protein | -0.0486 | BC1146 | -0.0220 | BH1743 | 0.0010 | YISI | 0.0133 | OB1347 | -0.0104 |
| GK0696 | 5 | unknown conserved protein | 0.0330 | BC1147 | 0.0619 | BH2000 | 0.0257 | YISK | 0.0242 | OB2444 | 0.0221 |
| GK0700 | 2.2 | asparagine synthetase (glutamine-hydrolyzing) (EC 6.3.5.4) | 0.0243 | BC1697 | -0.0124 | BH1508 | 0.0187 | YISO | 0.0112 | OB2608 | 0.0088 |
| GK0703 | 2.1.1 | alpha-cyclodextrinase | 0.0037 | BC4014 | -0.0027 | BH2927 | -0.0110 | YVDP | -0.0104 | OB2561 | -0.0058 |
| GK0731 | 2.1.1 | alcohol dehydrogenase (EC 1.1.1.1) | 0.0454 | BC2220 | 0.0401 | BH0538 | 0.0566 | ADHA | 0.0213 | OB0786 | 0.0331 |
| GK0747 | 5 | unknown conserved protein | 0.0237 | BC1165 | 0.0014 | BH2906 | 0.0046 | YITU | 0.0116 | OB1194 | 0.0028 |
| GK0753 | 5 | unknown conserved protein | 0.0175 | BC5035 | 0.0290 | BH2173 | 0.0281 | YITW | 0.0458 | OB1196 | 0.0463 |
| GK0791 | 2.2 | arginine biosynthesis bifunctional enzyme | 0.0016 | BC4129 | 0.0054 | BH2899 | 0.0129 | ARGJ | 0.0131 | OB1076 | -0.0243 |
| GK0792 | 2.2 | acetylglutamate kinase (EC 2.7.2.8) | 0.0314 | BC4128 | 0.0311 | BH2898 | 0.0402 | ARGB | 0.0262 | OB1077 | 0.0310 |
| GK0793 | 2.2 | N-acetylornithine aminotransferase (EC 2.6.1.11) | -0.0059 | BC4127 | 0.0250 | BH2897 | -0.0089 | ARGD | -0.0131 | OB1078 | -0.0121 |
| GK0796 | 2.2 | ornithine carbamoyltransferase (EC 2.1.3.3) | 0.0037 | BC4126 | 0.0164 | BH2894 | -0.0068 | ARGF | 0.0023 | OB0460 | -0.0033 |
| GK0798 | 5 | unknown conserved protein | 0.0108 | BC1167 | 0.0016 | BH2893 | 0.0549 | YIZC | -0.0128 | OB2291 | 0.0369 |
| GK0804 | 2.4 | 3-oxoacyl-[acyl-carrier protein] synthase (EC 2.3.1.41) | 0.0303 | BC1173 | 0.0233 | BH2883 | 0.0299 | YJAX | 0.0398 | OB1204 | 0.0171 |
| GK0805 | 2.4 | 3-oxoacyl-[acyl-carrier protein] synthase (EC 2.3.1.41) | 0.0213 | BC1174 | 0.0267 | BH2882 | 0.0183 | YJAY | 0.0211 | OB1205 | 0.0008 |
| GK0808 | 5 | unknown conserved protein | 0.0110 | BC1176 | 0.0203 | BH2872 | 0.0184 | YJBA | 0.0429 | OB1207 | 0.0124 |
| GK0817 | 5 | unknown conserved protein | 0.0233 | BC1184 | 0.0161 | BH2861 | 0.0287 | YJBD | 0.0158 | OB1213 | 0.0003 |
| GK0819 | 1.10 | negative regulator of genetic competence | 0.0462 | BC1190 | 0.0651 | BH2852 | 0.0503 | MECA | 0.0477 | OB1214 | 0.0468 |
| GK0821 | 5 | unknown conserved protein | -0.0027 | BC1192 | -0.0071 | BH2857 | -0.0493 | YJBF | -0.0178 | OB1215 | -0.0386 |
| GK0822 | 2.2 | thimet oligoendopeptidase (EC 3.4.24.15) | 0.0175 | BC1193 | 0.0121 | BH2856 | 0.0021 | YJBG | 0.0141 | OB1216 | -0.0006 |
| GK0824 | 5 | unknown conserved protein | 0.0101 | BC1194 | 0.0144 | BH2855 | 0.0151 | YJBH | 0.0121 | OB1217 | 0.0047 |
| GK0825 | 5 | unknown conserved protein | 0.0107 | BC1195 | 0.0016 | BH2854 | 0.0064 | YJBI | -0.0010 | OB1218 | 0.0266 |
| GK0827 | 5 | unknown conserved protein | 0.0284 | BC1196 | 0.0080 | BH2851 | -0.0067 | YJBK | -0.0052 | OB1219 | -0.0245 |
| GK0829 | 5 | unknown conserved protein | 0.0295 | BC1198 | 0.0309 | BH2849 | 0.0216 | YJBM | 0.0328 | OB1220 | 0.0419 |
| GK0830 | 2.5 | inorganic polyphosphate/ATP-NAD kinase (EC 2.7.1.23) | 0.0131 | BC1199 | 0.0206 | BH2848 | 0.0085 | YJBN | 0.0153 | OB1221 | 0.0154 |
| GK0831 | 5 | unknown conserved protein | 0.0035 | BC1200 | 0.0130 | BH2847 | 0.0087 | YJBO | 0.0032 | OB1222 | -0.0158 |
| GK0832 | 2.3 | diadenosine tetraphosphatase | 0.0402 | BC1202 | 0.0222 | BH2845 | 0.0421 | YJBP | 0.0501 | OB1223 | 0.0207 |
| GK0834 | 2.4 | enoyl-[acyl-carrier-protein] reductase [NADH] (EC 1.3.1.9) | 0.0218 | BC1216 | 0.0178 | BH2843 | 0.0164 | YJBW | 0.0096 | OB0223 | 0.0257 |
| GK0862 | 5 | unknown conserved protein | -0.0173 | BC1506 | -0.0097 | BH1641 | -0.0456 | YJCG | 0.0045 | OB1795 | -0.0461 |
| GK0863 | 5 | unknown conserved protein | 0.0390 | BC1224 | 0.0361 | BH1438 | 0.0560 | YJCF | 0.0660 | OB1229 | 0.0341 |
| GK0864 | 5 | unknown conserved protein | 0.0267 | BC1225 | 0.0009 | BH1439 | 0.0104 | YJCG | 0.0053 | OB1230 | -0.0058 |
| GK0865 | 5 | unknown conserved protein | 0.0144 | BC1226 | 0.0161 | BH1440 | 0.0063 | YJCH | 0.0078 | OB1231 | -0.0071 |
| GK0901 | 5 | unknown conserved protein | 0.0396 | BC3732 | 0.0403 | BH0558 | 0.0341 | YVGZ | -0.0047 | OB1141 | 0.0236 |
| GK0903 | 1.2 | mercuric ion-binding protein | 0.0490 | BC3731 | 0.0387 | BH0556 | 0.0510 | YVGY | 0.0474 | OB1143 | 0.0280 |
| GK0913 | 5 | unknown conserved protein | -0.0138 | BC4564 | -0.0052 | BH2866 | -0.0059 | YUEL | 0.0018 | OB0529 | 0.0064 |
| GK0951 | 5 | unknown conserved protein | 0.0063 | BC4034 | 0.0576 | BH1047 | 0.0381 | YKRU | 0.0195 | OB3111 | 0.0249 |
| GK0952 | 2.2 | aspartate aminotransferase (EC 2.6.1.-) | 0.0238 | BC4035 | -0.0029 | BH1060 | 0.0263 | YKRV | 0.0119 | OB0420 | -0.0176 |
| GK0964 | 5 | unknown conserved protein | 0.0350 | BC1977 | 0.0153 | BH2157 | 0.0218 | YUAI | 0.0265 | OB1271 | 0.0239 |
| GK0975 | 4.2 | aluminum resistance protein | 0.0169 | BC1341 | 0.0074 | BH2244 | 0.0200 | YKVI | 0.0158 | OB0312 | 0.0256 |
| GK0977 | 2.5 | coenzyme PQQ synthesis | 0.0038 | BC1343 | -0.0008 | BH2242 | 0.0071 | YKVL | -0.0105 | OB2803 | 0.0000 |
| GK0978 | 5 | unknown conserved protein | 0.0169 | BC1344 | 0.0029 | BH2241 | 0.0247 | YKVM | 0.0185 | OB2210 | 0.0009 |
| GK0990 | 3.5.2 | transcription antiterminator | 0.0213 | BC4051 | 0.0090 | BH0845 | 0.0226 | GLCT | 0.0042 | OB1883 | 0.0039 |
| GK0995 | 2.1.1 | phosphocarrier protein (Histidine-containing protein) | 0.0042 | BC4049 | -0.0098 | BH3074 | 0.0546 | PTSH | 0.0037 | OB2344 | 0.0463 |
| GK0996 | 1.2 | phosphoenolpyruvate-protein phosphotransferase (EC 2.7.3.9) | 0.0280 | BC4048 | 0.0256 | BH3073 | 0.0332 | PTSI | 0.0391 | OB2432 | 0.0272 |
| GK1023 | 2.1.3 | 2-oxoglutarate dehydrogenase complex E1 component (EC 1.2.4.2) | 0.0158 | BC1252 | -0.0050 | BH2206 | 0.0096 | ODHA | 0.0046 | OB1089 | 0.0157 |
| GK1024 | 2.1.3 | 2-oxoglutarate dehydrogenase complex E2 component (dihydrolipoamide transsuccinylase) (EC 2.3.1.61) | 0.0176 | BC1251 | 0.0246 | BH2205 | 0.0446 | ODHB | 0.0262 | OB1090 | 0.0417 |
| GK1045 | 5 | unknown conserved protein | -0.0037 | BC3989 | -0.0142 | BH2277 | 0.0033 | YKUI | 0.0005 | OB2252 | -0.0176 |
| GK1048 | 5 | unknown conserved protein | 0.0161 | BC3983 | 0.0188 | BH1482 | -0.0165 | YKUL | 0.0140 | OB1401 | 0.0170 |
| GK1049 | 2.2 | tetrahydrodipicolinate succinylase (EC 2.3.1.117) | 0.0553 | BC3981 | 0.0687 | BH2669 | 0.0525 | YKUQ | 0.0592 | OB1402 | 0.0387 |
| GK1050 | 2.2 | hippurate hydrolase | 0.0138 | BC3980 | 0.0339 | BH2668 | 0.0197 | YKUR | 0.0147 | OB1403 | -0.0051 |
| GK1052 | 1.2 | potassium transport system NAD-binding component | 0.0354 | BC3978 | 0.0297 | BH2663 | 0.0338 | YKQB | 0.0362 | OB1407 | 0.0353 |
| GK1053 | 5 | unknown conserved protein | 0.0275 | BC3977 | 0.0164 | BH2662 | 0.0176 | YKQC | 0.0181 | OB1408 | 0.0171 |
| GK1054 | 5 | unknown conserved protein | 0.0666 | BC3976 | 0.0538 | BH2661 | 0.0397 | YKZG | 0.0818 | OB1409 | 0.0504 |
| GK1056 | 5 | unknown conserved protein | 0.0367 | BC3975 | 0.0237 | BH2659 | 0.0211 | YKRA | 0.0341 | OB2658 | 0.0064 |

Fig. 10 E

| Gene | Val1 | Description | V1 | Col1 | V2 | Col2 | V3 | Col3 | V4 | Col4 | V5 |
|---|---|---|---|---|---|---|---|---|---|---|---|
| GK1057 | 3.8 | peptide deformylase 2 (PDF 2) N-formylmethionylaminoacyl-tRNA deformylase (EC 3.5.1.88) | 0.0151 | BC3974 | 0.0337 | BH2658 | 0.0424 | YKRB | 0.0365 | OB1410 | 0.0142 |
| GK1058 | 2.1.2 | dehydrogenase E1 component, alpha subunit (lipoamide) (EC 1.2.4.1) | 0.0198 | BC3973 | 0.0063 | BH2655 | 0.0154 | PDHA | 0.0133 | OB1412 | 0.0055 |
| GK1059 | 2.1.2 | dehydrogenase E1 component, beta subunit (lipoamide) (EC 1.2.4.1) | 0.0396 | BC3972 | 0.0393 | BH2654 | 0.0455 | PDHB | 0.0355 | OB1413 | 0.0407 |
| GK1060 | 2.1.2 | dihydrolipoamide acetyltransferase component of pyruvate dehydrogenase complex (E2)(EC 2.3.1.12) | 0.0491 | BC3971 | 0.0415 | BH2653 | 0.0640 | PDHC | 0.0269 | OB1414 | 0.0385 |
| GK1061 | 2.1.2 | dihydrolipoamide dehydrogenase (E3 component of pyruvate complex) (EC 1.8.1.4) | 0.0387 | BC3970 | 0.0435 | BH2652 | 0.0457 | PDHD | 0.0450 | OB1415 | 0.0439 |
| GK1067 | 5 | unknown conserved protein | 0.0530 | BC3959 | 0.0524 | BH2636 | 0.0355 | YKZI | 0.0775 | OB1421 | 0.0629 |
| GK1068 | 2.1.1 | myo-inositol-1(or 4)-monophosphatase (Inositol-1-phosphatase) (I-1-Pase) | 0.0282 | BC3958 | 0.0317 | BH2635 | 0.0030 | YKTC | 0.0261 | OB1422 | 0.0067 |
| GK1070 | 3.7.4 | GTP-binding elongation factor EF-G | 0.0460 | BC3956 | 0.0363 | BH2633 | 0.0382 | YLAG | 0.0353 | OB0586 | 0.0424 |
| GK1076 | 5 | unknown conserved protein | 0.0454 | BC3950 | 0.0112 | BH2628 | 0.0094 | YLAL | 0.0094 | OB1427 | 0.0390 |
| GK1077 | 5 | unknown conserved protein | 0.0244 | BC3949 | -0.0072 | BH2626 | 0.0248 | YLAN | 0.0145 | OB1428 | 0.0084 |
| GK1079 | 2.1.2 | pyruvate carboxylase (EC 6.4.1.1) | 0.0383 | BC3947 | 0.0272 | BH2625 | 0.0255 | PYCA | 0.0231 | OB1430 | 0.0192 |
| GK1082 | 1.4 | cytochrome c oxidase subunit II | 0.0096 | BC3944 | -0.0031 | BH2615 | 0.0198 | CTAC | 0.0167 | OB1437 | 0.0213 |
| GK1085 | 1.4 | cytochrome c oxidase subunit IV | -0.0065 | BC3941 | -0.0230 | BH2612 | -0.0432 | CTAF | -0.0108 | OB1440 | -0.0132 |
| GK1089 | 5 | unknown conserved protein | 0.0372 | BC3938 | 0.0248 | BH2606 | 0.0449 | YLBA | 0.0305 | OB1444 | 0.0362 |
| GK1091 | 5 | unknown conserved protein | -0.0029 | BC3937 | -0.0025 | BH2604 | 0.0403 | YLBC | 0.0180 | OB1445 | 0.0161 |
| GK1092 | 5 | unknown conserved protein | -0.0022 | BC3936 | -0.0229 | BH2601 | 0.0026 | YLBD | -0.0334 | OB1446 | -0.0147 |
| GK1093 | 5 | unknown conserved protein | -0.0390 | BC3935 | -0.0005 | BH2600 | 0.0115 | YLBE | -0.0153 | OB1447 | -0.0008 |
| GK1095 | 5 | unknown conserved protein | 0.0569 | BC3933 | 0.0260 | BH2596 | 0.0024 | YLBF | 0.0369 | OB1448 | 0.0067 |
| GK1096 | 5 | unknown conserved protein | 0.0283 | BC3932 | 0.0083 | BH2594 | -0.0082 | YLBG | 0.0342 | OB1449 | 0.0188 |
| GK1098 | 5 | unknown conserved protein | 0.0467 | BC3930 | 0.0303 | BH2590 | 0.0392 | YLBH | 0.0320 | OB1450 | 0.0108 |
| GK1099 | 1.1 | lipopolysaccharide core biosynthesis (Pantetheine-phosphate adenylyltransferase) (Dephospho-CoA pyrophosphorylase) | 0.0141 | BC3929 | 0.0203 | BH2589 | 0.0091 | YLBI | 0.0122 | OB1451 | 0.0030 |
| GK1102 | 5 | unknown conserved protein | 0.0365 | BC3926 | 0.0398 | BH2586 | 0.0535 | YLBL | 0.0230 | OB1453 | 0.0368 |
| GK1104 | 5 | unknown conserved protein | 0.0306 | BC3924 | 0.0317 | BH2584 | 0.0328 | YLBN | 0.0240 | OB1455 | 0.0485 |
| GK1110 | 5 | unknown conserved protein | 0.0203 | BC3919 | 0.0196 | BH2577 | 0.0123 | YLLA | -0.0011 | OB1460 | 0.0023 |
| GK1111 | 5 | unknown conserved protein | 0.0302 | BC3918 | 0.0231 | BH2575 | 0.0299 | YLXA | 0.0192 | OB1462 | 0.0093 |
| GK1112 | 1.7 | cell division protein | 0.0089 | BC3917 | 0.0102 | BH2574 | -0.0067 | FTSL | -0.0111 | OB1463 | -0.0085 |
| GK1114 | 1.1 | penicillin-binding protein (sporulation specific penicillin-binding protein) | 0.0279 | BC3915 | 0.0300 | BH2572 | 0.0268 | SPOVD | 0.0254 | OB1465 | 0.0235 |
| GK1115 | 1.1 | UDP-N-acetylmuramoylalanine-D-glutamate-2,6- diaminopimelate ligase (EC 6.3.2.13) | 0.0156 | BC3914 | 0.0141 | BH2571 | 0.0202 | MURE | 0.0095 | OB1466 | 0.0022 |
| GK1118 | 1.1 | UDP-N-acetylmuramoylalanine D-glutamate ligase (D-glutamic acid adding enzyme) (EC 6.3.2.9) | 0.0053 | BC3912 | 0.0068 | BH2567 | 0.0247 | MURD | 0.0034 | OB1469 | -0.0080 |
| GK1120 | 1.7 | cell-division initiation protein (septum formation) | 0.0303 | BC3908 | 0.0246 | BH2563 | 0.0314 | DIVIB | 0.0078 | OB1471 | 0.0149 |
| GK1124 | 1.7 | cell division protein (septum formation) | 0.0305 | BC3907 | 0.0199 | BH2559 | 0.0526 | FTSA | 0.0178 | OB1472 | 0.0260 |
| GK1125 | 1.7 | cell-division initiation protein (septum formation) | 0.0190 | BC3906 | 0.0082 | BH2558 | 0.0145 | FTSZ | 0.0071 | OB1473 | 0.0099 |
| GK1127 | 3.5.1 | RNA polymerase sigma-E factor precursor (Sigma-29) (Stage II sporulation protein GB) | 0.0196 | BC3904 | 0.0211 | BH2556 | 0.0263 | SIGE | 0.0266 | OB1475 | 0.0264 |
| GK1128 | 3.5.1 | RNA polymerase sporulation-specific sigma factor (sigma-G) | 0.0316 | BC3903 | 0.0252 | BH2554 | 0.0058 | SIGG | 0.0173 | OB1476 | 0.0119 |
| GK1130 | 5 | unknown conserved protein | 0.0130 | BC3901 | 0.0078 | BH2551 | -0.0096 | YLMD | -0.0211 | OB1478 | -0.0031 |
| GK1131 | 5 | unknown conserved protein | 0.0344 | BC3900 | 0.0410 | BH2550 | 0.0350 | YLME | 0.0113 | OB1479 | 0.0188 |
| GK1132 | 5 | unknown conserved protein | 0.0395 | BC3899 | 0.0176 | BH2549 | 0.0245 | YLMF | 0.0250 | OB1480 | 0.0233 |
| GK1133 | 5 | unknown conserved protein | -0.0125 | BC3898 | -0.0056 | BH2548 | -0.0172 | YLMG | -0.0083 | OB1481 | -0.0031 |
| GK1134 | 5 | unknown conserved protein | 0.0440 | BC3897 | 0.0255 | BH2547 | 0.0401 | YLMH | 0.0044 | OB1482 | 0.0147 |
| GK1135 | 1.7 | cell-division initiation protein (septum placement) | 0.0535 | BC3896 | 0.0575 | BH2546 | 0.0547 | DIVIVA | 0.0448 | OB1483 | 0.0543 |
| GK1146 | 5 | unknown conserved protein | 0.0370 | BC3892 | 0.0322 | BH2542 | 0.0183 | YLSB | 0.0002 | OB1486 | 0.0095 |
| GK1147 | 3.5.2 | pyrimidine operon regulatory protein; uracil phosphoribosyltransferase (EC 2.4.2.9) | 0.0561 | BC3891 | 0.0369 | BH2541 | 0.0402 | PYRR | 0.0340 | OB1487 | 0.0309 |
| GK1149 | 2.3 | Aspartate carbamoyltransferase (EC 2.1.3.2) | 0.0365 | BC3889 | 0.0382 | BH2539 | 0.0145 | PYRB | 0.0082 | OB1488 | -0.0017 |
| GK1150 | 2.3 | dihydroorotase (EC 3.5.2.3) | 0.0288 | BC3888 | 0.0303 | BH2538 | 0.0355 | PYRC | 0.0166 | OB1489 | 0.0188 |
| GK1151 | 2.3 | carbamoyl-phosphate synthase (glutamine-hydrolyzing) (EC 6.3.5.5) | 0.0286 | BC3887 | 0.0205 | BH2537 | 0.0156 | PYRAA | 0.0214 | OB1490 | 0.0084 |
| GK1153 | 2.3 | dihydroorotate dehydrogenase electron transfer subunit | 0.0259 | BC3885 | 0.0350 | BH2535 | 0.0262 | PYRDII | 0.0300 | OB1492 | 0.0249 |
| GK1154 | 2.3 | dihydroorotate dehydrogenase, catalytic subunit (Dihydroorotate oxidase) (EC 1.3.3.1) | 0.0210 | BC3884 | 0.0098 | BH2534 | 0.0122 | PYRD | 0.0087 | OB1493 | 0.0157 |
| GK1155 | 2.3 | orotidine-5'-phosphate decarboxylase (EC 4.1.1.23) | 0.0183 | BC3883 | 0.0444 | BH2533 | 0.0158 | PYRF | 0.0144 | OB1494 | -0.0022 |
| GK1157 | 2.3 | orotate phosphoribosyltransferase (EC 2.4.2.10) | 0.0100 | BC3882 | 0.0261 | BH2532 | -0.0044 | PYRE | -0.0029 | OB1495 | -0.0087 |
| GK1163 | 4.1 | fibronectin/fibrinogen-binding protein | 0.0114 | BC3873 | 0.0044 | BH2516 | 0.0021 | YLOA | 0.0042 | OB1499 | -0.0172 |
| GK1167 | 2.3 | Guanylate kinase (EC 2.7.4.8) | 0.0879 | BC3869 | 0.0912 | BH2512 | 0.0894 | YLOD | 0.0320 | OB1502 | 0.0516 |
| GK1168 | 3.5.1 | DNA-directed RNA polymerase omega subunit(Transcriptase omega chain) | 0.0749 | BC3868 | 0.0236 | BH2511 | 0.0433 | YLOH | 0.0221 | OB1503 | 0.0012 |
| GK1169 | 2.5 | pantothenate metabolism flavoprotein | 0.0331 | BC3867 | 0.0157 | DFP | 0.0148 | YLOI | 0.0084 | OB1504 | -0.0105 |
| GK1170 | 3.1 | primosomal replication factor Y (primosomal protein N') | 0.0269 | BC3866 | 0.0209 | BH2509 | 0.0239 | PRIA | 0.0169 | OB1505 | 0.0010 |
| GK1172 | 3.7.3 | methionyl-tRNA formyltransferase | 0.0268 | BC3864 | 0.0649 | BH2508 | 0.0201 | FMT | 0.0427 | OB1506 | 0.0225 |
| GK1173 | 3.6 | RNA-binding Sun protein | 0.0260 | BC3863 | 0.0297 | BH2507 | 0.0243 | YLOM | 0.0137 | OB1507 | 0.0032 |
| GK1174 | 5 | unknown conserved protein | 0.0100 | BC3862 | 0.0100 | BH2506 | 0.0181 | YLON | 0.0182 | OB3097 | 0.0003 |
| GK1175 | 3.8 | serine/threonine phosphatase | 0.0030 | BC3861 | 0.0071 | BH2505 | 0.0043 | YLOO | 0.0107 | OB1508 | 0.0111 |
| GK1176 | 3.8 | serine/threonine-protein kinase (EC 2.7.1.-) | 0.0417 | BC3860 | 0.0279 | BH2504 | 0.0260 | YLOP | 0.0364 | OB1509 | 0.0379 |
| GK1177 | 5 | unknown conserved protein | 0.0496 | BC3859 | 0.0385 | BH2503 | 0.0260 | YLOQ | 0.0224 | OB1510 | 0.0311 |

Fig. 10 F

| GK# | EC | Description | val | BC# | val | BH# | val | Name | val | OB# | val |
|---|---|---|---|---|---|---|---|---|---|---|---|
| GK1178 | 2.1.1 | ribulose-phosphate 3-epimerase (EC 5.1.3.1) | 0.0418 | BC3858 | 0.0395 | BH2502 | 0.0251 | YLOR | 0.0369 | OB1511 | 0.0287 |
| GK1181 | 3.7.1 | 50S ribosomal protein L28 | -0.0004 | BC3856 | 0.0171 | BH2500 | 0.0289 | RPMB | 0.0093 | OB1514 | 0.0126 |
| GK1182 | 5 | unknown conserved protein | 0.0359 | BC3855 | 0.0303 | BH2499 | 0.0498 | YLOU | 0.0249 | OB1515 | 0.0000 |
| GK1183 | 5 | unknown conserved protein | 0.0282 | BC3854 | 0.0286 | BH2498 | 0.0192 | YLOV | 0.0081 | OB1516 | 0.0287 |
| GK1184 | 2.2 | L-serine dehydratase (L-serine deaminase) (EC 4.3.1.17) beta chain | 0.0286 | BC4136 | 0.0428 | BH2497 | 0.0389 | YLOW | 0.0321 | OB1518 | 0.0124 |
| GK1185 | 2.2 | L-serine dehydratase (L-serine deaminase) (EC 4.3.1.17) alpha chain | 0.0318 | BC4135 | 0.0179 | BH2496 | 0.0218 | YLPA | 0.0071 | OB1519 | 0.0220 |
| GK1186 | 3.3 | ATP-dependent DNA helicase (EC 3.6.1.-) | 0.0281 | BC3853 | 0.0252 | BH2495 | 0.0147 | YLPB | 0.0118 | OB1520 | 0.0147 |
| GK1187 | 5 | unknown conserved protein | 0.0458 | BC3852 | 0.0536 | BH2494 | 0.0233 | YLPC | 0.0319 | OB1521 | 0.0354 |
| GK1188 | 2.4 | fatty acid/phospholipid biosynthesis | 0.0267 | BC3851 | 0.0230 | BH2493 | 0.0228 | PLSX | 0.0148 | OB1522 | 0.0170 |
| GK1189 | 2.4 | malonyl CoA-acyl carrier protein transacylase (EC 2.3.1.39) | 0.0179 | BC3850 | 0.0159 | BH2492 | 0.0335 | FABD | 0.0283 | OB1523 | 0.0041 |
| GK1190 | 2.4 | 3-ketoacyl-acyl carrier protein reductase (EC 1.1.1.100) | 0.0246 | BC3849 | 0.0094 | BH2491 | 0.0224 | FABG | 0.0033 | OB1524 | 0.0018 |
| GK1191 | 2.4 | acyl carrier protein | 0.0795 | BC3848 | 0.0944 | BH2490 | 0.1035 | ACPA | 0.0665 | OB1525 | 0.0935 |
| GK1192 | 3.6 | dsRNA-specific ribonuclease (EC 3.1.26.3) | 0.0066 | BC3847 | 0.0261 | BH2489 | -0.0139 | RNCS | 0.0163 | OB1526 | 0.0050 |
| GK1193 | 3.4 | chromosome segregation ATPases (SMC) | 0.0283 | BC3846 | 0.0291 | BH2487 | 0.0266 | SMC | 0.0205 | OB1528 | 0.0108 |
| GK1194 | 1.6 | signal recognition particle GTPase (docking protein) | 0.0375 | BC3845 | 0.0418 | BH2486 | 0.0466 | FTSY | 0.0377 | OB1529 | 0.0321 |
| GK1195 | 5 | unknown conserved protein | 0.0272 | BC3844 | 0.0242 | BH2485 | 0.0094 | YLXM | 0.0243 | OB1530 | 0.0059 |
| GK1196 | 1.6 | signal recognition particle GTPase | 0.0265 | BC3843 | 0.0194 | BH2484 | 0.0193 | FFH | 0.0202 | OB1531 | 0.0108 |
| GK1197 | 3.7.1 | 30S ribosomal protein S16 | 0.0240 | BC3842 | 0.0253 | BH2483 | 0.0297 | RPSP | 0.0208 | OB1532 | 0.0344 |
| GK1198 | 3.6 | RNA-binding protein | 0.0865 | BC3841 | 0.0677 | BH2482 | 0.0262 | YLQC | 0.0123 | OB1533 | 0.0722 |
| GK1200 | 3.6 | 16S rRNA processing protein | 0.0928 | BC3840 | 0.0612 | BH2480 | 0.0559 | YLQE | 0.0926 | OB1535 | 0.0550 |
| GK1201 | 3.6 | tRNA (guanine-N(1)-)-methyltransferase (M1G-methyltransferase) (EC 2.1.1.31) | 0.0313 | BC3839 | 0.0410 | BH2479 | 0.0112 | TRMD | 0.0276 | OB1536 | 0.0105 |
| GK1202 | 3.7.1 | 50S ribosomal protein L19 | 0.0428 | BC3838 | 0.0673 | BH2478 | 0.0719 | RPLS | 0.0875 | OB1537 | 0.0521 |
| GK1204 | 5 | unknown conserved protein | 0.0199 | BC3836 | 0.0384 | BH2476 | 0.0125 | YLQF | 0.0221 | OB1539 | 0.0175 |
| GK1205 | 3.1 | ribonuclease HII (EC 3.1.26.4) | 0.0311 | BC3835 | 0.0293 | BH2475 | 0.0065 | RNH | 0.0253 | OB1540 | -0.0088 |
| GK1208 | 2.1.3 | succinyl-CoA synthetase (EC 6.2.1.5) beta subunit (succinate-CoA ligase beta subunit) | 0.0511 | BC3834 | 0.0542 | BH2470 | 0.0515 | SUCC | 0.0475 | OB1543 | 0.0524 |
| GK1209 | 2.1.3 | succinyl-CoA synthetase (EC 6.2.1.5) alpha subunit | 0.0641 | BC3833 | 0.0539 | BH2469 | 0.0503 | SUCD | 0.0523 | OB1544 | 0.0554 |
| GK1210 | 1.10 | DNA processing protein (Smf family) | -0.0130 | BC3832 | 0.0140 | BH2468 | -0.0185 | SMF | -0.0115 | OB1545 | -0.0313 |
| GK1211 | 3.4 | DNA topoisomerase I (EC 5.99.1.2) (omega-protein) (relaxing enzyme) (untwisting enzyme) | 0.0399 | BC3831 | 0.0393 | BH2467 | 0.0414 | TOPA | 0.0335 | OB1546 | 0.0293 |
| GK1212 | 4.4 | integrase/recombinase | -0.0070 | BC3829 | -0.0068 | BH2465 | -0.0136 | CODV | -0.0070 | OB1548 | -0.0017 |
| GK1213 | 4.1 | proteasome protease subunit | 0.0146 | BC3828 | 0.0085 | BH2464 | 0.0235 | CLPQ | 0.0173 | OB1549 | 0.0033 |
| GK1214 | 4.1 | ATP-dependent protease ATPase subunit | 0.0272 | BC3827 | 0.0283 | BH2463 | 0.0347 | CLPY | 0.0374 | OB1550 | 0.0354 |
| GK1215 | 3.5.2 | transcription pleiotropic repressor | 0.0445 | BC3826 | 0.0242 | BH2462 | 0.0347 | CODY | 0.0183 | OB1551 | 0.0430 |
| GK1216 | 1.5 | flagellar basal-body rod protein | -0.0262 | BC1641 | -0.0738 | BH2461 | -0.0584 | FLGB | -0.0550 | OB1552 | -0.0735 |
| GK1217 | 1.5 | flagellar basal-body rod protein | 0.0094 | BC1642 | -0.0090 | BH2460 | -0.0041 | FLGC | -0.0213 | OB1553 | -0.0429 |
| GK1219 | 1.5 | flagellar basal-body M-ring protein | 0.0070 | BC1644 | 0.0288 | BH2458 | 0.0265 | FLIF | 0.0069 | OB1555 | 0.0153 |
| GK1220 | 1.5 | flagellar motor switch protein | 0.0282 | BC1645 | 0.0452 | BH2457 | 0.0192 | FLIG | 0.0309 | OB1556 | 0.0195 |
| GK1222 | 1.5 | flagellar-specific ATP synthase | 0.0246 | BC1647 | 0.0435 | BH2455 | 0.0186 | FLII | 0.0179 | OB1558 | 0.0267 |
| GK1226 | 1.5 | flagellar hook capping protein | -0.0533 | BC1650 | -0.0401 | BH2451 | -0.0300 | YLXG | -0.0419 | OB1562 | -0.0019 |
| GK1230 | 1.5 | flagellar motor switch protein | 0.0289 | BC1662 | 0.0258 | BH2446 | 0.0122 | FLIM | 0.0200 | OB1567 | 0.0059 |
| GK1231 | 1.5 | flagellar motor switch protein | 0.0074 | BC1663 | 0.0499 | BH2445 | 0.0034 | FLIY | 0.0177 | OB1568 | 0.0080 |
| GK1235 | 1.5 | flagellar protein required for flagellar formation | -0.0274 | BC1666 | -0.0238 | BH2441 | -0.0356 | FLIQ | -0.0450 | OB1572 | -0.0416 |
| GK1242 | 1.3 | two-component sensor histidine kinase (chemotaxis protein) | 0.0269 | BC1628 | 0.0265 | BH2970 | 0.0313 | CHEA | 0.0277 | OB2543 | 0.0284 |
| GK1249 | 3.7.1 | 30S ribosomal protein S2 | 0.0528 | BC3825 | 0.0376 | BH2427 | 0.0555 | RPSB | 0.0388 | OB1586 | 0.0509 |
| GK1250 | 3.7.4 | translation elongation factor Ts (EF-Ts) | 0.0382 | BC3824 | 0.0469 | BH2426 | 0.0615 | TSF | 0.0347 | OB1587 | 0.0658 |
| GK1251 | 2.3 | uridylate kinase (EC 2.7.4.-) | 0.0288 | BC3823 | 0.0341 | BH2425 | 0.0321 | SMBA | 0.0324 | OB1588 | 0.0296 |
| GK1252 | 3.7.5 | ribosome recycling factor | 0.0406 | BC3822 | 0.0531 | BH2424 | 0.0313 | FRR | 0.0463 | OB1589 | -0.0079 |
| GK1253 | 2.4 | undecaprenyl pyrophosphate synthetase (UPP synthetase) (EC 2.5.1.31) | 0.0143 | BC3821 | 0.0304 | BH2423 | 0.0179 | YLUA | 0.0115 | OB1590 | 0.0066 |
| GK1258 | 3.1 | DNA-directed DNA polymerase III (EC 2.7.7.7) alpha chain | 0.0241 | BC3816 | 0.0192 | BH2418 | 0.0215 | POLC | 0.0144 | OB1593 | 0.0119 |
| GK1259 | 5 | unknown conserved protein | 0.0634 | BC3815 | 0.0568 | BH2417 | 0.0770 | YLXS | 0.0488 | OB1594 | 0.0807 |
| GK1260 | 3.5.4 | transcription termination-antitermination factor | 0.0381 | BC3814 | 0.0455 | BH2416 | 0.0530 | NUSA | 0.0578 | OB1595 | 0.0577 |
| GK1261 | 5 | unknown conserved protein | 0.0494 | BC3813 | 0.0436 | BH2415 | 0.0240 | YLXR | 0.0280 | OB1596 | 0.0678 |
| GK1262 | 3.7.1 | ribosomal protein (L7AE family) | 0.0296 | BC3812 | 0.0280 | BH2414 | 0.0084 | YLXQ | 0.0303 | OB1597 | 0.0016 |
| GK1263 | 3.7.3 | translation initiation factor IF-2 | 0.0454 | BC3811 | 0.0464 | BH2413 | 0.0446 | INFB | 0.0396 | OB1598 | 0.0234 |
| GK1264 | 5 | unknown conserved protein | 0.0025 | BC3810 | 0.0387 | BH2412 | 0.0152 | YLXP | 0.0146 | OB1599 | -0.0075 |
| GK1265 | 3.7.2 | ribosome-binding factor A | 0.0288 | BC3809 | 0.0549 | BH2411 | 0.0405 | RBFA | 0.0638 | OB1600 | 0.0433 |
| GK1266 | 3.6 | tRNA pseudouridine 5S synthase | 0.0411 | BC3808 | 0.0508 | BH2410 | 0.0371 | TRUB | 0.0273 | OB1601 | 0.0276 |
| GK1267 | 2.5 | riboflavin kinase (EC 2.7.1.26) (flavokinase); FAD synthetase (EC 2.7.7.2) (FAD pyrophosphorylase) | 0.0310 | BC3807 | 0.0363 | BH2409 | 0.0224 | RIBC | 0.0226 | OB1602 | 0.0169 |
| GK1268 | 3.7.1 | 30S ribosomal protein S15 | 0.0251 | BC3806 | -0.0091 | BH2408 | -0.0052 | RPSO | -0.0151 | OB1603 | 0.0384 |
| GK1269 | 2.3 | polyribonucleotide nucleotidyltransferase (polynucleotide phosphorylase) (EC 2.7.7.8) | 0.0586 | BC3805 | 0.0425 | BH2407 | 0.0397 | PNPA | 0.0457 | OB1604 | 0.0420 |
| GK1270 | 2.1.1 | deacetylase | 0.0212 | BC3804 | 0.0143 | BH2406 | 0.0211 | YLXY | 0.0018 | OB1605 | 0.0164 |
| GK1271 | 3.8 | processing protease | 0.0101 | BC3803 | 0.0100 | BH2405 | -0.0014 | YMXG | 0.0083 | OB1606 | -0.0065 |
| GK1272 | 5 | unknown conserved protein | 0.0631 | BC3802 | 0.0529 | BH2404 | 0.0543 | YMXH | 0.0268 | OB1607 | 0.0613 |
| GK1273 | 1.8 | dipicolinate synthase subunit A | 0.0138 | BC3801 | 0.0106 | BH2403 | 0.0179 | SPOVFA | -0.0079 | OB1608 | -0.0020 |
| GK1274 | 1.8 | dipicolinate synthase subunit B | 0.0046 | BC3800 | 0.0193 | BH2402 | -0.0011 | SPOVFB | -0.0086 | OB1609 | -0.0200 |
| GK1275 | 2.2 | aspartate-semialdehyde dehydrogenase (EC 1.2.1.11) | 0.0220 | BC3799 | 0.0265 | BH2401 | 0.0269 | ASD | 0.0023 | OB1610 | 0.0135 |
| GK1276 | 2.2 | aspartate kinase I (EC 2.7.2.4) | 0.0208 | BC3798 | 0.0297 | BH2400 | 0.0204 | DAPG | 0.0133 | OB1611 | 0.0126 |
| GK1279 | 5 | unknown conserved protein | 0.0262 | BC3795 | 0.0289 | BH2397 | 0.0098 | YMFB | 0.0195 | OB1612 | 0.0012 |
| GK1282 | 3.5.2 | transcriptional regulator (GntR family) | 0.0059 | BC3792 | 0.0263 | BH2394 | 0.0331 | YMFC | 0.0052 | OB1615 | 0.0185 |
| GK1288 | 5 | unknown conserved protein | 0.0163 | BC3786 | 0.0010 | BH2392 | 0.0170 | YMFH | 0.0194 | OB1617 | -0.0112 |

Fig. 10 G

| GK# | | Description | | | | | | | | | |
|---|---|---|---|---|---|---|---|---|---|---|---|
| GK1289 | 2.4 | 3-oxoacyl- acyl-carrier protein reductase | 0.0226 | BC3785 | 0.0236 | BH2391 | 0.0029 | YMFI | -0.0268 | OB1618 | -0.0079 |
| GK1290 | 5 | unknown conserved protein | -0.0294 | BC3784 | 0.0026 | BH2390 | 0.0137 | YMFJ | -0.0224 | OB1619 | -0.0256 |
| GK1292 | 5 | unknown conserved protein | 0.0098 | BC3782 | 0.0290 | BH2388 | 0.0470 | YMFM | -0.0158 | OB1621 | 0.0296 |
| GK1294 | 1.10 | competence-damaged protein | 0.0111 | BC3780 | 0.0207 | BH2385 | 0.0034 | CINA | 0.0241 | OB1623 | -0.0013 |
| GK1295 | 6 | unknown | 0.0135 | BC3779 | 0.0262 | BH2383 | 0.0340 | RECA | 0.0246 | OB1624 | 0.0265 |
| GK1297 | 5 | unknown conserved protein | 0.0595 | BC3778 | 0.0594 | BH2378 | 0.0691 | YMDA | 0.0533 | OB1625 | 0.0581 |
| GK1298 | 5 | unknown conserved protein | 0.0304 | BC3777 | 0.0188 | BH2376 | 0.0267 | YMDB | 0.0216 | OB1626 | 0.0176 |
| GK1299 | 1.8 | stage V sporulation protein S | 0.0283 | BC3776 | 0.0368 | BH2375 | 0.0375 | SPOVS | 0.0258 | OB1627 | 0.0192 |
| GK1303 | 5 | unknown conserved protein | 0.0427 | BC3772 | 0.0371 | BH2372 | 0.0379 | YMCB | 0.0437 | OB1628 | 0.0374 |
| GK1304 | 5 | unknown conserved protein | -0.0111 | BC3771 | 0.0110 | BH2371 | 0.0228 | YMCA | -0.0104 | OB1629 | 0.0356 |
| GK1305 | 1.8 | outer spore coat protein | 0.0537 | BC3770 | 0.0700 | BH2370 | 0.0439 | COTE | 0.0887 | OB1630 | 0.0367 |
| GK1306 | 3.2 | DNA mismatch repair protein | 0.0221 | BC3769 | 0.0221 | BH2369 | 0.0242 | MUTS | 0.0206 | OB1631 | 0.0060 |
| GK1307 | 3.2 | DNA mismatch repair protein | 0.0273 | BC3768 | 0.0203 | BH2368 | 0.0193 | MUTL | 0.0228 | OB1632 | 0.0094 |
| GK1312 | 3.6 | tRNA delta(2)-isopentenylpyrophosphate transferase (IPP transferase) | 0.0223 | BC3714 | 0.0407 | BH2366 | 0.0296 | MIAA | -0.0111 | OB1634 | 0.0161 |
| GK1313 | 4.4 | host factor-1 protein | -0.0449 | BC3713 | -0.0530 | BH2365 | -0.0361 | YMAH | -0.0481 | OB1635 | -0.0674 |
| GK1325 | 4.2 | aluminum resistance protein | 0.0269 | BC3702 | 0.0194 | BH2361 | 0.0209 | YNBB | 0.0162 | OB1649 | 0.0037 |
| GK1328 | 3.5.2 | transcription repressor of SOS regulon | 0.0430 | BC3690 | 0.0327 | BH2356 | 0.0357 | LEXA | 0.0436 | OB1669 | 0.0459 |
| GK1330 | 4.5 | resolvase | 0.0499 | BC3689 | 0.0398 | BH2354 | 0.0070 | YNEB | 0.0523 | OB1670 | 0.0166 |
| GK1331 | 5 | unknown conserved protein | 0.0021 | BC3688 | 0.0254 | BH2353 | -0.0094 | YNZC | 0.0191 | OB1671 | 0.0168 |
| GK1332 | 2.1.2 | transketolase (EC 2.2.1.1) | 0.0134 | BC3682 | 0.0071 | BH2352 | 0.0105 | TKT | 0.0153 | OB1672 | 0.0209 |
| GK1333 | 5 | unknown conserved protein | 0.0003 | BC3681 | 0.0131 | BH2351 | -0.0112 | YNEE | 0.0078 | OB1673 | -0.0225 |
| GK1334 | 5 | unknown conserved protein | -0.0323 | BC3680 | -0.0463 | BH2350 | -0.0634 | YNEF | -0.0291 | OB1676 | -0.0432 |
| GK1342 | 5 | unknown conserved protein | 0.0236 | BC3660 | 0.0041 | BH2332 | 0.0239 | YNEK | 0.0079 | OB1679 | 0.0205 |
| GK1347 | 2.1.3 | aconitate hydratase (citrate hydro-lyase) (aconitase) (EC 4.2.1.3) | 0.0341 | BC3616 | 0.0213 | BH2299 | 0.0269 | CITB | 0.0267 | OB1681 | 0.0173 |
| GK1349 | 5 | unknown conserved protein | 0.0046 | BC3558 | 0.0192 | BH3402 | -0.0005 | YUID | -0.0169 | OB2347 | -0.0308 |
| GK1360 | 2.1.1 | glycerol kinase (ATP:glycerol 3-phosphotransferase) (EC 2.7.1.30) | 0.0078 | BC1035 | 0.0161 | BH1093 | 0.0084 | GLPK | 0.0068 | OB2475 | 0.0128 |
| GK1410 | 2.7 | sulfite reductase (EC 1.8.1.2) hemoprotein beta-component | 0.0369 | BC1424 | 0.0192 | BH0610 | 0.0283 | YVGQ | 0.0234 | OB1654 | 0.0242 |
| GK1427 | 2.5 | adenosylmethionine-8-amino-7-oxononanoate aminotransferase | 0.0143 | BC1610 | 0.0210 | BH1035 | -0.0190 | YHXA | 0.0040 | OB0490 | 0.0008 |
| GK1431 | 2.2 | glutamate synthase large subunit (EC 1.4.1.13) | 0.0230 | BC0511 | 0.0002 | BH1728 | 0.0183 | GLTA | 0.0103 | OB3099 | 0.0090 |
| GK1442 | 5 | unknown conserved protein | -0.0369 | BC1295 | -0.0338 | BH1803 | -0.0226 | YKWD | -0.0348 | OB0867 | -0.0422 |
| GK1461 | 1.2 | iron(III) dicitrate ABC transporter (ATP-binding protein) | 0.0008 | BC0619 | -0.0130 | BH1039 | 0.0066 | YUSV | 0.0025 | OB0450 | -0.0175 |
| GK1498 | 5 | unknown conserved protein | 0.0469 | BC2069 | 0.0342 | BH1582 | 0.0223 | YHDJ | 0.0000 | OB0311 | 0.0156 |
| GK1502 | 4.2 | lactam utilization protein | 0.0194 | BC3066 | 0.0003 | BH1821 | 0.0000 | YCSF | -0.0026 | OB2677 | -0.0053 |
| GK1509 | 2.5 | hydroxyethylthiazole kinase (EC 2.7.1.50) | 0.0292 | BC0419 | 0.0376 | BH3349 | 0.0234 | THIK | -0.0013 | OB0473 | -0.0113 |
| GK1510 | 2.5 | phosphomethylpyrimidine kinase (EC 2.7.4.7) | 0.0187 | BC0751 | 0.0147 | BH1435 | -0.0079 | YJBV | -0.0114 | OB0474 | -0.0017 |
| GK1511 | 2.5 | thiamine-phosphate diphosphorylase (EC 2.5.1.3) | 0.0396 | BC0420 | 0.0478 | BH1431 | 0.0465 | THIC | 0.0300 | OB0472 | -0.0245 |
| GK1525 | 2.2 | cysteine synthase (EC 4.2.99.8) | 0.0257 | BC1763 | 0.0188 | BH3271 | 0.0288 | YTKP | 0.0180 | OB1703 | 0.0179 |
| GK1541 | 5 | unknown conserved protein | 0.0037 | BC1562 | 0.0017 | BH1769 | 0.0143 | YPSB | 0.0082 | OB1750 | 0.0098 |
| GK1543 | 5 | unknown conserved protein | 0.0221 | BC1563 | 0.0256 | BH1771 | 0.0314 | YPSC | 0.0203 | OB1749 | 0.0017 |
| GK1544 | 3.2 | ATP-dependent helicase | 0.0215 | BC1565 | 0.0240 | BH1792 | 0.0210 | YPVA | 0.0228 | OB3114 | 0.0078 |
| GK1553 | 5 | unknown conserved protein | 0.0089 | BC1572 | 0.0171 | BH1700 | -0.0097 | YPDB | 0.0047 | OB1700 | -0.0160 |
| GK1561 | 1.8 | thithioredoxin-like protein | 0.0447 | BC3608 | 0.0040 | BH2287 | 0.0188 | TLP | -0.0139 | OB0182 | 0.0180 |
| GK1562 | 5 | unknown conserved protein | 0.0656 | BC3606 | 0.0623 | BH2288 | 0.0552 | YNEP | 0.0294 | OB1684 | 0.0601 |
| GK1599 | 2.5 | biotin carboxylase (EC 6.3.4.14) | 0.0349 | BC2484 | 0.0268 | BH1132 | 0.0352 | YNGH | 0.0223 | OB1696 | 0.0217 |
| GK1601 | 2.4 | hydroxymethylglutaryl-CoA lyase | 0.0184 | BC2486 | -0.0052 | BH1134 | 0.0180 | YNGG | -0.0039 | OB1343 | 0.0039 |
| GK1602 | 2.4 | enoyl-CoA hydratase | 0.0210 | BC2487 | 0.0182 | BH1135 | 0.0371 | YNGF | 0.0039 | OB1698 | -0.0001 |
| GK1603 | 2.1.1 | propionyl-CoA carboxylase | 0.0355 | BC2488 | 0.0231 | BH1136 | 0.0293 | YNGE | 0.0184 | OB1699 | 0.0247 |
| GK1652 | 1.4 | nitro/flavin reductase (EC 1.19.6.-) | 0.0027 | BC1619 | 0.0323 | BH1048 | -0.0017 | YWCG | -0.0114 | OB1385 | -0.0443 |
| GK1676 | 4.2 | nitric oxide synthase | 0.0080 | BC5444 | 0.0134 | BH0823 | 0.0211 | YFLM | -0.0256 | OB2691 | -0.0039 |
| GK1737 | 1.4 | flavohemoglobin | 0.0107 | BC1448 | 0.0223 | BH1058 | 0.0079 | HMP | 0.0014 | OB0291 | 0.0092 |
| GK1750 | 3.4 | DNA topoisomerase IV (EC 5.99.1.-) subunit A | 0.0396 | BC3596 | 0.0345 | BH2139 | 0.0195 | GRLA | 0.0231 | OB1694 | 0.0242 |
| GK1751 | 3.4 | DNA topoisomerase IV (EC 5.99.1.-) subunit B | 0.0373 | BC3597 | 0.0421 | BH2140 | 0.0390 | GRLB | 0.0359 | OB1693 | 0.0328 |
| GK1752 | 5 | unknown conserved protein | 0.0702 | BC3599 | 0.0622 | BH2141 | 0.0282 | YNET | 0.0302 | OB1692 | -0.0021 |
| GK1775 | 2.5 | dihydrofolate reductase (EC 1.5.1.3) | 0.0461 | BC2192 | 0.0061 | BH3450 | 0.0502 | DFRA | 0.0053 | OB1739 | -0.0076 |
| GK1776 | 2.3 | thymidylate synthetase (EC 2.1.1.45) | -0.0019 | BC2191 | 0.0061 | BH3451 | 0.0076 | THYD | -0.0005 | OB1740 | -0.0282 |
| GK1778 | 5 | unknown conserved protein | 0.0146 | BC2186 | -0.0173 | BH1730 | 0.0064 | YPJP | -0.0119 | OB3160 | 0.0055 |
| GK1784 | 5 | unknown conserved protein | 0.0685 | BC2155 | 0.0519 | BH1718 | 0.0447 | YPGR | 0.0417 | OB0505 | 0.0192 |
| GK1785 | 4.1 | glutathione peroxidase | 0.0217 | BC2114 | 0.0314 | BH2830 | -0.0041 | BSAA | -0.0019 | OB0570 | -0.0100 |
| GK1787 | 2.2 | homoserine O-succinyltransferase (EC 2.3.1.46) | 0.0133 | BC5405 | 0.0176 | BH2280 | -0.0088 | METB | -0.0032 | OB0438 | -0.0098 |
| GK1817 | 6 | unknown | -0.0059 | BC2018 | -0.0124 | BH3927 | 0.0083 | YCSN | -0.0065 | OB2635 | -0.0074 |
| GK1820 | 2.5 | pyrazinamidase/nicotinamidase | 0.0381 | BC2213 | 0.0482 | BH3777 | 0.0097 | YUEJ | 0.0159 | OB0565 | 0.0158 |
| GK1839 | 2.1.1 | fructose-1-phosphate kinase (EC 2.7.1.56) | 0.0354 | BC3719 | 0.0394 | BH0827 | 0.0254 | FRUB | 0.0282 | OB0839 | -0.0175 |
| GK1840 | 3.5.2 | transcriptional regulator (DeoR family) | 0.0235 | BC3720 | -0.0053 | BH0826 | 0.0225 | FRUR | 0.0107 | OB0840 | -0.0137 |
| GK1872 | 2.1.1 | oxidoreductase | 0.0257 | BC1368 | 0.0383 | BH1205 | 0.0064 | YRPB | -0.0197 | OB0826 | -0.0159 |
| GK1906 | 2.1.1 | L-ribulose-5-phosphate 4-epimerase (phosphoribulose isomerase) (EC 5.1.3.4) | 0.0098 | BC0380 | 0.0314 | BH1871 | 0.0318 | ARAD | 0.0035 | OB2798 | 0.0333 |
| GK1921 | 2.1.1 | maltose transacetylase (maltose O-acetyltransferase) (EC 2.3.1.79) | 0.0566 | BC4658 | 0.0437 | BH3001 | 0.0527 | YYAI | 0.0255 | OB1064 | 0.0368 |
| GK2014 | 2.1.1 | glycolate oxidase subunit | 0.0228 | BC1297 | 0.0244 | BH2730 | 0.0371 | YSPC | 0.0247 | OB2831 | 0.0292 |
| GK2046 | 2.2 | dihydroxy-acid dehydratase (EC 4.2.1.9) | 0.0325 | BC1780 | 0.0376 | BH3062 | 0.0332 | ILVD | 0.0309 | OB2624 | 0.0170 |
| GK2048 | 2.2 | gamma-glutamyl kinase (glutamate 5-kinase) (EC 2.7.2.11) | -0.0028 | BC2975 | -0.0036 | BH1505 | -0.0149 | PROB | 0.0055 | OB1052 | -0.0115 |
| GK2049 | 2.2 | gamma-glutamyl phosphate reductase (glutamate-5-semialdehyde dehydrogenase) (EC 1.2.1.41) | 0.0126 | BC4365 | 0.0179 | BH1504 | 0.0086 | PROA | 0.0193 | OB1053 | 0.0071 |
| GK2056 | 2.2 | shikimate kinase (EC 2.7.1.71) | 0.0232 | BC4232 | 0.0528 | BH0500 | 0.0376 | AROI | 0.0255 | OB2455 | 0.0369 |
| GK2140 | 2.2 | leucyl aminopeptidase II (EC 3.4.11.1) | 0.0022 | BC0360 | 0.0210 | BH2245 | 0.0161 | AMPS | 0.0195 | OB3042 | 0.0117 |
| GK2153 | 2.1.1 | glycerol-3-phosphate dehydrogenase (EC 1.1.99.5) | 0.0391 | BC1036 | 0.0390 | BH1095 | 0.0293 | GLPD | 0.0342 | OB2471 | 0.0231 |

Fig. 10 H

| Gene | Code | Description | Val1 | Ref1 | Val2 | Ref2 | Val3 | Ref3 | Val4 | Ref4 | Val5 |
|---|---|---|---|---|---|---|---|---|---|---|---|
| GK2154 | 3.5.2 | transcriptional antiterminator of glycerol uptake operon | 0.0116 | BC1033 | 0.0106 | BH1091 | -0.0025 | GLPP | 0.0039 | OB2477 | -0.0063 |
| GK2156 | 1.3 | two-component sensor histidine kinase | 0.0135 | BC3201 | -0.0148 | BH0373 | 0.0114 | YKOH | -0.0033 | OB0595 | -0.0064 |
| GK2157 | 3.5.2 | two-component response regulator | 0.0418 | BC3200 | 0.0170 | BH0372 | 0.0320 | YKOG | 0.0447 | OB0594 | 0.0279 |
| GK2165 | 5 | unknown conserved protein | 0.0359 | BC1557 | 0.0083 | BH1707 | 0.0334 | YPPB | 0.0421 | OB1752 | 0.0263 |
| GK2167 | 3.3 | recombination protein U (penicillin-binding protein related factor A) | 0.0074 | BC1554 | -0.0089 | BH1703 | 0.0063 | YPPB | -0.0154 | OB1755 | -0.0389 |
| GK2169 | 3.2 | endonuclease III (DNA-(apurinic or apyrimidinic site) lyase) | 0.0232 | BC1548 | 0.0245 | BH1698 | 0.0086 | NTH | 0.0296 | OB1757 | 0.0164 |
| GK2170 | 3.1 | chromosome replication initiation protein | 0.0214 | BC1547 | -0.0116 | BH1697 | 0.0031 | DNAD | -0.0231 | OB1758 | -0.0055 |
| GK2171 | 3.7.2 | asparaginyl-tRNA synthetase (EC 6.1.1.22) | 0.0309 | BC4559 | 0.0298 | BH1696 | 0.0218 | ASNS | 0.0347 | OB1759 | 0.0250 |
| GK2172 | 2.2 | aspartate transaminase (transaminase A) (EC 2.6.1.1) | 0.0190 | BC1546 | 0.0053 | BH1695 | 0.0214 | ASPB | 0.0240 | OB1760 | -0.0001 |
| GK2173 | 5 | unknown conserved protein | 0.0327 | BC1545 | 0.0759 | BH1694 | 0.0663 | YFMB | 0.0460 | OB1761 | -0.0169 |
| GK2177 | 2.5 | aspartate 1-decarboxylase precursor (aspartate alpha-decarboxylase) (EC 4.1.1.11) | 0.0417 | BC1542 | 0.0361 | BH1689 | 0.0378 | PAND | 0.0081 | OB1763 | -0.0003 |
| GK2178 | 2.5 | pantothenate synthetase (pantoate--beta-alanine ligase) (EC 6.3.2.1) | 0.0243 | BC1541 | 0.0391 | BH1688 | 0.0394 | PANC | 0.0342 | OB3275 | 0.0056 |
| GK2179 | 2.5 | ketopantoate hydroxymethyltransferase (3-methyl-2-oxobutanoate hydroxymethyltransferase) (EC 2.1.2.11) | 0.0269 | BC1540 | 0.0375 | BH1687 | 0.0172 | PANB | 0.0295 | OB3274 | 0.0291 |
| GK2180 | 3.5.2 | biotin [acetyl-CoA carboxylase] synthetase (EC 6.3.4.15); transcriptional repressor of the biotin operon | 0.0138 | BC1537 | 0.0238 | BH1685 | 0.0087 | BIRA | 0.0111 | OB1764 | -0.0238 |
| GK2181 | 3.6 | tRNA nucleotidyltransferase (EC 2.7.7.19) | 0.0394 | BC1536 | 0.0384 | BH1684 | 0.0169 | PAPS | 0.0091 | OB1765 | -0.0062 |
| GK2182 | 5 | unknown conserved protein | 0.0336 | BC1535 | 0.0228 | BH1683 | 0.0363 | YPJH | 0.0215 | OB1766 | 0.0042 |
| GK2184 | 2.1.1 | methylglyoxal synthase (EC 4.2.99.11) | 0.0116 | BC1533 | -0.0070 | BH1681 | 0.0211 | YPJF | -0.0128 | OB1767 | -0.0123 |
| GK2185 | 2.2 | dihydrodipicolinate reductase | 0.0285 | BC1532 | 0.0229 | BH1680 | 0.0322 | DAPB | 0.0149 | OB1768 | 0.0063 |
| GK2186 | 5 | unknown conserved protein | 0.0336 | BC1531 | 0.0639 | BH1679 | 0.0413 | YPJD | 0.0610 | OB1769 | 0.0225 |
| GK2192 | 1.4 | menaquinol-cytochrome-c reductase (EC 1.10.2.-) iron-sulfur subunit (Rieske iron-sulfur protein) | 0.0352 | BC1522 | 0.0209 | BH1672 | -0.0063 | QCRA | 0.0095 | OB1776 | 0.0176 |
| GK2193 | 5 | unknown conserved protein | 0.0466 | BC1521 | 0.0272 | BH1671 | -0.0092 | YPIF | 0.0095 | OB1777 | 0.0002 |
| GK2194 | 5 | unknown conserved protein | 0.0037 | BC1520 | -0.0051 | BH1670 | 0.0047 | YPIB | -0.0186 | OB1778 | -0.0247 |
| GK2195 | 5 | unknown conserved protein | 0.0431 | BC1519 | 0.0340 | BH1669 | 0.0163 | YPIA | 0.0267 | OB1779 | 0.0330 |
| GK2197 | 2.2 | prephenate dehydrogenase (EC 1.3.1.12) | 0.0177 | BC2939 | 0.0278 | BH1666 | 0.0262 | TYRA | 0.0098 | OB1781 | -0.0067 |
| GK2198 | 2.2 | histidinol-phosphate aminotransferase (imidazole acetol-phosphate transaminase) (EC 2.6.1.9); tyrosine/phenylalanine aminotransferase (EC 2.6.1.5) | 0.0230 | BC1518 | 0.0164 | BH1665 | 0.0170 | HISC | -0.0056 | OB1782 | -0.0093 |
| GK2199 | 2.2 | tryptophan synthase (EC 4.2.1.20) alpha chain | 0.0212 | BC1238 | 0.0755 | BH1664 | 0.0299 | TRPA | 0.0141 | OB0521 | 0.0215 |
| GK2200 | 2.2 | tryptophan synthase (EC 4.2.1.20) beta chain | 0.0313 | BC1237 | 0.0365 | BH1663 | 0.0239 | TRPB | 0.0261 | OB0522 | 0.0202 |
| GK2201 | 2.2 | phosphoribosyl anthranilate isomerase (EC 5.3.1.24) | 0.0301 | BC1236 | 0.0446 | BH1662 | 0.0096 | TRPF | 0.0010 | OB0523 | -0.0222 |
| GK2202 | 2.2 | indole-3-glycerol-phosphate synthase (EC 4.1.1.48) | 0.0451 | BC1235 | 0.0322 | BH1661 | 0.0253 | TRPC | 0.0210 | OB0524 | -0.0227 |
| GK2203 | 2.2 | anthranilate phosphoribosyltransferase (EC 2.4.2.18) | 0.0160 | BC1234 | 0.0137 | BH1660 | -0.0045 | TRPD | -0.0026 | OB0525 | -0.0045 |
| GK2204 | 2.2 | anthranilate synthase (EC 4.1.3.27) component I | 0.0334 | BC1232 | 0.0463 | BH1659 | 0.0368 | TRPE | 0.0166 | OB0527 | 0.0035 |
| GK2206 | 2.2 | 3-dehydroquinate synthase (EC 4.2.3.4) | 0.0289 | BC1517 | 0.0097 | BH1657 | 0.0293 | AROB | 0.0050 | OB1784 | -0.0047 |
| GK2208 | 1.5 | chemotactic methyltransferase (EC 2.1.1.-) | 0.0245 | BC1632 | -0.0259 | BH1655 | 0.0149 | CHER | -0.0053 | OB1786 | -0.0239 |
| GK2209 | 2.3 | nucleoside-diphosphate kinase (EC 2.7.4.6) | 0.0302 | BC1515 | 0.0570 | BH1654 | 0.0509 | NDK | 0.0374 | OB1787 | 0.0409 |
| GK2210 | 2.5 | heptaprenyl diphosphate synthase component II (spore germination protein C3) | 0.0029 | BC1514 | -0.0010 | BH1653 | -0.0069 | GERCC | 0.0043 | OB1788 | -0.0100 |
| GK2211 | 2.5 | 2-heptaprenyl-1,4-naphthoquinone methyltransferase (menaquinone biosynthesis methyltransferase) | 0.0350 | BC1513 | 0.0149 | BH1649 | 0.0208 | GERCB | 0.0158 | OB1789 | 0.0087 |
| GK2212 | 2.5 | heptaprenyl diphosphate synthase component I (spore germination protein C1) | 0.0021 | BC1512 | 0.0115 | BH1648 | 0.0093 | GERCA | -0.0138 | OB1790 | -0.0397 |
| GK2215 | 3.4 | DNA-binding protein HU (DNA-binding protein II) | 0.0406 | BC1510 | 0.0180 | BH1309 | 0.0307 | HBS | 0.0297 | OB1792 | 0.0451 |
| GK2217 | 1.8 | stage IV sporulation protein A (spore cortex formation and coat assembly) | 0.0528 | BC1509 | 0.0478 | BH1645 | 0.0476 | SPOIVA | 0.0483 | OB1793 | 0.0458 |
| GK2218 | 5 | unknown conserved protein | -0.0056 | BC1508 | 0.0167 | BH1644 | 0.0020 | YPHF | -0.0019 | OB1794 | 0.0103 |
| GK2220 | 2.1.1 | NAD(P)H-dependent glycerol-3-phosphate dehydrogenase (EC 1.1.1.8) | 0.0344 | BC1505 | 0.0399 | BH1640 | 0.0203 | GPSA | 0.0241 | OB1796 | 0.0183 |
| GK2221 | 4.6 | GTP-binding protein | 0.0438 | BC1504 | 0.0373 | BH1638 | 0.0408 | YPHC | 0.0349 | OB1797 | 0.0308 |
| GK2225 | 3.7.1 | 30S ribosomal protein S1 | 0.0758 | BC1498 | 0.0663 | BH1636 | 0.0717 | YPFD | 0.0604 | OB1800 | 0.0480 |
| GK2226 | 2.4 | 1-acylglycerol-3-phosphate O-acyltransferase (EC 2.3.1.51) | 0.0368 | BC0228 | 0.0163 | BH1635 | 0.0408 | YHDO | 0.0064 | OB1801 | 0.0333 |
| GK2227 | 2.3 | cytidylate kinase (cytidine monophosphate kinase) | 0.0567 | BC1497 | 0.0428 | BH1634 | 0.0107 | CMK | 0.0523 | OB1802 | 0.0216 |
| GK2230 | 1.8 | sporulation protein | 0.0103 | BC2752 | 0.0113 | BH1632 | 0.0313 | YPEB | 0.0024 | OB1805 | 0.0080 |
| GK2231 | 1.9 | sporulation specific N-acetylmuramoyl-L-alanine amidase (spore cortex-lytic enzyme) (EC 3.5.1.28) | -0.0115 | BC2753 | -0.0217 | BH1631 | 0.0074 | SLEB | -0.0257 | OB1806 | -0.0209 |
| GK2233 | 2.2 | L-asparaginase (L-asparagine amidohydrolase) (EC 3.5.1.1) | 0.0397 | BC1496 | 0.0142 | BH1624 | 0.0141 | YCCC | -0.0069 | OB1808 | 0.0084 |
| GK2234 | 1.4 | thioredoxin reductase | 0.0430 | BC1495 | 0.0394 | BH1623 | 0.0420 | YPDA | 0.0476 | OB1809 | 0.0166 |
| GK2236 | 1.10 | negative regulator of competence | 0.0299 | BC1490 | 0.0196 | BH1620 | 0.0302 | YPBH | 0.0019 | OB1811 | 0.0284 |
| GK2243 | 3.3 | ATP-dependent DNA helicase | 0.0141 | BC1485 | 0.0144 | BH1607 | -0.0097 | RECQ | -0.0099 | OB1814 | -0.0171 |
| GK2244 | 5 | unknown conserved protein | -0.0107 | BC1484 | 0.0060 | BH1606 | -0.0133 | YPBB | -0.0325 | OB1815 | -0.0364 |
| GK2247 | 2.2 | phosphoglycerate dehydrogenase (EC 1.1.1.95) | 0.0160 | BC3248 | 0.0197 | BH1602 | 0.0238 | SERA | 0.0208 | OB2626 | 0.0198 |
| GK2257 | 5 | unknown conserved protein | 0.0247 | BC1479 | 0.0583 | BH1595 | 0.0430 | YVQK | 0.0281 | OB0904 | 0.0077 |
| GK2275 | 3.5.2 | transcriptional regulator (GntR family) | 0.0601 | BC4053 | 0.0184 | BH0419 | 0.0148 | YVOA | -0.0166 | OB0612 | -0.0146 |

Fig. 10 I

| Gene | EC | Description | | | | | | | | | | | |
|---|---|---|---|---|---|---|---|---|---|---|---|---|---|
| GK2277 | 2.1.1 | N-acetylglucosamine-6-phosphate deacetylase (EC 3.5.1.25) | 0.0270 | BC4055 | 0.0332 | BH0421 | 0.0053 | NAGA | -0.0015 | OB2907 | 0.0258 | | |
| GK2278 | 1.3 | two-component sensor histidine kinase | 0.0192 | BC1478 | 0.0179 | BH1581 | 0.0135 | RESE | 0.0018 | OB1818 | 0.0147 | | |
| GK2279 | 3.5.2 | two-component response regulator | 0.0541 | BC1477 | 0.0476 | BH1580 | 0.0332 | RESD | 0.0439 | OB1819 | 0.0569 | | |
| GK2282 | 1.4 | thioredoxin (cytochrome c biogenesis) | 0.0234 | BC1473 | 0.0407 | BH1577 | 0.0590 | RPSA | 0.0170 | OB1822 | 0.0081 | | |
| GK2283 | 3.6 | ribosomal large subunit pseudouridine synthase B (pseudouridylate synthase) (uracil hydrolyase) (EC 4.2.1.70) | 0.0651 | BC1472 | 0.0463 | BH1576 | 0.0507 | YPUL | 0.0481 | OB1823 | 0.0333 | | |
| GK2286 | 1.1 | D-alanyl-D-alanine carboxypeptidase (EC 3.4.16.4) | 0.0223 | BC1469 | 0.0132 | BH1573 | 0.0103 | DACB | 0.0021 | OB1826 | -0.0057 | | |
| GK2290 | 5 | unknown conserved protein | 0.0414 | BC4057 | 0.0196 | BH1561 | 0.0179 | YPUH | 0.0376 | OB1827 | 0.0263 | | |
| GK2291 | 5 | unknown conserved protein | 0.0092 | BC4058 | 0.0065 | BH1560 | 0.0248 | YPUG | 0.0378 | OB1828 | 0.0207 | | |
| GK2293 | 5 | unknown conserved protein | -0.0027 | BC4060 | 0.0133 | BH1558 | 0.0447 | RIBT | -0.0184 | OB1830 | 0.0104 | | |
| GK2294 | 2.5 | riboflavin synthase beta subunit (EC 2.5.1.9) | 0.0253 | BC4112 | 0.0401 | BH1557 | 0.0404 | RIBH | 0.0190 | OB3213 | 0.0279 | | |
| GK2296 | 2.5 | riboflavin synthase alpha subunit (EC 2.5.1.9) | 0.0396 | BC4110 | -0.0083 | BH1555 | 0.0186 | RIBB | 0.0082 | OB3215 | -0.0220 | | |
| GK2298 | 3.8 | peptidyl-prolyl cis-trans isomerase (rotamase) (EC 5.2.1.8) | 0.0326 | BC4061 | 0.0438 | BH1545 | 0.0565 | PPIB | 0.0359 | OB1832 | 0.0229 | | |
| GK2299 | 5 | unknown conserved protein | -0.0306 | BC4062 | -0.0092 | BH1404 | 0.0163 | YPUA | -0.0001 | OB3057 | 0.0195 | | |
| GK2300 | 2.2 | diaminopimelate decarboxylase (EC 4.1.1.20) | 0.0328 | BC1419 | 0.0206 | BH1544 | 0.0264 | LYSA | 0.0285 | OB1833 | 0.0045 | | |
| GK2308 | 3.5.1 | RNA polymerase sporulation-specific sigma factor (sigma-F) (Stage II sporulation protein AC) | 0.0246 | BC4072 | 0.0215 | BH1538 | 0.0167 | SIGF | 0.0227 | OB1839 | 0.0122 | | |
| GK2309 | 1.8 | anti-sigma F factor (serine kinase) (stage II sporulation factor AB) | 0.0409 | BC4073 | 0.0156 | BH1537 | 0.0200 | SPOIIAB | 0.0211 | OB1840 | 0.0418 | | |
| GK2310 | 1.8 | anti-sigma F factor antagonist (stage II sporulation protein AA) | 0.0120 | BC4074 | 0.0441 | BH1536 | 0.0145 | SPOIIAA | -0.0066 | OB1841 | 0.0328 | | |
| GK2311 | 1.1 | D-alanyl-D-alanine carboxypeptidase (penicillin binding protein) (EC 3.4.16.4) | 0.0258 | BC4075 | 0.0209 | BH1535 | 0.0255 | DACF | 0.0166 | OB1842 | 0.0108 | | |
| GK2314 | 2.3 | phosphopentomutase (EC 5.4.2.7) | 0.0368 | BC4087 | 0.0288 | BH1530 | 0.0314 | DRM | 0.0230 | OB1846 | 0.0165 | | |
| GK2315 | 4.4 | integrase/recombinase | -0.0007 | BC4089 | 0.0059 | BH1529 | -0.0152 | RIPX | -0.0045 | OB1847 | -0.0250 | | |
| GK2317 | 3.5.2 | transcriptional regulator (Fur family) (ferric uptake regulator) | 0.0563 | BC4091 | 0.0444 | BH1527 | 0.0486 | YQKL | 0.0604 | OB1849 | 0.0491 | | |
| GK2320 | 2.1.1 | ADP-ribose pyrophosphatase (EC 3.6.1.13) | 0.0593 | BC4094 | 0.0727 | BH1524 | 0.0528 | YQKG | 0.0837 | OB1851 | 0.0347 | | |
| GK2321 | 5 | unknown conserved protein | 0.0189 | BC4096 | 0.0121 | BH1011 | 0.0193 | YQKF | 0.0132 | OB1852 | -0.0004 | | |
| GK2331 | 2.2 | pyrroline-5-carboxylate reductase (EC 1.5.1.2) | 0.0170 | BC4134 | -0.0052 | BH1503 | 0.0045 | YQJO | 0.0131 | OB0013 | -0.0026 | | |
| GK2332 | 1.4 | NADH-dependent flavin oxidoreductase | 0.0239 | BC2023 | -0.0101 | BH1481 | 0.0097 | YQJM | 0.0140 | OB0028 | 0.0363 | | |
| GK2333 | 5 | unknown conserved protein | 0.0203 | BC4138 | 0.0210 | BH1713 | 0.0033 | YQJK | 0.0297 | OB1856 | -0.0057 | | |
| GK2342 | 1.2 | ABC transporter (ATP-binding protein) | -0.0005 | BC4831 | -0.0055 | BH3913 | -0.0056 | YTSC | -0.0200 | OB0833 | -0.0248 | | |
| GK2347 | 2.2 | tripeptidase | 0.0534 | BC4143 | 0.0508 | BH1469 | 0.0375 | YQJE | 0.0520 | OB1859 | 0.0430 | | |
| GK2350 | 2.1.3 | lactoylglutathione lyase (EC 4.4.1.5) | 0.0777 | BC1837 | 0.0512 | BH1468 | 0.0506 | YQJC | -0.0126 | OB1861 | 0.0014 | | |
| GK2368 | 5 | unknown conserved protein | 0.0310 | BC4151 | 0.0488 | BH2759 | 0.0447 | YQIW | 0.0438 | OB1863 | 0.0107 | | |
| GK2376 | 2.4 | branched-chain alpha-keto acid dehydrogenase E2 subunit (lipoamide acyltransferase) (EC 2.3.1.-) | 0.0169 | BC4157 | 0.0398 | BH2761 | 0.0216 | BFMBB | 0.0168 | OB1864 | 0.0200 | | |
| GK2377 | 2.4 | branched-chain alpha-keto acid dehydrogenase E1 component beta chain (2-oxoisovalerate dehydrogenase beta subunit) (EC 1.2.4.4) | 0.0448 | BC4158 | 0.0351 | BH2762 | 0.0346 | BFMBAI | 0.0441 | OB1865 | 0.0432 | | |
| GK2378 | 2.4 | branched-chain alpha-keto acid dehydrogenase E1 component alpha chain (2-oxoisovalerate dehydrogenase alpha subunit) (EC 1.2.4.4) | 0.0285 | BC4159 | 0.0341 | BH2763 | 0.0297 | BFMBAA | 0.0139 | OB1866 | 0.0192 | | |
| GK2379 | 2.4 | branched-chain alpha-keto acid dehydrogenase E3 component (dihydrolipoamide dehydrogenase) (EC 1.8.1.4) | 0.0410 | BC4160 | 0.0396 | BH2764 | 0.0409 | YQIV | 0.0313 | OB1867 | 0.0127 | | |
| GK2381 | 2.4 | leucine dehydrogenase (EC 1.4.1.9) | 0.0305 | BC4162 | 0.0355 | BH2765 | 0.0256 | YQIT | 0.0206 | OB1869 | 0.0195 | | |
| GK2383 | 3.5.2 | sigma L-dependent transcriptional regulator | 0.0365 | BC4165 | 0.0323 | BH2766 | 0.0228 | YQIR | 0.0278 | OB1870 | 0.0344 | | |
| GK2387 | 3.5.2 | stage 0 sporulation protein A (two-component response regulator) | 0.0096 | BC4170 | 0.0043 | BH2773 | 0.0023 | SPO0A | 0.0103 | OB1872 | 0.0099 | | |
| GK2388 | 1.8 | stage IV sporulation protein B | 0.0184 | BC4172 | 0.0066 | BH2775 | 0.0267 | SPOIVB | 0.0284 | OB1873 | 0.0419 | | |
| GK2390 | 3.5.2 | arginine repressor | -0.0060 | BC4174 | -0.0033 | BH2777 | -0.0027 | AHRC | -0.0060 | OB1875 | -0.0072 | | |
| GK2391 | 5 | unknown conserved protein | 0.0530 | BC4175 | 0.0461 | BH2778 | 0.0483 | YQXC | 0.0239 | OB1876 | 0.0260 | | |
| GK2393 | 2.4 | geranyltransferase (farnesyl-diphosphate synthase) (EC 2.5.1.10) | 0.0003 | BC4177 | 0.0218 | BH2781 | -0.0003 | YQIJ | 0.0161 | OB1877 | -0.0078 | | |
| GK2394 | 2.3 | exodeoxyribonuclease VII small subunit (exonuclease VII small subunit) (EC 3.1.11.6) | 0.0992 | BC4178 | 0.0538 | BH2782 | 0.0525 | YQIC | 0.0347 | OB1878 | 0.0291 | | |
| GK2395 | 2.3 | exodeoxyribonuclease VII large subunit (EC 3.1.11.6) | 0.0231 | BC4179 | 0.0126 | BH2783 | 0.0079 | YQIB | 0.0093 | OB1879 | -0.0175 | | |
| GK2396 | 2.5 | methylenetetrahydrofolate dehydrogenase (EC 1.5.1.5); methenyltetrahydrofolate cyclohydrolase (EC 3.5.4.9) | 0.0256 | BC4180 | 0.0580 | BH2784 | 0.0313 | FOLD | 0.0293 | OB1880 | 0.0102 | | |
| GK2397 | 3.5.4 | transcription termination factor | 0.0371 | BC4181 | 0.0676 | BH2785 | 0.0239 | YQHZ | 0.0094 | OB1881 | 0.0404 | | |
| GK2398 | 5 | unknown conserved protein | 0.0595 | BC4182 | 0.0748 | BH2786 | 0.0630 | YQHY | 0.0477 | OB1884 | 0.0430 | | |
| GK2399 | 2.4 | acetyl-CoA carboxylase subunit (biotin carboxylase subunit) (EC 6.4.1.2) | 0.0388 | BC4183 | 0.0411 | BH2787 | 0.0423 | ACCC | 0.0437 | OB1885 | 0.0323 | | |
| GK2400 | 2.4 | acetyl-CoA carboxylase subunit (biotin carboxyl carrier subunit) | 0.0440 | BC4184 | 0.0387 | BH2788 | 0.0475 | ACCB | 0.0211 | OB1886 | 0.0549 | | |
| GK2401 | 1.8 | stage III sporulation protein AH | 0.0209 | BC4186 | 0.0141 | BH2790 | 0.0354 | SPOIIIAH | 0.0281 | OB1887 | 0.0353 | | |
| GK2402 | 1.8 | stage III sporulation protein AG | 0.0510 | BC4187 | 0.0481 | BH2791 | 0.0361 | SPOIIIAG | 0.0296 | OB1888 | 0.0112 | | |
| GK2403 | 1.8 | stage III sporulation protein AF | 0.0218 | BC4188 | 0.0269 | BH2792 | 0.0094 | SPOIIIAF | 0.0205 | OB1889 | 0.0274 | | |
| GK2405 | 1.8 | stage III sporulation protein AD | -0.0147 | BC4190 | 0.0129 | BH2794 | -0.0082 | SPOIIIAD | 0.0081 | OB1891 | -0.0197 | | |
| GK2406 | 1.8 | stage III sporulation protein AC | 0.0096 | BC4191 | 0.0079 | BH2795 | 0.0180 | SPOIIIAC | 0.0117 | OB1892 | -0.0242 | | |
| GK2407 | 1.8 | stage III sporulation protein AB | -0.0246 | BC4192 | -0.0111 | BH2796 | 0.0057 | SPOIIIAB | -0.0461 | OB1893 | -0.0581 | | |
| GK2408 | 1.8 | stage III sporulation protein AA | 0.0483 | BC4193 | 0.0494 | BH2797 | 0.0456 | SPOIIIAA | 0.0192 | OB1894 | 0.0100 | | |
| GK2410 | 3.7.4 | translation elongation factor P | 0.0408 | BC4197 | 0.0395 | BH2799 | 0.0347 | EFP | 0.0255 | OB1895 | 0.0174 | | |
| GK2411 | 3.8 | Xaa-Pro dipeptidase | 0.0432 | BC4198 | 0.0413 | BH2800 | 0.0436 | YQHT | 0.0198 | OB1896 | 0.0277 | | |

Fig. 10 J

| Gene | Val1 | Description | V1 | Col1 | V2 | Col2 | V3 | Col3 | V4 | Col4 | V5 |
|---|---|---|---|---|---|---|---|---|---|---|---|
| GK2414 | 5 | unknown conserved protein | -0.0219 | BC4202 | -0.0474 | BH2804 | -0.0070 | YQHP | 0.0079 | OB1898 | -0.0307 |
| GK2415 | 5 | unknown conserved protein | 0.0186 | BC1989 | -0.0008 | BH2805 | -0.0012 | YQHO | 0.0147 | OB1899 | 0.0184 |
| GK2416 | 3.5.2 | transcriptional regulator (manganese transport regulator) | 0.0533 | BC4204 | 0.0520 | BH2807 | 0.0503 | YQHN | 0.0416 | OB1900 | 0.0490 |
| GK2420 | 2.4 | lipoate protein ligase | 0.0468 | BC4209 | 0.0374 | BH2812 | 0.0397 | YQHM | 0.0275 | OB1283 | -0.0039 |
| GK2421 | 5 | unknown conserved protein | 0.0183 | BC4210 | -0.0115 | BH2813 | 0.0062 | YQHL | 0.0075 | OB1901 | 0.0063 |
| GK2423 | 2.2 | glycine cleavage system P-protein, glycine dehydrogenase [decarboxylating] subunit 2 (Glycine decarboxylase) (EC 1.4.4.2) | 0.0203 | BC4224 | 0.0221 | BH2814 | 0.0249 | YQHK | 0.0266 | OB1902 | 0.0218 |
| GK2424 | 2.2 | glycine cleavage system P-protein, glycine dehydrogenase [decarboxylating] subunit 1 (Glycine decarboxylase) (EC 1.4.4.2) | 0.0199 | BC4225 | 0.0037 | BH2815 | 0.0078 | YQHJ | 0.0070 | OB1903 | 0.0070 |
| GK2425 | 2.2 | glycine cleavage system T protein, aminomethyltransferase (EC 2.1.2.10) | 0.0323 | BC4226 | 0.0511 | BH2816 | 0.0251 | YQHI | 0.0192 | OB1904 | 0.0273 |
| GK2426 | 3.3 | DNA/RNA helicases (SNF2 family) | 0.0234 | BC4227 | -0.0048 | BH2817 | 0.0080 | YQHH | 0.0045 | OB1905 | -0.0051 |
| GK2427 | 5 | unknown conserved protein | 0.0178 | BC4228 | -0.0132 | BH2818 | -0.0214 | YQHG | -0.0183 | OB1906 | -0.0026 |
| GK2432 | 5 | unknown conserved protein | -0.0008 | BC4236 | -0.0145 | BH2826 | -0.0065 | COMGH | -0.0088 | OB1911 | -0.0068 |
| GK2433 | 1.10 | DNA transport machinery (exogenous DNA-binding protein) | -0.0242 | BC4237 | -0.0124 | BH2827 | 0.0112 | COMGG | 0.0091 | OB1910 | 0.0099 |
| GK2435 | 1.10 | DNA transport machinery | 0.0013 | BC4239 | 0.0013 | BH2832 | -0.0335 | COMGA | -0.0049 | OB1908 | -0.0294 |
| GK2437 | 5 | unknown conserved protein | -0.0125 | BC4241 | -0.0007 | BH2821 | 0.0007 | YQGY | -0.0109 | OB1913 | -0.0133 |
| GK2439 | 5 | unknown conserved protein | -0.0017 | BC4258 | 0.0021 | BH2820 | -0.0143 | YQGX | -0.0081 | OB1916 | 0.0020 |
| GK2442 | 2.1.1 | glucokinase (EC 2.7.1.2) | 0.0393 | BC4260 | 0.0445 | BH1425 | 0.0220 | GLCK | 0.0243 | OB1919 | 0.0210 |
| GK2449 | 2.5 | 5-formyltetrahydrofolate cyclo-ligase | 0.0165 | BC4262 | 0.0427 | BH1417 | 0.0249 | YQGN | 0.0144 | OB1924 | -0.0189 |
| GK2454 | 1.2 | phosphate ABC transporter (ATP-binding protein) | 0.0252 | BC4266 | 0.0271 | BH2991 | 0.0194 | YQGK | -0.0203 | OB3133 | 0.0102 |
| GK2457 | 4.2 | manganese superoxide dismutase (EC 1.15.1.1) | -0.0024 | BC4272 | 0.0048 | BH1409 | -0.0100 | SODA | -0.0032 | OB1932 | 0.0023 |
| GK2465 | 5 | unknown conserved protein | -0.0021 | BC4275 | -0.0110 | BH1402 | 0.0181 | YQFZ | 0.0079 | OB1935 | -0.0469 |
| GK2468 | 5 | unknown conserved protein | 0.0304 | BC3386 | 0.0187 | BH1399 | 0.0101 | YQFW | -0.0341 | OB0422 | -0.0035 |
| GK2469 | 3.5.2 | transcriptional regulator (Fur family) | 0.0015 | BC4277 | 0.0263 | BH1396 | -0.0071 | YQFV | -0.0187 | OB2396 | 0.0111 |
| GK2471 | 1.2 | metal (zinc) ABC transporter (ATP-binding protein) | 0.0164 | BC4279 | 0.0329 | BH1394 | -0.0136 | YCDI | 0.0145 | OB2396 | -0.0187 |
| GK2473 | 5 | unknown conserved protein | -0.0064 | BC4281 | -0.0523 | BH1387 | -0.0801 | YQFT | -0.0503 | OB1937 | -0.0452 |
| GK2474 | 3.2 | endonuclease IV | 0.0175 | BC4282 | 0.0322 | BH1386 | 0.0288 | YQFS | 0.0226 | OB1938 | 0.0316 |
| GK2475 | 3.6 | ATP-dependent RNA helicase | 0.0195 | BC4283 | 0.0083 | BH1385 | 0.0175 | YQFR | 0.0216 | OB1939 | 0.0078 |
| GK2476 | 5 | unknown conserved protein | -0.0164 | BC4284 | -0.0323 | BH1384 | -0.0246 | YQFQ | -0.0361 | OB1735 | -0.0462 |
| GK2478 | 5 | unknown conserved protein | 0.0309 | BC4286 | 0.0319 | BH1380 | 0.0295 | YQFO | 0.0381 | OB1940 | 0.0057 |
| GK2479 | 5 | unknown conserved protein | 0.0400 | BC4287 | 0.0654 | BH1379 | 0.0231 | YQFN | 0.0184 | OB1941 | 0.0061 |
| GK2482 | 3.5.1 | RNA polymerase major sigma-43 factor (sigma-A) | 0.0501 | BC4289 | 0.0545 | BH1376 | 0.0517 | SIGA | 0.0492 | OB1944 | 0.0559 |
| GK2483 | 3.1 | DNA primase (EC 2.7.7.-) | 0.0255 | BC4290 | 0.0130 | BH1375 | 0.0215 | DNAG | -0.0002 | OB1945 | -0.0041 |
| GK2484 | 5 | unknown conserved protein | 0.0444 | BC4293 | 0.0396 | BH1373 | 0.0561 | YQFK | 0.0477 | OB1946 | 0.0313 |
| GK2485 | 5 | unknown conserved protein | 0.0316 | BC4294 | 0.0092 | BH1372 | 0.0129 | YQZB | 0.0168 | OB1947 | 0.0107 |
| GK2486 | 3.3 | DNA repair protein (recombination protein O) | 0.0067 | BC4295 | 0.0032 | BH1369 | 0.0003 | YQXN | 0.0061 | OB1950 | -0.0007 |
| GK2488 | 4.6 | GTP-binding protein | 0.0434 | BC4297 | 0.0360 | BH1367 | 0.0282 | BEX | 0.0202 | OB1951 | 0.0104 |
| GK2489 | 2.3 | cytidine deaminase (EC 3.5.4.5) | 0.0315 | BC4298 | 0.0215 | BH1366 | 0.0136 | CDD | 0.0062 | OB1751 | -0.0214 |
| GK2491 | 5 | unknown conserved protein | 0.0608 | BC4300 | 0.0826 | BH1363 | 0.0296 | YQFG | 0.0610 | OB1953 | 0.0390 |
| GK2493 | 2.6 | phosphate starvation-induced protein | 0.0223 | BC4302 | 0.0201 | BH1361 | 0.0244 | PHOH | 0.0194 | OB1955 | 0.0018 |
| GK2494 | 1.8 | stage IV sporulation protein | 0.0537 | BC4303 | 0.0513 | BH1360 | 0.0472 | YQFD | 0.0313 | OB1956 | 0.0444 |
| GK2495 | 5 | unknown conserved protein | 0.0343 | BC4304 | 0.0176 | BH1359 | -0.0352 | YQFC | 0.0336 | OB1957 | 0.0106 |
| GK2496 | 5 | unknown conserved protein | 0.0162 | BC4306 | 0.0180 | BH1355 | 0.0136 | YQEY | 0.0145 | OB1961 | 0.0146 |
| GK2497 | 3.7.1 | 30S ribosomal protein S21 | 0.0568 | BC4307 | 0.0544 | BH1354 | 0.0655 | RPSU | 0.0558 | OB1962 | 0.0482 |
| GK2499 | 2.3 | deoxyribose-phosphate aldolase (EC 4.1.2.4) | 0.0301 | BC1820 | 0.0471 | BH1352 | 0.0303 | DRA | 0.0427 | OB1963 | 0.0405 |
| GK2500 | 5 | unknown conserved protein | 0.0392 | BC4308 | 0.0469 | BH1351 | 0.0404 | YQEV | 0.0420 | OB1964 | 0.0357 |
| GK2501 | 5 | unknown conserved protein | 0.0345 | BC4309 | 0.0354 | BH1350 | 0.0329 | YQFU | 0.0160 | OB1965 | 0.0056 |
| GK2502 | 3.8 | ribosomal protein L11 methyltransferase (EC 2.1.1.-) | 0.0337 | BC4310 | 0.0367 | BH1349 | 0.0524 | YQET | 0.0355 | OB1966 | 0.0279 |
| GK2503 | 4.1 | chaperone protein (heat shock protein) | 0.0484 | BC4311 | 0.0337 | BH1348 | 0.0304 | DNAJ | 0.0313 | OB1967 | 0.0201 |
| GK2504 | 3.9 | chaperone protein (heat shock protein 70) (HSP70) | 0.0204 | BC4312 | 0.0257 | BH1346 | 0.0179 | DNAK | 0.0279 | OB1968 | 0.0121 |
| GK2505 | 4.1 | chaperone protein (heat shock protein) (HSP-70 cofactor) | 0.0639 | BC4313 | 0.0526 | BH1345 | 0.0814 | GRPE | 0.0253 | OB1969 | 0.0398 |
| GK2506 | 3.5.2 | transcription repressor of class I heat shock genes | 0.0042 | BC4314 | -0.0104 | BH1344 | 0.0088 | HRCA | -0.0175 | OB1970 | 0.0062 |
| GK2507 | 2.5 | coproporphyrinogen III oxidase (EC 1.3.3.3) | 0.0102 | BC4315 | 0.0194 | BH1343 | 0.0150 | HEMN | 0.0083 | OB1971 | 0.0012 |
| GK2508 | 3.7.4 | GTP-binding protein | 0.0364 | BC4317 | 0.0274 | BH1342 | 0.0318 | LEPA | 0.0355 | OB1972 | 0.0345 |
| GK2510 | 1.8 | stage II sporulation protein P (septal wall dissolution protein) | -0.0024 | BC2050 | -0.0179 | SPOIIP | 0.0224 | SPOIIP | -0.0101 | OB1974 | 0.0109 |
| GK2511 | 1.9 | spore protease (germination protease precursor) (EC 3.4.99.-) | 0.0112 | BC4319 | 0.0319 | BH1340 | 0.0408 | GPR | 0.0203 | OB1975 | 0.0417 |
| GK2512 | 3.7.1 | 30S ribosomal protein S20 | -0.0210 | BC4320 | -0.0294 | BH1332 | -0.0234 | RPST | -0.0095 | OB1976 | -0.0316 |
| GK2513 | 5 | unknown conserved protein | 0.0317 | BC4321 | 0.0228 | BH1337 | 0.0073 | YQEN | 0.0078 | OB1977 | -0.0082 |
| GK2516 | 1.10 | late competence protein (DNA binding and uptake) | -0.0040 | BC4323 | -0.0060 | BH1334 | 0.0204 | COMEB | 0.0073 | OB1980 | 0.0169 |
| GK2517 | 1.10 | late competence protein (DNA binding and uptake) | 0.0576 | BC4324 | 0.0423 | BH1333 | 0.0354 | COMEA | 0.0258 | OB1981 | -0.0070 |
| GK2519 | 5 | unknown conserved protein | 0.0276 | BC4326 | 0.0295 | BH1330 | 0.0169 | YQEM | -0.0020 | OB1982 | -0.0109 |
| GK2520 | 5 | unknown conserved protein | 0.0487 | BC4327 | 0.0268 | BH1328 | 0.0246 | YQEL | 0.0082 | OB1983 | 0.0371 |
| GK2521 | 5 | unknown conserved protein | 0.0219 | BC4328 | 0.0336 | BH1327 | -0.0125 | YQEK | 0.0135 | OB1984 | -0.0146 |
| GK2522 | 2.5 | nicotinate-nucleotide adenylyltransferase (EC 2.7.7.18) | 0.0387 | BC4329 | 0.0259 | BH1326 | 0.0314 | YQEJ | 0.0158 | OB1985 | 0.0021 |
| GK2523 | 5 | unknown conserved protein | 0.0211 | BC4330 | 0.0515 | BH1325 | 0.0418 | YQEI | 0.0062 | OB1986 | 0.0057 |
| GK2524 | 2.2 | shikimate 5-dehydrogenase (EC 1.1.1.25) | 0.0374 | BC4331 | 0.0136 | BH1324 | 0.0057 | AROD | 0.0175 | OB1987 | -0.0078 |
| GK2525 | 5 | unknown conserved protein | 0.0187 | BC4332 | 0.0083 | BH1323 | 0.0216 | YQEH | 0.0185 | OB1988 | -0.0123 |
| GK2526 | 5 | unknown conserved protein | 0.0149 | BC4333 | 0.0255 | BH1322 | 0.0221 | YQEG | 0.0392 | OB1989 | 0.0368 |

Fig. 10 K

| Gene | EC | Description | | | | | | | | |
|---|---|---|---|---|---|---|---|---|---|---|
| GK2542 | 2.3 | nucleoside phosphorylase (5'-methylthioadenosine nucleosidase (EC 3.2.2.16); S-adenosylhomocysteine nucleosidase (EC 3.2.2.9)) | 0.0335 | BC4368 | 0.0341 | BH1279 | 0.0111 | YRRU | 0.0334 | OB2000 | -0.0029 |
| GK2547 | 3.5.3 | transcription elongation factor | 0.0800 | BC4374 | 0.0527 | BH1276 | 0.0994 | GREA | 0.0727 | OB2002 | 0.0626 |
| GK2548 | 2.3 | uridine kinase (EC 2.7.1.48) | 0.0443 | BC4375 | 0.0142 | BH1275 | 0.0391 | UDK | 0.0174 | OB2003 | 0.0206 |
| GK2551 | 2.5 | caffeoyl-CoA O-methyltransferase | 0.0370 | BC4378 | 0.0471 | BH1272 | 0.0226 | YRRM | 0.0318 | OB2004 | 0.0143 |
| GK2552 | 5 | unknown conserved protein | 0.0050 | BC4379 | 0.0046 | BH1271 | 0.0366 | YRRL | -0.0100 | OB2005 | 0.0414 |
| GK2553 | 5 | unknown conserved protein | 0.1196 | BC4380 | 0.0975 | BH1270 | 0.1370 | YRZB | 0.0874 | OB2006 | 0.1168 |
| GK2554 | 5 | unknown conserved protein | 0.0315 | BC4381 | 0.0272 | BH1269 | 0.0195 | YRRK | 0.0159 | OB2007 | 0.0319 |
| GK2556 | 3.7.2 | alanyl-tRNA synthetase (EC 6.1.1.7) | 0.0412 | BC4383 | 0.0345 | BH1267 | 0.0391 | ALAS | 0.0403 | OB2009 | 0.0207 |
| GK2561 | 3.3 | ATP-dependent exonuclease V | 0.0175 | BC4389 | 0.0145 | BH1263 | 0.0317 | YRRG | 0.0097 | OB2012 | 0.0051 |
| GK2562 | 5 | unknown conserved protein | 0.0156 | BC4390 | 0.0129 | BH1262 | 0.0049 | YRRB | 0.0130 | OB2013 | -0.0149 |
| GK2564 | 2.5 | iron-sulfur cofactor synthesis | 0.0229 | BC4392 | 0.0164 | BH1260 | -0.0013 | YRVO | 0.0207 | OB2015 | -0.0054 |
| GK2565 | 5 | unknown conserved protein | 0.0535 | BC4393 | 0.0333 | BH1259 | 0.0465 | YRZC | -0.0046 | OB2016 | 0.0065 |
| GK2567 | 5 | unknown conserved protein | 0.0184 | BC4394 | -0.0189 | BH1257 | 0.0076 | YRVN | -0.0054 | OB2017 | -0.0100 |
| GK2572 | 3.7.2 | aspartyl-tRNA synthetase (EC 6.1.1.12) | 0.0361 | BC4397 | 0.0283 | BH1252 | 0.0184 | ASPS | 0.0251 | OB2019 | 0.0045 |
| GK2573 | 3.7.2 | histidyl-tRNA synthetase (EC 6.1.1.21) | 0.0283 | BC4398 | 0.0280 | BH1251 | 0.0162 | HISS | 0.0241 | OB2020 | 0.0150 |
| GK2577 | 3.7.2 | D-tyrosyl-tRNA(Tyr) deacylase | 0.0388 | BC4400 | 0.0339 | BH1243 | 0.0289 | YRVI | 0.0131 | OB2023 | 0.0126 |
| GK2578 | 2.3 | GTP pyrophosphokinase (pp(Gpp synthetase) (EC 2.7.6.5) | 0.0231 | BC4401 | 0.0373 | BH1242 | 0.0248 | RELA | 0.0318 | OB2024 | 0.0201 |
| GK2579 | 2.3 | adenine phosphoribosyltransferase (EC 2.4.2.7) | 0.0435 | BC4402 | 0.0712 | BH1241 | 0.0606 | APT | 0.0596 | OB2025 | 0.0770 |
| GK2580 | 3.3 | single-strand DNA-specific exonuclease | 0.0203 | BC4403 | 0.0167 | BH1240 | 0.0214 | YRVE | 0.0144 | OB2026 | 0.0000 |
| GK2583 | 5 | unknown conserved protein | 0.0152 | BC4406 | 0.0422 | BH1235 | 0.0256 | YRZD | 0.0402 | OB2028 | 0.0175 |
| GK2586 | 5 | unknown conserved protein | -0.0100 | BC4410 | 0.0025 | BH1229 | -0.0158 | YRBF | 0.0088 | OB2032 | -0.0074 |
| GK2587 | 3.6 | tRNA-guanine transglycosylase (EC 2.4.2.29) | 0.0207 | BC4411 | 0.0079 | BH1228 | 0.0021 | TGT | 0.0153 | OB2033 | -0.0037 |
| GK2588 | 3.6 | S-adenosylmethionine tRNA ribosyltransferase (EC 5.4.99.-) | 0.0391 | BC4412 | 0.0223 | BH1227 | 0.0154 | QUEA | 0.0250 | OB2034 | 0.0086 |
| GK2591 | 3.3 | holliday junction DNA helicase | 0.0380 | BC4414 | 0.0329 | BH1225 | 0.0365 | RUVB | 0.0278 | OB2036 | 0.0242 |
| GK2592 | 3.3 | Holliday junction DNA helicase | 0.0432 | BC4415 | 0.0421 | BH1224 | 0.0392 | RUVA | 0.0396 | OB2037 | -0.0063 |
| GK2596 | 2.5 | NH(3)-dependent NAD+ synthetase (EC 6.3.5.1) | 0.0382 | BC1994 | 0.0046 | BH2285 | 0.0049 | NADE | 0.0046 | OB0387 | 0.0046 |
| GK2598 | 6 | unknown | 0.0287 | BC4420 | -0.0168 | BH1221 | -0.0389 | YRBA | 0.0049 | OB2040 | -0.0311 |
| GK2604 | 2.2 | prephenate dehydratase (EC 4.2.1.51) | 0.0021 | BC4427 | 0.0132 | BH1215 | -0.0037 | PHEA | -0.0155 | OB2041 | -0.0093 |
| GK2606 | 1.8 | Spo0B-associated GTP-binding protein | 0.0535 | BC4434 | 0.0568 | BH1213 | 0.0449 | OBG | 0.0479 | OB2042 | 0.0381 |
| GK2607 | 1.8 | Stage 0 sporulation protein B (sporulation initiation phosphoprotein) | 0.0336 | BC4435 | -0.0167 | BH1212 | -0.0016 | SPO0B | -0.0207 | OB2043 | -0.0229 |
| GK2608 | 3.7.1 | 50S ribosomal protein L27 (BL30) | 0.0150 | BC4436 | 0.0167 | BH3009 | 0.0210 | RPMA | 0.0265 | OB2044 | 0.0242 |
| GK2609 | 5 | unknown conserved protein | 0.0477 | BC4437 | 0.0119 | BH3010 | 0.0255 | YSXB | 0.0269 | OB2045 | 0.0113 |
| GK2610 | 3.7.1 | 50S ribosomal protein L21 | 0.0646 | BC4438 | 0.0729 | BH3011 | 0.0944 | RPLU | 0.0685 | OB2046 | 0.0572 |
| GK2612 | 1.8 | inhibitor of SpoIVFB (stage IV sporulation protein FA) | 0.0427 | BC4441 | 0.0262 | BH3016 | 0.0303 | SPOIVFA | 0.0052 | OB2048 | -0.0175 |
| GK2613 | 1.7 | ATPase involved in chromosome partitioning | 0.0323 | BC4442 | 0.0265 | BH3027 | 0.0486 | MIND | 0.0246 | OB2049 | 0.0208 |
| GK2614 | 1.7 | septum formation inhibitor (cell-division inhibitor) | 0.0189 | BC4443 | 0.0333 | BH3028 | 0.0150 | MINC | -0.0083 | OB2050 | 0.0255 |
| GK2616 | 1.1 | cell-shape determining protein | 0.0349 | BC4445 | 0.0210 | BH3030 | 0.0409 | MREC | 0.0198 | OB2052 | 0.0396 |
| GK2617 | 1.1 | cell-shape determining protein | 0.0475 | BC4446 | 0.0347 | BH3031 | 0.0306 | MRED | 0.0415 | OB2053 | 0.0299 |
| GK2620 | 6 | unknown | 0.0144 | BC4463 | 0.0308 | BH3034 | -0.0044 | SPOIIB | 0.0199 | OB2057 | -0.0022 |
| GK2637 | 2.5 | folyl-polyglutamate synthetase (EC 6.3.2.17) | 0.0199 | BC4464 | 0.0325 | BH3037 | 0.0163 | FOLC | 0.0108 | OB2058 | -0.0115 |
| GK2640 | 5 | unknown conserved protein | 0.0327 | BC4466 | -0.0061 | BH3040 | -0.0003 | YSXE | 0.0194 | OB2063 | -0.0073 |
| GK2641 | 5 | unknown conserved protein | 0.0451 | BC4467 | 0.0814 | SPOVID | 0.0404 | SPOVID | 0.0510 | OB2064 | 0.0458 |
| GK2642 | 2.5 | glutamate-1-semialdehyde 2,1-aminotransferase (EC 5.4.3.8) | 0.0320 | BC4468 | 0.0301 | BH3043 | 0.0257 | HEML | 0.0238 | OB2065 | 0.0149 |
| GK2643 | 2.5 | delta-aminolevulinic acid dehydratase (porphobilinogen synthase) (EC 4.2.1.24) | 0.0286 | BC4469 | 0.0107 | BH3044 | 0.0131 | HEMB | 0.0243 | OB2066 | 0.0043 |
| GK2644 | 2.5 | uroporphyrinogen III cosynthase (EC 4.2.1.75) | 0.0158 | BC4470 | 0.0259 | BH3045 | 0.0327 | HEMD | 0.0091 | OB2067 | 0.0081 |
| GK2645 | 2.5 | porphobilinogen deaminase (hydroxymethylbilane synthase) (EC 4.3.1.8) | 0.0375 | BC4471 | 0.0175 | BH3046 | 0.0277 | HEMC | 0.0401 | OB2068 | 0.0528 |
| GK2647 | 2.5 | glutamyl-tRNA reductase (EC 1.2.1.-) | 0.0120 | BC4473 | 0.0259 | BH3048 | 0.0119 | HEMA | 0.0202 | OB2070 | 0.0110 |
| GK2649 | 4.6 | GTP-binding protein | 0.0086 | BC4476 | 0.0209 | BH3049 | 0.0070 | YSXC | 0.0299 | OB2075 | 0.0124 |
| GK2650 | 4.1 | ATP-dependent Lon protease (EC 3.4.21.53) | 0.0395 | BC4477 | 0.0367 | BH3050 | 0.0353 | LONA | 0.0345 | OB2076 | 0.0258 |
| GK2652 | 4.1 | ATP-dependent Clp protease ATP-binding subunit (class III heat-shock protein) | 0.0401 | BC4479 | 0.0381 | BH3052 | 0.0420 | CLPX | 0.0366 | OB2077 | 0.0451 |
| GK2653 | 3.9 | trigger factor (prolyl isomerase) | 0.0766 | BC4480 | 0.0783 | BH3053 | 0.0645 | TIG | 0.0823 | OB2078 | 0.0815 |
| GK2654 | 5 | unknown conserved protein | 0.0065 | BC4481 | 0.0375 | BH3054 | 0.0125 | YSOA | 0.0370 | OB2079 | -0.0207 |
| GK2655 | 2.2 | 3-isopropylmalate dehydratase small subunit (EC 4.2.1.33) | 0.0107 | BG1403 | 0.0086 | BH3055 | 0.0119 | LEUD | -0.0230 | OB2617 | -0.0190 |
| GK2656 | 2.2 | 3-isopropylmalate dehydratase large subunit (EC 4.2.1.33) | 0.0236 | BC1402 | 0.0167 | BH3056 | 0.0162 | LEUC | 0.0343 | OB2618 | 0.0156 |
| GK2657 | 2.2 | 3-isopropylmalate dehydrogenase (EC 1.1.1.85) | 0.0254 | BC1401 | 0.0346 | BH3057 | 0.0315 | LEUB | 0.0236 | OB2619 | 0.0135 |
| GK2658 | 2.2 | 2-isopropylmalate synthase (EC 4.1.3.12) | 0.0210 | BC1400 | 0.0095 | BH3058 | 0.0051 | LEUA | 0.0095 | OB2620 | 0.0122 |
| GK2659 | 2.2 | ketol-acid reductoisomerase (EC 1.1.1.86) | 0.0329 | BG1399 | 0.0453 | BH3059 | 0.0249 | ILVC | 0.0374 | OB2621 | 0.0256 |
| GK2660 | 2.2 | acetolactate synthase (acetohydroxy-acid synthase) small subunit (EC 4.1.3.18) | 0.0225 | BG1398 | 0.0181 | BH3060 | 0.0169 | ILVN | 0.0212 | OB2622 | -0.0038 |
| GK2661 | 2.2 | acetolactate synthase large subunit (EC 4.1.3.18) | 0.0075 | BC1777 | 0.0249 | BH3061 | -0.0002 | ILVB | 0.0188 | OB2623 | -0.0031 |
| GK2664 | 5 | unknown conserved protein | 0.0230 | BC4492 | 0.0240 | BH3066 | 0.0126 | YSNB | 0.0194 | OB2104 | 0.0228 |
| GK2665 | 5 | unknown conserved protein | 0.0527 | BC4493 | 0.0564 | BH3067 | 0.0296 | YSNA | 0.0694 | OB2105 | 0.0076 |
| GK2666 | 3.6 | ribonuclease PH (EC 2.7.7.56) | 0.0547 | BC4494 | 0.0464 | BH3068 | 0.0158 | RPH | 0.0202 | OB2106 | 0.0098 |
| GK2667 | 1.9 | germination (cortex hydrolysis) and sporulation (stage II, multiple polar septa) | 0.0168 | BC4495 | 0.0058 | BH3070 | 0.0408 | GERM | 0.0031 | OB2107 | 0.0285 |
| GK2670 | 3.5.2 | transcriptional regulator | 0.0262 | BC4501 | 0.0421 | BH3075 | 0.0450 | GERE | 0.0413 | OB2110 | 0.0280 |
| GK2671 | 2.1.3 | succinate dehydrogenase (iron-sulfur protein) (EC 1.3.99.1) | 0.0056 | BC4516 | -0.0278 | BH3091 | -0.0105 | SDHB | -0.0096 | OB2112 | -0.0183 |

Fig. 10 L

| Gene | EC | Description | | | | | | | |
|---|---|---|---|---|---|---|---|---|---|
| GK2672 | 2.1.3 | succinate dehydrogenase (flavoprotein subunit) (EC 1.3.99.1) | 0.0269 | BC4517 | 0.0199 | BH3092 | 0.0229 | SDHA | 0.0108 | OB2113 | 0.0201 |
| GK2674 | 5 | unknown conserved protein | -0.0067 | BC4519 | 0.0129 | BH3095 | -0.0006 | YSIB | 0.0244 | OB2115 | 0.0203 |
| GK2675 | 3.2 | excinuclease ABC (subunit C) (EC 4.1.99.3) | 0.0403 | BC4520 | 0.0366 | BH3097 | 0.0242 | UVRC | 0.0176 | OB2116 | 0.0160 |
| GK2685 | 1.4 | thioredoxin (TRX) | 0.0313 | BC4521 | 0.0512 | BH3098 | 0.0072 | TRXA | 0.0450 | OB2117 | 0.0386 |
| GK2687 | 1.4 | electron transfer flavoprotein beta subunit | 0.0654 | BC4523 | 0.0569 | BH3100 | 0.0522 | ETFB | 0.0443 | OB2119 | 0.0647 |
| GK2688 | 2.4 | enoyl-CoA hydratase (EC 4.2.1.17) | 0.0471 | BC4524 | 0.0145 | BH3101 | 0.0047 | YSIB | 0.0138 | OB2120 | 0.0087 |
| GK2689 | 3.5.2 | transcriptional regulator (TetR/AcrR family) | 0.0242 | BC4525 | -0.0072 | BH3102 | 0.0035 | YSIA | 0.0041 | OB2121 | 0.0080 |
| GK2694 | 3.2 | DNA-dependent DNA polymerase beta chain | 0.0236 | BC4553 | 0.0327 | BH3107 | 0.0309 | YSHC | 0.0225 | OB2125 | 0.0236 |
| GK2696 | 5 | unknown conserved protein | 0.0428 | BC4555 | 0.0316 | BH3109 | 0.0356 | YSHA | 0.0518 | OB2127 | 0.0118 |
| GK2706 | 3.7.2 | phenylalanyl-tRNA synthetase beta subunit (EC 6.1.1.20) | 0.0473 | BC4560 | 0.0443 | BH3110 | 0.0390 | PHET | 0.0286 | OB2130 | 0.0202 |
| GK2707 | 3.7.2 | phenylalanyl-tRNA synthetase alpha subunit (EC 6.1.1.20) | 0.0402 | BC4561 | 0.0444 | BH3111 | 0.0336 | PHES | 0.0440 | OB2131 | 0.0309 |
| GK2709 | 3.6 | rRNA methylase (EC 2.1.1.-) | 0.0171 | BC4562 | 0.0330 | BH3112 | 0.0200 | YSGA | 0.0129 | OB2132 | 0.0035 |
| GK2712 | 5 | unknown conserved protein | -0.0079 | BC4563 | 0.0093 | BH3113 | -0.0330 | YSFA | 0.0205 | OB2133 | -0.0131 |
| GK2713 | 5 | unknown conserved protein | 0.0391 | BC4571 | 0.0328 | BH3132 | 0.0408 | YSDC | 0.0256 | OB2143 | 0.0197 |
| GK2715 | 5 | unknown conserved protein | 0.0031 | BC4560 | 0.0037 | BH3136 | 0.0008 | YSDA | -0.0095 | OB2149 | 0.0103 |
| GK2716 | 3.7.1 | 50S ribosomal protein L20 | -0.0192 | BC4573 | -0.0078 | BH3138 | -0.0250 | RPLT | -0.0270 | OB2150 | -0.0150 |
| GK2717 | 3.7.1 | 50S ribosomal protein L35 | -0.0335 | BC4554 | -0.0261 | BH3139 | -0.0205 | RPMI | -0.0374 | OB2151 | -0.0205 |
| GK2718 | 3.7.3 | translation initiation factor IF-3 | 0.0235 | BC4575 | 0.0185 | BH3140 | 0.0259 | INFC | 0.0219 | OB2152 | 0.0545 |
| GK2719 | 3.7.2 | threonyl-tRNA synthetase (EC 6.1.1.3) | 0.0531 | BC4576 | 0.0509 | BH3141 | 0.0431 | THRS | 0.0443 | OB2154 | 0.0361 |
| GK2720 | 5 | unknown conserved protein | -0.0002 | BC4577 | 0.0045 | BH3142 | 0.0326 | YTXC | 0.0154 | OB2155 | 0.0289 |
| GK2721 | 3.1 | primosome component (helicase loader) | 0.0055 | BC4579 | 0.0203 | BH3144 | 0.0084 | DNAI | 0.0018 | OB2156 | -0.0071 |
| GK2722 | 3.1 | chromosome replication initiation/membrane attachment protein | 0.0258 | BC4580 | 0.0272 | BH3145 | 0.0144 | DNAB | 0.0044 | OB2157 | -0.0261 |
| GK2723 | 5 | unknown conserved protein | 0.0892 | BC4581 | 0.0776 | BH3146 | 0.0704 | YTCG | 0.0746 | OB2158 | 0.0625 |
| GK2725 | 2.2 | S-adenosylmethionine decarboxylase (EC 4.1.1.50) | 0.0257 | BC4582 | 0.0302 | BH3148 | 0.0348 | YTCF | 0.0196 | OB0938 | 0.0389 |
| GK2726 | 2.1.2 | glyceraldehyde-3-phosphate dehydrogenase (EC 1.2.1.12) | 0.0118 | BC4583 | 0.0239 | BH3149 | 0.0274 | GAPB | 0.0223 | OB2160 | 0.0171 |
| GK2727 | 5 | unknown conserved protein | 0.0313 | BC4584 | 0.0413 | BH3150 | 0.0148 | YTAG | 0.0229 | OB2161 | 0.0088 |
| GK2728 | 3.2 | formamidopyrimidine-DNA glycosidase (EC 3.2.2.23) | 0.0435 | BC4586 | 0.0459 | BH3152 | 0.0138 | MUTM | 0.0251 | OB2162 | 0.0149 |
| GK2730 | 3.1 | DNA-directed DNA polymerase I (POL I) (EC 2.7.7.7) | 0.0258 | BC4587 | 0.0261 | BH3153 | 0.0244 | POLA | 0.0244 | OB2163 | 0.0128 |
| GK2731 | 1.3 | two-component sensor histidine kinase (phosphate regulation) | 0.0247 | BC4588 | 0.0346 | BH3156 | 0.0168 | PHOR | 0.0136 | OB2164 | 0.0176 |
| GK2732 | 3.5.2 | two-component response regulator (phosphate regulation) | 0.0458 | BC4589 | 0.0285 | BH3157 | 0.0048 | PHOP | 0.0380 | OB2165 | 0.0295 |
| GK2734 | 1.2 | malate dehydrogenase (EC 1.1.1.37) | 0.0395 | BC4592 | 0.0332 | BH3158 | 0.0456 | CITH | 0.0391 | OB2166 | 0.0256 |
| GK2735 | 2.1.3 | isocitrate dehydrogenase (EC 1.1.1.42) | 0.0410 | BC4593 | 0.0418 | BH3159 | 0.0368 | CITC | 0.0359 | OB2167 | 0.0426 |
| GK2736 | 2.1.3 | citrate synthase II (EC 4.1.3.7) | 0.0266 | BC4594 | 0.0210 | BH3160 | 0.0199 | CITZ | 0.0228 | OB2168 | 0.0065 |
| GK2739 | 2.1.2 | pyruvate kinase (EC 2.7.1.40) | 0.0293 | BC4599 | 0.0382 | BH3163 | 0.0349 | PYKA | 0.0222 | OB2171 | 0.0201 |
| GK2740 | 2.1.2 | 6-phosphofructokinase (Phosphofructokinase) (Phosphohexokinase) (EC 2.7.1.11) | 0.0433 | BC4600 | 0.0416 | BH3164 | 0.0343 | PFK | 0.0547 | OB2172 | 0.0354 |
| GK2741 | 2.4 | acetyl CoA carboxylase alpha subunit (EC 6.4.1.2) | 0.0340 | BC4601 | 0.0412 | BH3165 | 0.0349 | ACCA | 0.0238 | OB2173 | 0.0331 |
| GK2742 | 2.4 | acetyl-CoA carboxylase beta subunit (EC 6.4.1.2) | 0.0222 | BC4602 | 0.0330 | BH3166 | 0.0146 | YTTI | 0.0067 | OB2174 | 0.0067 |
| GK2744 | 3.1 | DNA-directed DNA polymerase III alpha subunit | 0.0133 | BC4605 | 0.0147 | BH3169 | 0.0342 | DNAE | 0.0016 | OB2177 | 0.0036 |
| GK2747 | 5 | unknown conserved protein | 0.0343 | BC4608 | 0.0301 | BH3173 | 0.0340 | YTQI | 0.0105 | OB2181 | 0.0259 |
| GK2748 | 5 | unknown conserved protein | -0.0108 | BC4609 | 0.0022 | BH3174 | -0.0093 | YTPI | -0.0020 | OB2182 | -0.0129 |
| GK2749 | 5 | unknown conserved protein | 0.0268 | BC4611 | 0.0245 | BH3175 | 0.0263 | YTOI | 0.0274 | OB2183 | 0.0090 |
| GK2750 | 5 | unknown conserved protein | 0.0098 | BC4613 | 0.0136 | BH3178 | 0.0096 | YTKL | -0.0030 | OB2186 | -0.0044 |
| GK2751 | 3.8 | Xaa-Pro dipeptidase | 0.0195 | BC4614 | 0.0418 | BH3179 | 0.0156 | YKVY | 0.0262 | OB2187 | 0.0014 |
| GK2756 | 2.2 | argininosuccinate lyase (arginosuccinase) (EC 4.3.2.1) | 0.0128 | BC4629 | 0.0008 | BH3186 | 0.0051 | ARGH | 0.0074 | OB3128 | 0.0068 |
| GK2757 | 2.2 | argininosuccinate synthase (citrulline--aspartate ligase) (EC 6.3.4.5) | 0.0320 | BC4630 | 0.0243 | BH3187 | 0.0420 | ARGG | 0.0288 | OB3129 | 0.0243 |
| GK2785 | 2.1.1 | acetate kinase (acetokinase) (EC 2.7.2.1) | 0.0295 | BC4637 | 0.0366 | BH3192 | 0.0244 | ACKA | 0.0328 | OB2191 | 0.0199 |
| GK2786 | 5 | unknown conserved protein | -0.0175 | BC4638 | 0.0022 | BH3193 | -0.0166 | YTXK | -0.0218 | OB2192 | -0.0274 |
| GK2787 | 4.2 | thiol peroxidase (EC 1.1.1.1.-) (superoxide-inducible protein 8) | 0.0179 | BC4639 | 0.0096 | BH3194 | 0.0135 | YTGI | 0.0340 | OB2193 | 0.0064 |
| GK2788 | 5 | unknown conserved protein | -0.0194 | BC2095 | -0.0024 | BH3195 | -0.0094 | YTBJ | -0.0085 | OB2194 | 0.0426 |
| GK2789 | 5 | unknown conserved protein | 0.0287 | BC4641 | 0.0182 | BH3196 | 0.0081 | YTH | -0.0059 | OB2195 | -0.0208 |
| GK2792 | 5 | unknown conserved protein | 0.0161 | BC4642 | -0.0013 | BH3199 | -0.0069 | YTDI | -0.0090 | OB2196 | 0.0022 |
| GK2793 | 2.1.1 | acetate-CoA ligase (EC 6.2.1.1) | 0.0423 | BC4645 | 0.0381 | BH3201 | 0.0263 | YTCI | 0.0337 | OB2643 | 0.0240 |
| GK2795 | 2.5 | protein involved in thiamine biosynthesis | 0.0201 | BC4647 | 0.0415 | BH3203 | 0.0092 | YTBJ | -0.0044 | OB2198 | 0.0120 |
| GK2796 | 4.6 | cysteine desulfurase (EC 4.4.1.-) | 0.0214 | BC4648 | 0.0189 | BH3204 | 0.0049 | NIFZ | -0.0022 | OB2199 | 0.0061 |
| GK2798 | 1.7 | septation ring formation regulator | 0.0359 | BC4649 | 0.0214 | BH3205 | 0.0381 | YTWP | 0.0382 | OB2200 | 0.0247 |
| GK2800 | 5 | unknown conserved protein | 0.0031 | BC4653 | 0.0075 | BH3208 | 0.0120 | YTSP | 0.0298 | OB2202 | -0.0118 |
| GK2802 | 3.7.1 | 30S ribosomal protein S4 | 0.0165 | BC4655 | 0.0215 | BH3209 | 0.0133 | RPSD | 0.0199 | OB2205 | 0.0162 |
| GK2806 | 2.1.1 | acetyl-CoA synthetase (EC 6.2.1.1) | 0.0397 | BC4659 | 0.0326 | BH3234 | 0.0279 | ACSA | 0.0402 | OB0022 | 0.0325 |
| GK2807 | 2.1.1 | acetoin utilization protein | 0.0442 | BC4660 | 0.0151 | BH3235 | 0.0274 | ACUA | 0.0384 | OB2221 | 0.0284 |
| GK2808 | 2.1.1 | acetoin utilization protein | -0.0014 | BC4661 | 0.0079 | BH3236 | 0.0006 | ACUB | 0.0070 | OB2222 | 0.0091 |
| GK2809 | 2.1.1 | acetoin utilization protein | 0.0050 | BC4662 | 0.0044 | BH3237 | -0.0014 | ACUC | -0.0062 | OB2223 | -0.0067 |
| GK2810 | 3.5.2 | transcriptional regulator involved in carbon catabolite control | 0.0345 | BC4672 | 0.0148 | BH3241 | 0.0366 | CCPA | 0.0123 | OB2226 | 0.0037 |
| GK2814 | 5 | unknown conserved protein | -0.0032 | BC4677 | 0.0130 | BH3245 | -0.0230 | YTXG | -0.0269 | OB2230 | -0.0497 |
| GK2815 | 1.1 | UDP-N-acetyl muramate-alanine ligase (EC 6.3.2.8) | -0.0081 | BC4684 | 0.0105 | BH3248 | -0.0073 | MURC | 0.0017 | OB2231 | -0.0041 |
| GK2817 | 5 | unknown conserved protein | 0.0522 | BC4689 | 0.0458 | BH3251 | 0.0216 | YTPR | 0.0382 | OB2233 | 0.0237 |
| GK2818 | 5 | unknown conserved protein | 0.0406 | BC4690 | 0.0270 | BH3252 | 0.0152 | YTTQ | 0.0148 | OB2234 | 0.0174 |
| GK2820 | 5 | unknown conserved protein | 0.0152 | BC4693 | -0.0057 | BH3257 | 0.0104 | YTOP | -0.0051 | OB2238 | 0.0041 |

Fig. 10 M

| Gene | EC | Description | | | | | | | | | |
|---|---|---|---|---|---|---|---|---|---|---|---|
| GK2821 | 5 | unknown conserved protein | 0.0049 | BC4694 | 0.0345 | BH3258 | -0.0059 | YTZB | 0.0319 | OB2239 | 0.0494 |
| GK2822 | 5 | unknown conserved protein | 0.0189 | BC4695 | 0.0161 | BH3260 | 0.0121 | YTNP | 0.0088 | OB2240 | 0.0131 |
| GK2823 | 5 | unknown conserved protein | 0.0029 | BC4696 | 0.0427 | BH3261 | 0.0106 | YTMQ | 0.0156 | OB2294 | 0.0038 |
| GK2825 | 5 | unknown conserved protein | -0.0102 | BC4698 | -0.0285 | BH3263 | -0.0158 | YTMP | -0.0065 | OB2296 | -0.0256 |
| GK2827 | 2.1.1 | pullulanase (EC 3.2.1.68) | 0.0219 | BC2734 | 0.0118 | BH3264 | 0.0180 | AMYX | 0.0056 | OB0405 | -0.0252 |
| GK2829 | 5 | unknown conserved protein | 0.0089 | BC4701 | 0.0112 | BH3270 | -0.0151 | YTPP | 0.0076 | OB2298 | -0.0573 |
| GK2833 | 3.6 | 16S pseudouridylate synthase (EC 4.2.1.70) | 0.0612 | BC4704 | 0.0749 | BH3273 | 0.0604 | YTZF | 0.0296 | OB2299 | 0.0152 |
| GK2836 | 5 | unknown conserved protein | 0.0285 | BC4706 | 0.0148 | BH3279 | 0.0152 | YTFP | 0.0051 | OB2301 | 0.0050 |
| GK2846 | 5 | unknown conserved protein | 0.0014 | BC4747 | 0.0225 | BH3285 | 0.0008 | YTOB | 0.0039 | OB2308 | -0.0084 |
| GK2848 | 5 | unknown conserved protein | 0.0254 | BC4754 | 0.0175 | BH3289 | 0.0299 | YTOA | 0.0091 | OB2312 | 0.0250 |
| GK2849 | 2.2 | S-adenosylmethionine synthetase (EC 2.5.1.6) | 0.0266 | BC4761 | 0.0235 | BH3300 | 0.0229 | METK | 0.0291 | OB2314 | 0.0301 |
| GK2850 | 2.1.2 | phosphoenolpyruvate carboxykinase (EC 4.1.1.49) | 0.0065 | BC4762 | 0.0062 | BH3302 | 0.0039 | PCKA | 0.0172 | OB2315 | -0.0067 |
| GK2858 | 5 | unknown conserved protein | 0.0526 | BC4785 | 0.0499 | BH3308 | 0.0231 | YTKD | 0.0520 | OB2319 | 0.0434 |
| GK2863 | 1.3 | autoinducer-2 production protein (EC 3.13.1.-) (AI-2 synthesis protein) | 0.0137 | BC4789 | -0.0008 | BH3353 | 0.0120 | YTJB | 0.0214 | OB1107 | 0.0063 |
| GK2864 | 5 | unknown conserved protein | -0.0062 | BC4790 | -0.0167 | BH2828 | 0.0141 | YTJA | -0.0053 | OB1687 | 0.0336 |
| GK2878 | 5 | unknown conserved protein | 0.0346 | BC4858 | 0.0231 | BH2544 | 0.0398 | YTEA | 0.0103 | OB0582 | 0.0300 |
| GK2923 | 5 | unknown conserved protein | 0.0033 | BC4897 | 0.0323 | BH3341 | 0.0119 | YUCN | 0.0114 | OB0399 | -0.0089 |
| GK2924 | 2.1.2 | glucose-6-phosphate isomerase A (phosphoglucose isomerase A) (EC 5.3.1.9) | 0.0249 | BC4898 | 0.0213 | BH3343 | 0.0182 | PGI | 0.0198 | OB2336 | 0.0021 |
| GK2926 | 5 | unknown conserved protein | -0.0219 | BC4899 | -0.0202 | BH3345 | -0.0169 | YUZA | -0.0018 | OB2283 | 0.0344 |
| GK2927 | 3.6 | polyribonucleotide nucleotidyltransferase | 0.0567 | BC4900 | 0.0401 | BH3347 | 0.0267 | YUGI | 0.0428 | OB2335 | 0.0281 |
| GK2931 | 2.2 | aminotransferase | 0.0150 | BC4906 | -0.0197 | BH3313 | 0.0193 | PATB | -0.0040 | OB2338 | 0.0005 |
| GK2949 | 5 | unknown conserved protein | 0.0235 | BC4922 | 0.0355 | BH3404 | 0.0434 | YUIC | 0.0068 | OB2348 | 0.0204 |
| GK2950 | 5 | unknown conserved protein | -0.0289 | BC4923 | -0.0191 | BH3405 | -0.0443 | YUIB | -0.0139 | OB2349 | -0.0174 |
| GK2953 | 1.4 | NADH dehydrogenase (EC 1.6.99.3) | 0.0517 | BC4925 | 0.0475 | BH3407 | 0.0432 | YUMB | 0.0414 | OB1365 | 0.0237 |
| GK2954 | 1.4 | thioredoxin reductase | 0.0129 | BC4926 | 0.0236 | BH3408 | 0.0145 | YUMC | 0.0244 | OB2351 | 0.0266 |
| GK2956 | 5 | unknown conserved protein | 0.0207 | BC4935 | 0.0520 | BH3410 | 0.0331 | YUTM | 0.0220 | OB2353 | 0.0128 |
| GK2957 | 2.2 | diaminopimelate epimerase | 0.0643 | BC4936 | 0.0539 | BH3412 | 0.0420 | YUTL | 0.0356 | OB2354 | 0.0336 |
| GK2960 | 5 | unknown conserved protein | 0.0732 | BC4951 | 0.0783 | BH3416 | 0.0693 | YUZD | 0.0643 | OB2355 | 0.0306 |
| GK2961 | 4.6 | nitrogen fixation protein (NifU protein) | 0.0766 | BC4952 | 0.0728 | BH3419 | 0.0833 | YUTI | 0.0492 | OB2356 | 0.0575 |
| GK2962 | 2.2 | homoserine kinase (EC 2.7.1.39) | 0.0276 | BC1966 | 0.0198 | BH3420 | 0.0015 | THRB | 0.0295 | OB0464 | -0.0029 |
| GK2963 | 2.2 | threonine synthase (EC 4.2.3.1) | 0.0260 | BC1965 | 0.0206 | BH3421 | 0.0270 | THRC | 0.0299 | OB0465 | 0.0101 |
| GK2964 | 2.2 | homoserine dehydrogenase (EC 1.1.1.3) | 0.0269 | BC5404 | 0.0332 | BH3422 | 0.0358 | HOM | 0.0336 | OB0466 | 0.0126 |
| GK2966 | 5 | unknown conserved protein | 0.0342 | BC4954 | 0.0099 | BH3423 | 0.0051 | YUTH | -0.0148 | OB2358 | -0.0135 |
| GK2967 | 5 | unknown conserved protein | 0.0120 | BC4955 | 0.0201 | BH3424 | 0.0146 | YUTG | 0.0176 | OB2359 | 0.0068 |
| GK2968 | 5 | unknown conserved protein | 0.0252 | BC4959 | 0.0397 | BH3428 | 0.0193 | YUTF | 0.0208 | OB2360 | 0.0050 |
| GK2969 | 5 | unknown conserved protein | 0.0300 | BC4961 | 0.0487 | BH3430 | 0.0342 | YUTE | 0.0056 | OB2362 | 0.0097 |
| GK2972 | 5 | unknown conserved protein | 0.0112 | BC4966 | 0.0222 | BH3433 | 0.0270 | YUTD | 0.0228 | OB2365 | 0.0386 |
| GK2973 | 5 | unknown conserved protein | -0.0104 | BC4967 | -0.0283 | BH3434 | -0.0075 | YUTC | -0.0283 | OB2366 | -0.0173 |
| GK2974 | 2.5 | lipoic acid synthetase (lipoate synthase) | 0.0273 | BC4973 | 0.0240 | BH3435 | 0.0295 | YUTB | 0.0115 | OB1284 | 0.0137 |
| GK2975 | 5 | unknown conserved protein | 0.0147 | BC4974 | 0.0009 | BH3436 | 0.0239 | YUNA | 0.0181 | OB2367 | 0.0163 |
| GK2981 | 5 | unknown conserved protein | 0.0190 | BC4975 | 0.0000 | BH1036 | -0.0007 | YUNB | -0.0012 | OB2370 | 0.0251 |
| GK2982 | 5 | unknown conserved protein | 0.0596 | BC4976 | 0.0375 | BH3452 | 0.0324 | YUNC | 0.0252 | OB2372 | 0.0319 |
| GK2983 | 5 | unknown conserved protein | 0.0247 | BC4977 | 0.0332 | BH3453 | 0.0191 | YUND | 0.0291 | OB2373 | -0.0100 |
| GK2985 | 5 | unknown conserved protein | 0.0141 | BC1459 | 0.0098 | BH3455 | 0.0183 | YUNF | -0.0143 | OB0397 | -0.0167 |
| GK2991 | 5 | unknown conserved protein | 0.0274 | BC4979 | 0.0286 | BH3467 | 0.0281 | YUBU | 0.0338 | OB2376 | 0.0280 |
| GK2992 | 4.6 | nitrogen fixation protein NifU | 0.0118 | BC4980 | 0.0035 | BH3468 | -0.0181 | YURV | 0.0021 | OB2377 | -0.0049 |
| GK2993 | 2.2 | cysteine desulfurase (EC 4.4.1.-) | 0.0136 | BC4981 | 0.0188 | BH3469 | 0.0118 | YURW | 0.0144 | OB2378 | 0.0001 |
| GK2994 | 5 | unknown conserved protein | 0.0257 | BC4982 | 0.0187 | BH3470 | 0.0275 | YURX | 0.0135 | OB2379 | -0.0068 |
| GK2995 | 1.2 | ABC transporter (ATP-binding protein) | 0.0430 | BC4983 | 0.0479 | BH3471 | 0.0338 | YURY | 0.0419 | OB2380 | 0.0405 |
| GK2996 | 5 | unknown conserved protein | -0.0045 | BC2830 | -0.0295 | BH3473 | -0.0525 | YURZ | -0.0163 | OB2779 | 0.0138 |
| GK2999 | 1.2 | ABC transporter (ATP-binding protein) | 0.0196 | BC4987 | 0.0100 | BH3481 | 0.0382 | YUSC | 0.0155 | OB2384 | 0.0041 |
| GK3001 | 1.4 | thioredoxin | 0.0122 | BC4989 | 0.0386 | BH1715 | 0.0281 | YUSE | -0.0126 | OB2385 | 0.0167 |
| GK3004 | 2.2 | protein H involved in glycine cleavage system | 0.0762 | BC4991 | 0.0692 | BH3484 | 0.1111 | YUSH | 0.0917 | OB2388 | 0.0774 |
| GK3005 | 4.2 | arsenate reductase | 0.0267 | BC4992 | 0.0255 | BH3485 | 0.0371 | YUSI | 0.0382 | OB2189 | -0.0011 |
| GK3006 | 2.4 | acetyl-CoA dehydrogenase | 0.0288 | BC5002 | 0.0336 | BH3486 | 0.0323 | YUSJ | 0.0283 | OB2393 | 0.0365 |
| GK3007 | 2.4 | acetyl-CoA acyltransferase | 0.0380 | BC5003 | 0.0197 | BH3487 | 0.0330 | YUSK | 0.0206 | OB2394 | 0.0188 |
| GK3008 | 2.4 | 3-hydroxyacyl-CoA dehydrogenase | 0.0290 | BC5004 | 0.0241 | BH3488 | 0.0182 | YUSL | 0.0195 | OB2395 | 0.0201 |
| GK3012 | 5 | unknown conserved protein | -0.0923 | BC4997 | -0.0807 | BH3490 | -0.0947 | YUSN | -0.0993 | OB0829 | -0.0673 |
| GK3043 | 3.8 | ssrA RNA (tmRNA)-binding protein | 0.0470 | BC5128 | 0.0226 | BH3552 | 0.0275 | YVAI | 0.0196 | OB2426 | 0.0132 |
| GK3044 | 2.3 | ribonuclease R | 0.0613 | BC5129 | 0.0540 | BH3553 | 0.0563 | YVAJ | 0.0402 | OB2428 | 0.0425 |
| GK3045 | 4.2 | carboxylesterase (EC 3.1.1.1) | 0.0311 | BC5130 | 0.0159 | BH3554 | 0.0524 | YVAK | 0.0406 | OB2429 | 0.0180 |
| GK3046 | 1.6 | protein translocation subunit | -0.0281 | BC5131 | -0.0263 | BH3555 | -0.0190 | YVAL | -0.0298 | OB2430 | -0.0151 |
| GK3054 | 2.1.2 | enolase (2-phosphoglycerate dehydratase) (EC 4.2.1.11) | 0.0410 | BC5135 | 0.0343 | BH3556 | 0.0258 | ENO | 0.0231 | OB2434 | 0.0293 |
| GK3055 | 2.1.2 | 2,3-bisphosphoglycerate-independent phosphoglycerate mutase (Phosphoglyceromutase) (EC 5.4.2.1) | 0.0239 | BC5136 | 0.0375 | BH3557 | 0.0264 | PGM | 0.0197 | OB2435 | 0.0156 |
| GK3058 | 2.1.2 | glyceraldehyde-3-phosphate dehydrogenase (phosphorylating) (EC 1.2.1.12) | 0.0287 | BC5140 | 0.0188 | BH3560 | 0.0193 | GAP | 0.0170 | OB2438 | 0.0107 |
| GK3059 | 3.5.2 | transcriptional regulator (central glycolytic gene regulator) | 0.0307 | BC5141 | 0.0059 | BH3561 | 0.0224 | YVBQ | 0.0151 | OB2439 | 0.0269 |
| GK3061 | 3.5.1 | RNA polymerase sigma-54 factor (sigma-L) | 0.0122 | BC5143 | -0.0060 | BH3563 | -0.0137 | SIGL | -0.0366 | OB2441 | -0.0116 |
| GK3062 | 4.1 | ATP-dependent Clp protease proteolytic subunit (class III heat-shock protein) | -0.0096 | BC5152 | -0.0168 | BH3564 | -0.0065 | CLPP | 0.0052 | OB2456 | 0.0070 |
| GK3063 | 2.1.1 | phosphotransferase system phosphocarrier protein HPr | 0.0282 | BC5153 | -0.0074 | BH3566 | 0.0319 | CRH | 0.0230 | OB2465 | 0.0312 |
| GK3064 | 5 | unknown conserved protein | 0.0142 | BC5154 | 0.0171 | BH3567 | 0.0086 | YVCL | 0.0125 | OB2466 | 0.0144 |
| GK3065 | 5 | unknown conserved protein | 0.0183 | BC5155 | 0.0271 | BH3568 | 0.0236 | YVCK | 0.0255 | OB2467 | 0.0035 |
| GK3066 | 5 | unknown conserved protein | -0.0020 | BC5156 | 0.0153 | BH3569 | 0.0086 | YVCJ | 0.0144 | OB2468 | -0.0022 |
| GK3068 | 1.4 | thioredoxin reductase (EC 1.8.1.9) | 0.0553 | BC5159 | 0.0595 | BH3571 | 0.0442 | TRXB | 0.0646 | OB2469 | 0.0331 |
| GK3069 | 5 | unknown conserved protein | 0.0091 | BC5160 | -0.0004 | BH3572 | -0.0018 | YVCD | 0.0019 | OB2470 | 0.0033 |
| GK3071 | 2.2 | imidazoleglycerol-phosphate synthase (EC 4.1.3.-) | 0.0374 | BC1410 | 0.0472 | BH3578 | 0.0463 | HISF | 0.0477 | OB0547 | 0.0257 |

Fig. 10 N

| | | | | | | | | | | |
|---|---|---|---|---|---|---|---|---|---|---|
| GK3072 | 2.2 | phosphoribosylformimino-5-aminoimidazole carboxamide ribotide isomerase (EC 5.3.1.16) | 0.0321 | BC1409 | 0.0361 | BH3579 | 0.0212 | HISA | 0.0410 | OB0548 -0.0015 |
| GK3073 | 2.2 | imidazole glycerol phosphate synthase subunit (EC 2.4.2.-) | 0.0450 | BC1408 | 0.0430 | BH3580 | 0.0199 | HISH | 0.0257 | OB0549 -0.0065 |
| GK3074 | 2.2 | imidazoleglycerol-phosphate dehydratase (EC 4.2.1.19) | 0.0186 | BC1407 | 0.0037 | BH3581 | 0.0145 | HISB | 0.0120 | OB0550 -0.0059 |
| GK3075 | 2.2 | histidinol dehydrogenase (EC 1.1.1.23) | 0.0395 | BC1406 | 0.0424 | BH3582 | 0.0108 | HISD | 0.0231 | OB0551 -0.0137 |
| GK3076 | 2.2 | ATP phosphoribosyltransferase (EC 2.4.2.17) | 0.0555 | BC1405 | 0.0403 | BH3583 | 0.0653 | HISG | 0.0489 | OB0552 0.0157 |
| GK3077 | 3.7.2 | histidyl-tRNA synthetase (EC 6.1.1.21) | 0.0315 | BC1404 | 0.0413 | BH3584 | 0.0176 | HISZ | 0.0323 | OB0553 -0.0410 |
| GK3078 | 2.1.1 | acetyltransferase | 0.0213 | BC5161 | 0.0291 | BH3586 | 0.0297 | YVOF | 0.0285 | OB2478 0.0377 |
| GK3079 | 2.1.1 | phosphoglycolate phosphatase | 0.0269 | BC5162 | 0.0169 | BH3587 | 0.0476 | YVOE | 0.0100 | OB2479 -0.0131 |
| GK3082 | 3.8 | HPr(Ser/Thr) kinase/phosphatase (EC 2.7.1.-) | 0.0466 | BC5164 | 0.0156 | BH3590 | 0.0194 | YVOB | 0.0335 | OB2482 0.0382 |
| GK3085 | 3.2 | excinuclease ABC subunit A | 0.0323 | BC5167 | 0.0309 | BH3594 | 0.0240 | UVRA | 0.0244 | OB2487 0.0173 |
| GK3086 | 3.2 | excinuclease ABC subunit B | 0.0405 | BC5168 | 0.0436 | BH3595 | 0.0357 | UVRB | 0.0436 | OB2488 0.0372 |
| GK3092 | 2.2 | carboxy-terminal processing protease | 0.0164 | BC5184 | 0.0211 | BH3599 | 0.0315 | YWJB | 0.0067 | OB2490 0.0325 |
| GK3101 | 1.7 | cell-division ATP-binding protein | 0.0535 | BC5186 | 0.0590 | BH3602 | 0.0442 | FTSE | 0.0497 | OB2493 0.0582 |
| GK3106 | 3.7.5 | peptide chain release factor 2 in translation | 0.0254 | BC5188 | 0.0284 | BH3605 | 0.0157 | PRFB | 0.0162 | OB2495 0.0026 |
| GK3107 | 1.6 | preprotein translocase subunit (ATPase, RNA helicase) | 0.0410 | BC5189 | 0.0364 | BH3606 | 0.0314 | SECA | 0.0297 | OB2496 0.0201 |
| GK3109 | 3.7.1 | ribosomal protein S30EA | 0.0499 | BC5190 | 0.0594 | BH3608 | 0.0508 | YVYD | 0.0249 | OB2498 0.0479 |
| GK3114 | 1.5 | flagellar hook-associated protein 2 (filament cap protein) | -0.0375 | BC1638 | -0.0128 | BH3614 | -0.0361 | FLID | -0.0311 | OB2501 -0.0069 |
| GK3128 | 1.8 | dTDP-glucose 4,6-dehydratase (EC 4.2.1.46) | 0.0211 | BC1214 | 0.0170 | BH3364 | -0.0082 | SPSJ | 0.0103 | OB2420 0.0064 |
| GK3131 | 1.5 | flagellin protein | -0.0513 | BC1658 | -0.0622 | BH3616 | -0.0567 | HAG | -0.0578 | OB2727 -0.0528 |
| GK3136 | 1.5 | flagellar hook-associated protein 3 | -0.0266 | BC1637 | -0.0437 | BH3620 | -0.0045 | H.GL | -0.0340 | OB2506 -0.0219 |
| GK3137 | 1.5 | flagellar hook-associated protein 1 (HAP1) | -0.0208 | BC1636 | -0.0254 | BH3621 | -0.0223 | FLGK | -0.0298 | OB2507 -0.0215 |
| GK3141 | 5 | unknown conserved protein | 0.0462 | BC1634 | -0.0003 | BH1478 | 0.0537 | YAAR | -0.0060 | OB0038 -0.0302 |
| GK3146 | 1.10 | late competence protein | 0.0067 | BC5192 | 0.0267 | BH3625 | 0.0116 | COMFC | -0.0184 | OB2516 -0.0177 |
| GK3147 | 1.10 | late competence protein | 0.0157 | BC5193 | 0.0236 | BH3626 | -0.0100 | COMFA | 0.0012 | OB2517 -0.0163 |
| GK3149 | 5 | unknown conserved protein | 0.0231 | BC5198 | 0.0400 | BH3627 | 0.0345 | YWIA | 0.0265 | OB2518 0.0149 |
| GK3152 | 5 | unknown conserved protein | 0.0384 | BC5199 | 0.0278 | BH3630 | 0.0246 | YWYE | 0.0456 | OB2521 0.0198 |
| GK3212 | 2.1.1 | 6-phospho-beta-glucosidase (EC 3.2.1.86) | 0.0350 | BC5209 | 0.0362 | BH0183 | 0.0394 | LICH | 0.0297 | OB0811 0.0342 |
| GK3228 | 1.2 | ribose ABC transporter (ATP-binding protein) | 0.0405 | BC0662 | 0.0249 | BH3730 | 0.0382 | RBSA | 0.0301 | OB2574 0.0329 |
| GK3229 | 1.2 | ribose ABC transporter (permease) | 0.0079 | BC0661 | 0.0568 | BH3729 | 0.0362 | RBSD | 0.0058 | OB2575 0.0108 |
| GK3230 | 2.1.1 | ribokinase (EC 2.7.1.15) | 0.0052 | BC0660 | 0.0356 | BH3728 | 0.0054 | RBSK | 0.0120 | OB2576 0.0328 |
| GK3231 | 3.5.2 | transcriptional repressor of the ribose operon | 0.0323 | BC0659 | 0.0197 | BH3727 | 0.0256 | RBSR | -0.0030 | OB2577 0.0057 |
| GK3323 | 4.1 | involved in capsular polysaccharide biosynthesis | 0.0071 | BC5276 | 0.0054 | BH3667 | 0.0061 | YWQE | -0.0049 | OB2899 -0.0284 |
| GK3324 | 3.5.2 | attenuator role for lytABC and lytR expression | 0.0197 | BC5265 | 0.0076 | BH3670 | 0.0036 | LYTR | 0.0124 | OB2530 -0.0113 |
| GK3329 | 2.4 | hydroxymyristoyl-[acyl carrier protein] dehydratase (EC 4.2.1.-) | 0.0394 | BC5280 | 0.0691 | BH3735 | 0.0592 | YWPB | 0.0431 | OB2946 0.0605 |
| GK3332 | 1.5 | flagellar basal-body rod protein | -0.0069 | BC1671 | -0.0263 | BH3738 | -0.0083 | FLHO | -0.0369 | OB2957 -0.0364 |
| GK3333 | 1.1 | cell shape determining protein (MreB-like protein) | 0.0491 | BC5281 | 0.0545 | BH3739 | 0.0413 | MBL | 0.0501 | OB2958 0.0504 |
| GK3334 | 3.5.2 | transcriptional regulator of sigma-E/sigma-K-dependent gene (stage III sporulation protein D) | 0.0537 | BC5282 | 0.0842 | BH3740 | 0.0832 | SPOIIID | 0.0699 | OB2959 0.0742 |
| GK3339 | 1.8 | stage II sporulation protein | 0.0049 | BC5283 | 0.0102 | BH3748 | 0.0395 | SPOIIQ | 0.0276 | OB2961 0.0419 |
| GK3340 | 1.8 | stage II sporulation protein D | 0.0104 | BC5287 | 0.0218 | SPOIID | 0.0257 | SPOIID | -0.0065 | OB2962 0.0162 |
| GK3341 | 1.1 | UDP-N-acetylglucosamine 1-carboxyvinyltransferase (EC 2.5.1.7) | 0.0387 | BC5288 | 0.0387 | BH3749 | 0.0451 | MURA | 0.0400 | OB2972 0.0408 |
| GK3342 | 5 | unknown conserved protein | -0.0310 | BC5289 | 0.0175 | BH3750 | -0.0280 | YWMB | -0.0120 | OB2973 0.0013 |
| GK3357 | 1.4 | F0F1-type ATP synthase epsilon chain (EC 3.6.3.14) | 0.0389 | BC5305 | 0.0389 | BH3753 | 0.0519 | ATPC | 0.0332 | OB2974 0.0358 |
| GK3358 | 1.4 | F0F1-type ATP synthase beta chain (EC 3.6.3.14) | 0.0333 | BC5306 | 0.0184 | BH3754 | 0.0233 | ATPD | 0.0281 | OB2975 0.0349 |
| GK3359 | 1.4 | F0F1-type ATP synthase gamma chain (EC 3.6.3.14) | -0.0116 | BC5307 | -0.0010 | BH3755 | -0.0100 | ATPG | -0.0004 | OB2976 -0.0136 |
| GK3360 | 1.4 | F0F1-type ATP synthase alpha chain (EC 3.6.3.14) | 0.0131 | BC5308 | 0.0159 | BH3756 | 0.0148 | ATPA | 0.0087 | OB2977 0.0142 |
| GK3361 | 1.4 | F0F1-type ATP synthase delta chain (EC 3.6.3.14) | 0.0026 | BC5309 | 0.0323 | BH3757 | 0.0141 | ATPH | -0.0065 | OB2978 -0.0147 |
| GK3362 | 1.4 | F0F1-type ATP synthase B chain (EC 3.6.3.14) | 0.0327 | BC5310 | 0.0425 | BH3758 | 0.0373 | ATPF | 0.0173 | OB2979 0.0113 |
| GK3363 | 1.4 | F0F1-type ATP synthase C chain (EC 3.6.3.14) | 0.0242 | BC5311 | 0.0241 | BH3759 | 0.0056 | ATPE | 0.0231 | OB2980 0.0192 |
| GK3368 | 2.3 | uracil phosphoribosyltransferase (EC 2.4.2.9) | 0.0522 | BC5313 | 0.0437 | BH3764 | 0.0541 | UPP | 0.0549 | OB2984 0.0540 |
| GK3369 | 2.2 | serine hydroxymethyltransferase (EC 2.1.2.1) | 0.0160 | BC5316 | 0.0238 | BH3765 | 0.0230 | GLYA | 0.0250 | OB2985 0.0162 |
| GK3370 | 5 | unknown conserved protein | 0.0289 | BC5317 | 0.0361 | BH3766 | 0.0092 | YWLG | 0.0026 | OB2986 0.0100 |
| GK3373 | 3.8 | protein-tyrosine-phosphatase (EC 3.1.3.48) | 0.0251 | BC5319 | 0.0104 | BH3769 | 0.0335 | YWLE | 0.0020 | OB2988 -0.0342 |
| GK3375 | 5 | unknown conserved protein | 0.0295 | BC5325 | 0.0361 | BH3771 | 0.0112 | YWLC | 0.0143 | OB2994 -0.0062 |
| GK3376 | 1.8 | stage II sporulation protein R (pro-sigma-E processing factor) | 0.0320 | BC5327 | 0.0847 | SPOIIR | 0.0236 | SPOIIR | 0.0323 | OB2996 0.0588 |
| GK3377 | 2.5 | protoporphyrinogen oxidase | 0.0357 | BC5328 | 0.0624 | BH3774 | 0.0300 | YWKE | 0.0497 | OB2997 0.0005 |
| GK3378 | 3.7.5 | peptide chain release factor 1 (RF-1) in translation | 0.0456 | BC5329 | 0.0337 | BH3775 | 0.0317 | PRFA | 0.0349 | OB2998 0.0379 |
| GK3380 | 2.3 | thymidine kinase (EC 2.7.1.21) | 0.0178 | BC5330 | 0.0233 | BH3779 | 0.0330 | TDK | 0.0252 | OB2999 0.0370 |
| GK3382 | 3.5.4 | transcriptional terminator | 0.0310 | BC5332 | 0.0327 | BH3781 | 0.0439 | RHO | 0.0246 | OB3001 0.0219 |
| GK3383 | 5 | unknown conserved protein | 0.0479 | BC5333 | 0.0404 | BH3783 | 0.0427 | YWJI | 0.0454 | OB3002 0.0271 |
| GK3384 | 1.1 | UDP-N-acetylglucosamine 1-carboxyvinyltransferase (EC 2.5.1.7) | 0.0358 | BC5334 | 0.0307 | BH3784 | 0.0217 | MURZ | 0.0270 | OB3003 0.0179 |
| GK3385 | 2.1.2 | transaldolase (EC 2.2.1.2) | 0.0031 | BC0665 | 0.0300 | BH3785 | 0.0005 | YWJH | 0.0024 | OB3004 -0.0040 |
| GK3386 | 2.1.2 | fructose-bisphosphate aldolase (EC 4.1.2.13) | 0.0437 | BC5335 | 0.0451 | BH3786 | 0.0405 | FBAA | 0.0388 | OB3005 0.0417 |
| GK3389 | 2.3 | CTP synthetase (UTP--ammonia ligase) (EC 6.3.4.2) | 0.0319 | BC5338 | 0.0234 | BH3792 | 0.0231 | CTRA | 0.0304 | OB3007 0.0286 |
| GK3390 | 3.5.3 | DNA-directed RNA polymerase (EC 2.7.7.6) delta subunit | 0.0707 | BC5339 | 0.0800 | BH3793 | 0.0960 | RPOE | 0.0826 | OB3008 0.0541 |
| GK3393 | 2.4 | acyl-CoA dehydrogenase (EC 1.3.99.3) | 0.0307 | BC5341 | 0.0316 | BH3798 | 0.0331 | ACDA | 0.0257 | OB3010 0.0198 |
| GK3394 | 2.4 | acyl-CoA dehydrogenase (EC 1.3.99.-) | 0.0329 | BC5342 | 0.0235 | BH3799 | 0.0187 | MMGC | 0.0054 | OB3011 0.0193 |

Fig. 10 O

| Gene | EC | Description | Val1 | Ortholog | Val2 | Ortholog | Val3 | Ortholog | Val4 | Ortholog | Val5 |
|---|---|---|---|---|---|---|---|---|---|---|---|
| GK3395 | 2.4 | 3-hydroxybutyryl-CoA dehydrogenase (EC 1.1.1.157) | 0.0354 | BC5343 | 0.0398 | BH3800 | 0.0257 | MMGB | 0.0345 | OB3012 | 0.0192 |
| GK3397 | 2.4 | acetyl-CoA acetyltransferase (EC 2.3.1.9) | 0.0298 | BC5344 | 0.0275 | BH3801 | 0.0163 | MMGA | 0.0195 | OB3013 | 0.0289 |
| GK3401 | 3.7.2 | arginyl-tRNA synthetase (EC 6.1.1.19) | 0.0253 | BC5364 | 0.0228 | BH3808 | 0.0203 | ARGS | 0.0289 | OB3015 | 0.0104 |
| GK3402 | 5 | unknown conserved protein | 0.0363 | BC5365 | 0.0148 | BH3809 | 0.0061 | YWIB | 0.0411 | OB3016 | 0.0038 |
| GK3406 | 1.1 | penicillin-binding protein | 0.0057 | BC5375 | -0.0058 | BH3812 | 0.0013 | YWHE | -0.0089 | OB3017 | -0.0023 |
| GK3407 | 5 | unknown conserved protein | 0.0500 | BC5376 | 0.0468 | BH3813 | 0.0662 | YWHD | 0.0495 | OB3018 | 0.0259 |
| GK3411 | 5 | unknown conserved protein | 0.0192 | BC5379 | 0.0280 | BH3818 | 0.0171 | YWTO | 0.0187 | OB3020 | 0.0096 |
| GK3414 | 5 | unknown conserved protein | 0.0179 | BC5386 | -0.0199 | BH3822 | -0.0258 | YWFL | 0.0057 | OB3021 | 0.0134 |
| GK3415 | 2.1.1 | phosphotransacetylase (EC 2.3.1.8) | 0.0226 | BC5387 | 0.0338 | BH3823 | 0.0146 | PTA | 0.0232 | OB3022 | 0.0286 |
| GK3416 | 5 | unknown conserved protein | 0.0105 | BC5388 | 0.0218 | BH3825 | 0.0146 | YWHI | 0.0048 | OB3023 | 0.0476 |
| GK3418 | 5 | unknown conserved protein | -0.0123 | BC5391 | -0.0755 | BH3827 | -0.0720 | YWDL | -0.0528 | OB3025 | -0.0668 |
| GK3421 | 3.2 | uracil-DNA glycosylase (EC 3.2.2.-) | 0.0128 | BC5398 | 0.0129 | BH3850 | -0.0253 | UNG | -0.0109 | OB2129 | -0.0163 |
| GK3422 | 4.1 | stage II sporulation protein AA (anti-anti-sigma factor, antagonist of SpoIIAB) | 0.0009 | BC1002 | 0.0087 | BH0527 | 0.0340 | RSBV | 0.0183 | OB0628 | 0.0206 |
| GK3423 | 4.1 | anti-sigma B factor (Ser/Thr protein kinase) | 0.0184 | BC1003 | 0.0417 | BH0528 | 0.0333 | RSBW | 0.0289 | OB0629 | 0.0551 |
| GK3424 | 3.5.1 | DNA-directed RNA polymerase sigma-37 factor (sigma-B) | -0.0001 | BC1004 | 0.0220 | BH0529 | 0.0301 | SIGB | 0.0146 | OB0630 | 0.0248 |
| GK3446 | 1.2 | PTS system, glucose-specific enzyme II, A component | 0.0440 | BC5320 | 0.0627 | BH1515 | 0.0455 | YPQE | 0.0614 | OB2758 | 0.0648 |
| GK3453 | 1.2 | amino acid ABC transporter (substrate-binding protein) | 0.0145 | BC4150 | 0.0478 | BH1461 | 0.0533 | YQIX | 0.0226 | OB1004 | 0.0300 |
| GK3456 | 1.4 | cytochrome aa3 quinol oxidase subunit IV | -0.0320 | BC0695 | -0.0649 | BH2067 | -0.0107 | QOXD | -0.0308 | OB2256 | -0.0186 |
| GK3459 | 1.4 | cytochrome aa3 quinol oxidase subunit II | 0.0164 | BC0698 | 0.0198 | BH2064 | 0.0172 | QOXA | 0.0097 | OB2253 | 0.0198 |
| GK3463 | 1.4 | Rieske [2Fe-2S] iron-sulfur protein | -0.0007 | BC0399 | -0.0048 | BH3871 | -0.0002 | YHFW | 0.0086 | OB1729 | -0.0032 |
| GK3467 | 5 | unknown conserved protein | 0.0314 | BC5456 | 0.0301 | BH4007 | 0.0342 | YYDA | 0.0252 | OB3379 | 0.0391 |
| GK3469 | 4.1 | serine protease Do | 0.0174 | BC5458 | 0.0228 | BH4022 | 0.0261 | YYXA | 0.0228 | OB3447 | 0.0307 |
| GK3471 | 5 | unknown conserved protein | 0.0167 | BC5460 | -0.0036 | BH4024 | -0.0262 | YYCI | 0.0014 | OB3449 | -0.0064 |
| GK3472 | 5 | unknown conserved protein | 0.0220 | BC5461 | 0.0063 | BH4025 | 0.0054 | YYCH | -0.0321 | OB3450 | 0.0096 |
| GK3473 | 1.3 | two-component sensor histidine kinase | 0.0180 | BC5462 | 0.0017 | BH4026 | 0.0023 | YYCG | 0.0162 | OB3451 | 0.0073 |
| GK3474 | 3.5.2 | two-component response regulator | 0.0545 | BC5463 | 0.0583 | BH4027 | 0.0438 | YYCF | 0.0545 | OB3452 | 0.0542 |
| GK3475 | 2.3 | adenylosuccinate synthase (EC 6.3.4.4) | 0.0506 | BC5465 | 0.0493 | BH4028 | 0.0522 | PURA | 0.0450 | OB3453 | 0.0392 |
| GK3476 | 3.1 | replicative DNA helicase | 0.0037 | BC5466 | 0.0295 | BH4029 | 0.0103 | DNAC | 0.0030 | OB3460 | -0.0030 |
| GK3477 | 3.7.1 | 50S ribosomal protein L9 (BL17) | 0.0236 | BC5471 | 0.0285 | BH4030 | 0.0519 | RPLI | 0.0313 | OB3461 | 0.0310 |
| GK3478 | 5 | unknown conserved protein | 0.0153 | BC5472 | 0.0085 | BH4031 | 0.0194 | YYBT | 0.0125 | OB3462 | 0.0150 |
| GK3480 | 3.7.1 | 30S ribosomal protein S18 (BS21) | 0.0230 | BC5474 | 0.0347 | BH4048 | 0.0150 | RPSR | 0.0211 | OB3477 | 0.0152 |
| GK3481 | 3.1 | single-strand DNA-binding protein | 0.0036 | BC5475 | -0.0251 | BH4049 | -0.0060 | SSB | -0.0248 | OB3478 | -0.0402 |
| GK3482 | 3.7.1 | 30S ribosomal protein S6 (BS9) | 0.0771 | BC5476 | 0.0841 | BH4050 | 0.0768 | RPSF | 0.0533 | OB3479 | 0.0615 |
| GK3483 | 5 | unknown conserved protein | 0.0462 | BC5477 | 0.0531 | BH4051 | 0.0363 | YYAE | 0.0420 | OB3480 | 0.0449 |
| GK3487 | 5 | unknown conserved protein | 0.0162 | BC5480 | -0.0255 | BH4054 | -0.0239 | YYAC | -0.0160 | OB3484 | -0.0089 |
| GK3489 | 1.8 | stage 0 sporulation protein J (antagonist of Soj) | 0.0247 | BC5481 | 0.0278 | SPO0J | 0.0294 | SPO0J | 0.0019 | OB3486 | 0.0271 |
| GK3490 | 1.8 | sporulation initiation inhibitor protein | 0.0149 | BC5482 | 0.0051 | BH4058 | 0.0104 | SOJ | 0.0157 | OB3487 | 0.0006 |
| GK3491 | 5 | unknown conserved protein | 0.0278 | BC5483 | 0.0272 | BH4059 | 0.0209 | YYAA | 0.0271 | OB3488 | 0.0177 |
| GK3492 | 1.7 | glucose-inhibited division protein | 0.0107 | BC5484 | 0.0243 | BH4060 | 0.0203 | GIDB | 0.0147 | OB3489 | 0.0227 |
| GK3493 | 1.7 | glucose-inhibited division protein | 0.0266 | BC5485 | 0.0242 | BH4061 | 0.0280 | GIDA | 0.0205 | OB3490 | 0.0229 |
| GK3494 | 4.2 | thiophen/furan oxidation protein | 0.0370 | BC5486 | 0.0374 | BH4062 | 0.0399 | THDF | 0.0416 | OB3491 | 0.0346 |
| GK3495 | 1.8 | SpoIIIJ-associated protein | 0.0454 | BC5487 | 0.0238 | BH4063 | 0.0597 | JAG | 0.0028 | OB3493 | 0.0121 |
| GK3497 | 3.6 | ribonuclease P (protein component) | 0.0314 | BC5489 | 0.0313 | BH4065 | 0.0324 | RNPA | 0.0015 | OB3495 | -0.0018 |
| GK3498 | 3.7.1 | 50S ribosomal protein L34 | 0.0198 | BC5490 | 0.0042 | BH4066 | 0.0158 | RPMH | -0.0077 | OB3496 | 0.0056 |

>0.015 : to be judged to have thermostability  BC:*Bacillus cereus*
>0.010 : to be judged to have thermostability  BS:*Bacillus subtilis*
>0.005 : to be judged to have thermostability  BH:*Bacillus halodurans*

OB:*Oceanobacillus iheyensis*

GK:*Geobacillus kaustophilus*

Essential genes of B. Subtilis are shown in red.

METHOD AND COMPUTER PROGRAM PRODUCT FOR DETERMINING WHETHER OR NOT A TEST PROTEIN HAS THERMOSTABILITY

The patent or application file contains at least one drawing executed in color. Copies of this patent or patent application publication with color drawing(s) will be provided by the Office upon request and payment of the necessary fee.

BACKGROUND OF THE INVENTION

1. Field of the Invention

The present invention relates to a method of judging whether or not a protein has thermostability by focusing on a protein produced by an organism, and calculating a characteristic value related to thermostability from the data of the amino acid sequence or the nucleotide sequence of the protein. More particularly, the invention relates to a method of judging the thermostability of a protein, which judges whether or not a test protein has thermostability, comprising the steps of calculating an analytical value specific to the test protein by a principal component analysis based on the amino acid composition of the protein, and comparing the analytical value with an analytical value of a protein which is retained by a thermostable organism and corresponds to the test protein.

In addition, the invention relates to a program for judging whether or not the protein has thermostability by focusing on a protein produced by an organism, and calculating a characteristic value related to thermostability from the data of the amino acid sequence or the nucleotide sequence of the protein, and a recording medium having recorded the program thereon. More particularly, the invention relates to a program for allowing a computer to execute processing for judging the thermostability of a protein, which judges whether or not a test protein has thermostability by calculating an analytical value specific to the test protein by a principal component analysis based on the amino acid composition of the protein, and comparing the analytical value with an analytical value of a protein which is retained by a thermostable organism and corresponds to the test protein, and a computer readable recording medium having recorded the program thereon.

2. Background Art

Thermostable enzymes are widely used in the industrial world, research and development fields and the like as an enzyme that does not lose the enzymatic activity at a high temperature. Examples of the thermostable enzyme include, an enzyme used in an enzymatic reaction process for hydrolysis of a saccharide such as starch (see JP-T-10-506524 (the term "JP-T" as used herein means a published Japanese translation of a PCT patent application), and JP-A-2000-50870), an enzyme used in an enzymatic reaction in the disposal of food waste or in the production of a fertilizer from the food waste (see JP-A-2001-61474 and JP-A-2003-219864), an enzyme used in an enzymatic reaction in the production of a useful substance such as trehalose (see JP-A-08-336388 and JP-A-08-149980) and the like.

As described above, thermostable enzymes are very important in the industry. Recently, it has become important to develop a thermostable DNA polymerase to be used in the PCR method (see JP-B-04-67957), or in a replicative RNA-based amplification system (see JP-A-02-5864 and JP-A-02-500565), and a large number of thermostable DNA polymerases have been isolated mainly from thermophilic microorganisms. A DNA polymerase has become one of the important tools in genetic engineering techniques, and has become important as a tool not only for gene cloning or sequence determination, but also for detection or identification of a small amount of gene, namely, as an enzyme for gene amplification.

At present, thermostable DNA polymerases to be used mainly for these purposes are derived from the genus *Thermus* as Taq polymerase which is derived from *T. aquaticus*. The interest on the discovery of a novel polymerase with a more appropriate property and activity is growing, and as a DNA polymerase from other than the genus *Thermus*, for example, a method using a DNA polymerase from *Anaerocellum thermophilum* (see JP-T-2001-502169), a method using a DNA polymerase from a sulfur metabolism thermophilic archaebacterium *Pyrococcus horikoshii* (see JP-A-2000-41668) and the like have been reported.

In this way, the importance of thermostable enzymes is growing more and more, however, a search of such a thermostable enzyme often requires the steps of screening a bacterium producing a target enzyme from the natural world using thermophilic bacteria or thermostable bacteria as a target for screening, and confirming the thermostability of an enzyme produced by studying the culture conditions by performing a heat treatment one by one. Therefore, not only it required enormous time and effort, but also it depended on a coincidence in many cases. In addition, the subject of screening was limited to thermophilic bacteria, thermostable bacteria or mesophilic bacteria, and the thermophilic bacteria or thermostable bacteria was only limited species in light of numerous species of microorganisms, therefore the diversity of thermostable enzymes was limited.

Not only an accidental discovery is expected, but also the establishment of a systematic and saving method for searching a useful thermostable enzyme in industry was needed. Further, the development of a computer processable program, which is for conveniently executing the method was needed.

SUMMARY OF THE INVENTION

An object of the invention is to improve the conventional methods by which a thermostable enzyme search was performed through a trial and error process, and the invention provides a novel method which is a convenient method based on data such as the amino acid sequence or the nucleotide sequence of a protein and is capable of judging whether or not the protein has thermostability.

In addition, the invention provides a method capable of conveniently judging a wider variety of thermostable enzymes than ever by using resources of thermostable proteins such as useful enzymes as microorganisms for industry and thermostable enzymes to be used widely.

Further, an object of the invention is to improve the conventional methods by which a thermostable enzyme search was performed through a trial and error process, and the invention provides a computer program for judging whether or not a protein has thermostability by a convenient method based on data such as the amino acid sequence or the nucleotide sequence of the protein, data for the program and a recording medium of the program.

The present inventors carried out a principal component analysis by using the amino acid composition of a protein predicted in the genomes of 120 species of microorganisms whose complete genome sequences had been known until then, and calculated the principal component score of each protein based on the eigenvector of the second principal component (weighting factor of amino acid), and examined the correlation between the calculated value and the thermostability of the protein. As a result, they found out that there is an extremely strong correlation between the calculated value and the value of a protein which corresponds to the protein and is produced by a thermophilic bacterium. By utilizing this correlation, the inventors established a method capable of judging the thermostability of a protein, thus achieved the invention.

In addition, this method requires a large amount of data processing such as a search of a protein showing an orthologous relationship, calculation of a specific analytical value (vector value) by a principal component analysis of a test protein, and comparison with a known protein. Therefore, computerization of data processing such as calculation and search described above was needed. The inventors developed a program therefor and could complete the program.

In other words, the invention relates to a method of judging the thermostability of a protein, which judges whether or not a test protein has thermostability, comprising the steps of calculating an analytical value specific to the test protein by a principal component analysis based on the amino acid composition of the protein, and comparing the analytical value with an analytical value of a protein which is retained by a thermostable organism and corresponds to the test protein.

The invention provides a method of judging whether or not a protein has thermostability by using a specific analytical value obtained by a principal component analysis based on the amino acid composition of the protein, which is predicted from the data of the amino acid sequence or the nucleotide sequence of the protein, without performing a thermostability test of the protein.

The method of the invention can be programmed so as to be processed in a computer, and the invention provides a method capable of judging whether or not a protein has thermostability by inputting the data of the amino acid sequence or the nucleotide sequence of the protein into the program and allowing the computer to execute processing.

In addition, the invention relates to a program for allowing a computer to execute processing for judging the thermostability of a protein, which allows a computer to judge whether or not a test protein has thermostability, by calculating an analytical value specific to the test protein by a principal component analysis based on the amino acid composition of the protein, and comparing the analytical value with an analytical value of a protein which is retained by a thermostable organism and corresponds to the test protein.

Further, the invention relates to a program, which allows a computer to judge whether or not a test protein has thermostability by executing the steps of:

(1) inputting the amino acid sequence of the test protein, (2) searching a known protein related to a protein corresponding to the test protein and produced by another species different from the one producing the test protein (hereinafter referred to as corresponding protein), (3) calculating a specific analytical value by a principal component analysis based on the amino acid composition of the test protein, (4) calculating the specific analytical value of the corresponding protein searched in the step (2) and the specific analytical value of the test protein calculated in the step (3), and calculating the difference between both values, (5) judging whether or not the test protein is similar to the corresponding protein searched in the step (2) based on the difference calculated in the step (4), and (6) displaying the corresponding protein searched in the step (2) and the result of judgment in the step (5), whereby the specific analytical value based on the amino acid composition of the test protein and the specific analytical value of the known corresponding protein are compared to judge whether or not the test protein has thermostability.

In addition, the invention relates to a computer readable recording medium having recorded thereon a program for allowing a computer to execute the program of the invention.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

In FIG. 3, the horizontal axis represents the values of the "principal component score" of GK, and the vertical axis represents the values of the "principal component score" of GS.

In FIG. 5, the horizontal axis represents the temperature and the vertical axis represents the ratio (%). On the horizontal axis, the upper limit temperatures for growth of the respective microorganisms are plotted. On the vertical axis, with regard to the upper line (indicated in green in the original figure), the ratios (%), relative to all the 965 proteins, of the number of proteins in the case where the difference in the values of the "principal component scores" between GK and each of the other microorganisms is greater than −0.015 are plotted for each of the microorganisms, with regard to the line in the middle (indicated in blue in the original figure), the ratios (%) of the number of proteins in the case where the difference is greater than −0.010 are plotted for each of the microorganisms, and with regard to the lower line (indicated in red in the original figure), the ratios (%) of the number of proteins in the case where the difference is greater than −0.005 are plotted for each of the microorganisms.

FIG. 6A shows the bands of all the proteins, and FIG. 6B shows the bands of proteins with an esterase activity of each microorganism. GK, BC, BH, BS and OI in the respective figures represent the respective microorganisms, and with regard to the respective lanes 1 to 3 for each of the microorganisms, lane 1 corresponds to a sample without heat treatment, lane 2 corresponds to a sample with heat treatment at 60° C. for 10 minutes, and lane 3 corresponds to a sample with heat treatment at 70° C. for 10 minutes.

FIG. 7A shows the native-PAGE patterns of Hag, and FIG. 7B shows the native-PAGE patterns of GroES. GK, BC, BH, BS and OI in the respective figures represent each of the microorganisms, and with regard to the respective lanes 1 to 3 for each of the microorganisms, lane 1 corresponds to a sample without heat treatment, lane 2 corresponds to a sample with heat treatment at 60° C. for 10 minutes, and lane 3 corresponds to a sample with heat treatment at 70° C. for 10 minutes.

FIG. 10, consisting of FIGS. 10A through 10O, is a color version of Table 1 showing the prediction of thermostability of proteins possessing one-to one correspondence among 5 species of Bacillus.

DETAILED DESCRIPTION OF THE INVENTION

The method of the invention of judging whether or not a test protein has thermostability will be explained.

It is known that there is a correlation between the amino acid compositions of all the proteins deduced from the genome sequence of a microorganism whose complete nucleotide sequences have been determined and the growth temperature of the microorganism. In particular, it is known that the correlation is significantly observed in hyper thermophilic archaebacteria (Archaea) that grows at over 80° C. and in some bacteria. However, almost all the hyper thermophilic bacteria whose complete genome sequences have been determined belongs to Archaea, and detail investigation whether the correlation is specific to Archaea or is a characteristic of thermophilic bacteria has not been carried out. In a similar way, with regard to some thermophilic bacteria whose genome sequence determination has been completed, there are no mesophilic or non-thermostable bacteria closely related to the thermophilic bacteria, or if there is, there is no genome sequence information thereof. Therefore, it was difficult to accurately determine whether the characteristic of the amino acid composition observed in the thermophilic bacteria is indeed a characteristic specific to thermophilic bacteria or it simply reflects a specificity of the species.

In order to accurately determine such a correlation, the inventors decided to investigate the correlation between genome sequence information and thermostability by focusing on Bacillus-related species in which thermophilic bacteria whose upper limit temperature for growth is approximately 70° C. and mesophilic bacteria whose upper limit temperature for growth varies exist in the same genus and a closely related genus. Among the Bacillus-related species, the complete genome sequences of 4 species of mesophilic bacteria, B. subtilis, B. halodurans, O. iheyensis and B. cereus have been revealed, however, the complete genome information of thermophilic Bacillus-related species has not been analyzed.

Therefore, it was decided that the genome of G. kaustophilus HTA426 (hereinafter abbreviated as GK), which is one species of thermophilic G. kaustophilus would be analyzed. This microorganism was obtained from the deep-sea of Mariana Trench. Its upper limit temperature for growth is 74° C.

Figure 1:
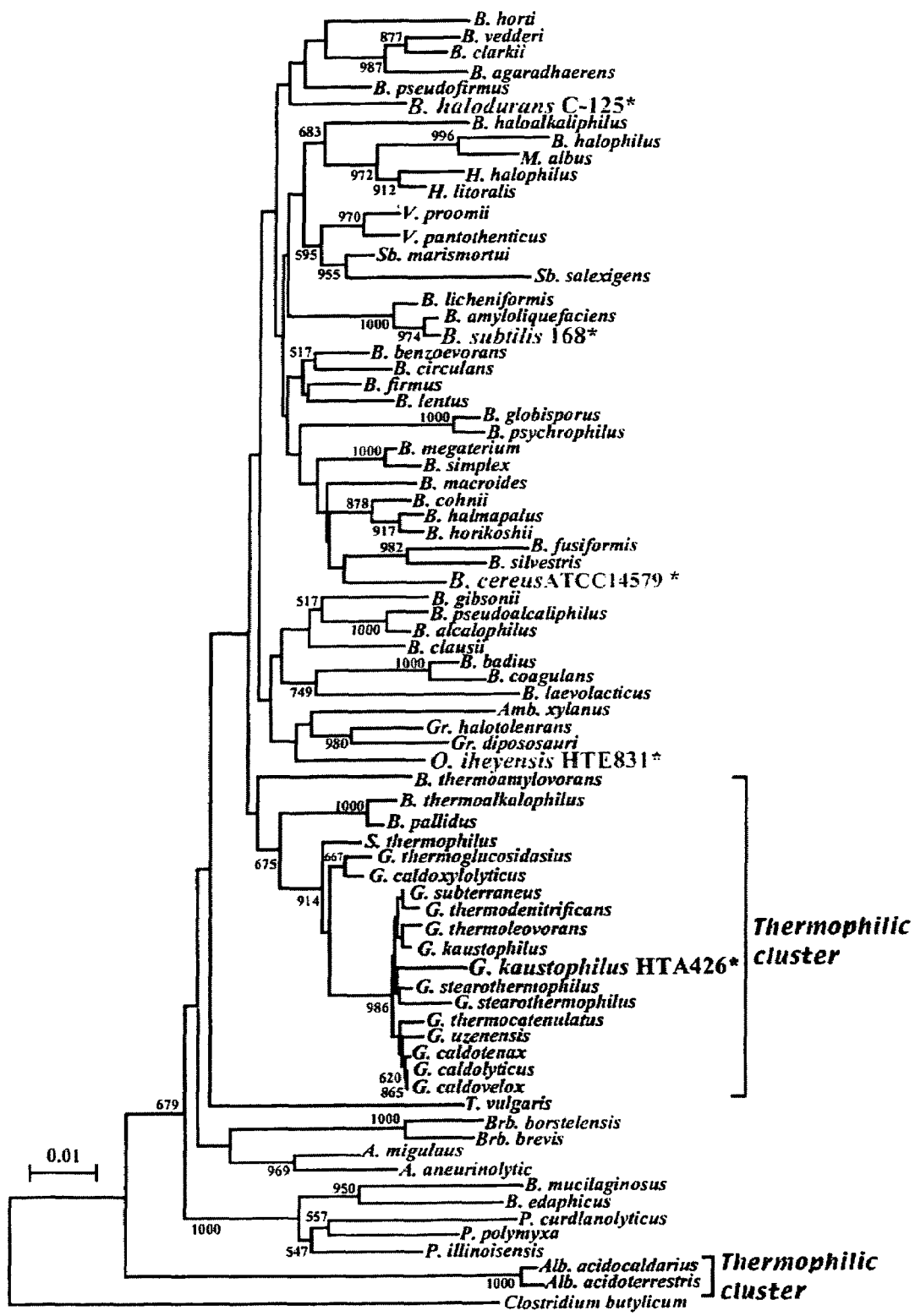
FIG. 1 is a phylogenetic tree created by the neighbor-joining method based on 16S rDNA sequences of *Bacillus*-related species used in a method of the invention as an example.

A phylogenetic tree created by the neighbor-joining method based on 16S rDNA sequences of these Bacillus-related species is shown in FIG. 1. The bar in the lower left in FIG. 1 indicates 0.01 Knuc unit. The part indicated with the lower line (indicated in red in the original figure) indicates that they are thermophilic bacteria. The 5 species of microorganisms, from the upper-side, B. halodurans C-125 (hereinafter abbreviated as BH), B. subtilis 168 (hereinafter abbreviated as BS), B. cereus ATCC14579 (hereinafter abbreviated as BC), O. iheyensis HTE831 (hereinafter abbreviated as OI) and G. kaustophilus HTA426 (hereinafter abbreviated as GK) used in the following analysis are marked with asterisks at the upper right thereof.

First, the inventors determined the complete nucleotide sequence of the genome sequence of thermophilic G. kaustophilus. Next, they analyzed the amino acid compositions of the proteins retained by the 5 species of microorganisms including the G. kaustophilus (GK) and 120 species of microorganisms whose complete genome sequences have been known so far by a principal component analysis (PCA). As a result, as is conventionally known, it was observed that the PC1 shows a strong correlation with the GC content and the PC2 shows a strong correlation with the upper limit temperature for growth in whole.

Figure 2:
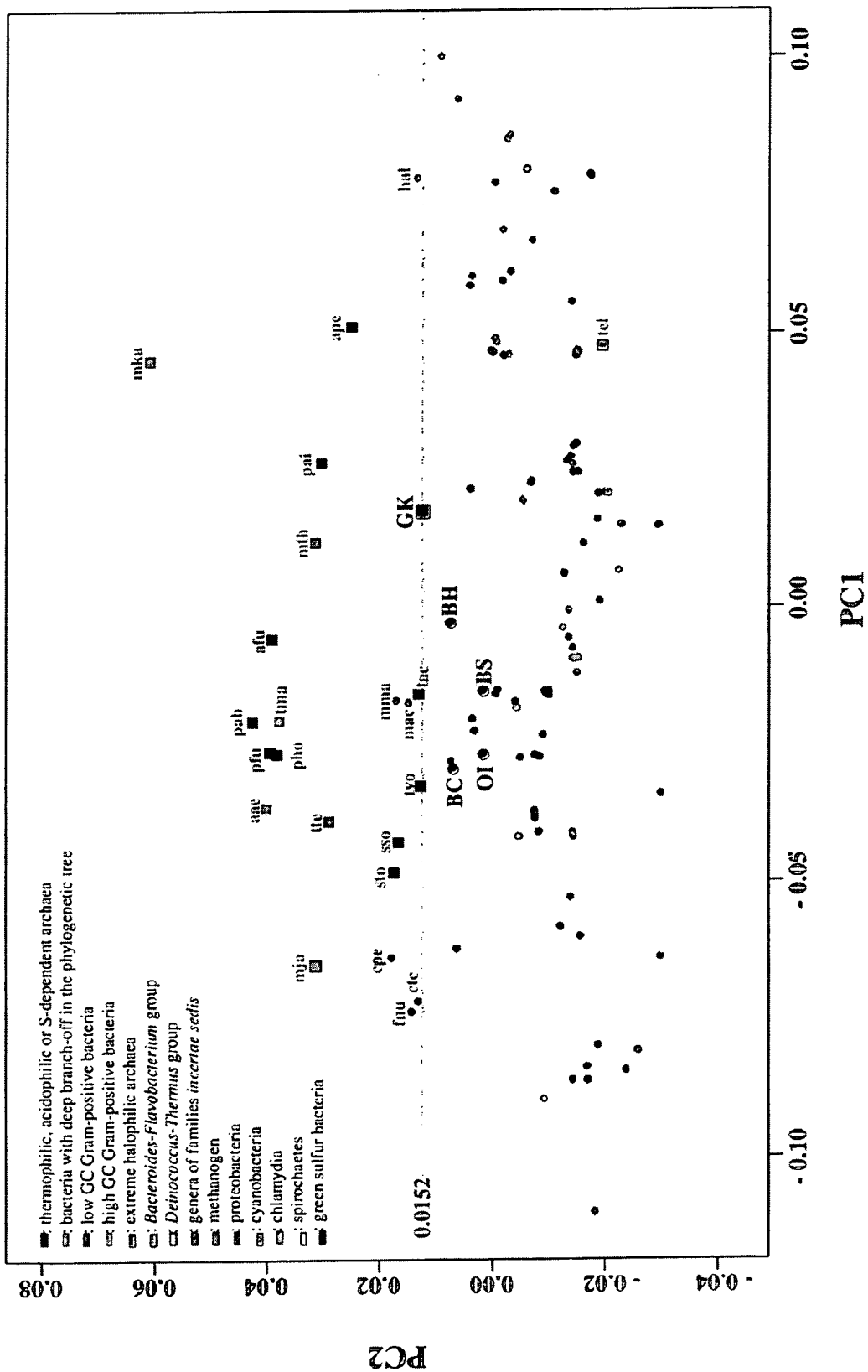
FIG. 2 is a colored graph showing the results of analyzing the amino acid compositions of proteins retained by 120 species of microorganisms whose complete genome sequences have been known so far by a principal component analysis (PCA). The first principle component (PC1) was defined as the GC content and the second principal component (PC2) was defined as the upper limit temperature for growth.

This result is shown in FIG. 2. The original figure of FIG. 2 is a colored graph. The horizontal axis represents the analytical values of the GC content (PC1), and the vertical axis represents the analytical values of the upper limit temperature for growth (PC2). The PCA performed here was in accordance with a usual method in statistics. The red square (black in the black and white figure) indicates thermophilic bacteria, the blue (black in the black and white figure) indicates Gram-positive bacteria with low GC content, and the green (slightly gray in the black and white figure) indicates Gram-positive bacteria with high GC content. The line at 0.0152 of the PC2 score indicates the boundary between thermophilic bacteria (upper side) and mesophilic bacteria (lower side).

In addition, even if it is limited to the Bacillus-related species, a correlation between the second principal component score and the upper limit temperature for growth was observed. However, the result was obtained by using the average amino acid composition of the entire bacteria, and when considering the individual proteins, they were widely scattered; therefore, the correlation was not so clear.

Accordingly, the inventors first calculated the thermostability index of each protein for the 5 species of microorganisms related to the genus Bacillus used in the analysis by multiplying an eigenvector corresponding to the second principal component by an amino acid composition as a weighting factor.

The PCA based on the amino acid compositions used here was carried out by obtaining the genome data of 119 species of microorganisms from the database at NCBI, and using the protein sequences identified in the genomes of 120 species including the obtained genomes of 119 species and the genome of G. kaustophilus HTA426, which had been determined in the invention. From these sequences, a sequence with a sequence length of less than 50 amino acids was excluded, further a protein which had been predicted to contain 2 or more transmembrane domains by the PSORT program was also excluded. By using the sequences of the remaining proteins, an average amino acid composition was calculated on a species basis, a matrix in which each row and column corresponds to the species and an amino acid, respectively, was input, and a principal component analysis was performed using the princomp function in the R statistical analysis package.

Subsequently, based on the results, the differences between the principal component score of a corresponding protein of thermophilic *G. kaustophilus* and those of the 4 species of mesophilic bacteria were calculated. This grouping was performed based on an orthologous relationship deduced from a homology search result, and analysis was performed by using a protein having one-to-one correspondence as a target (Kreil D. P. and Ouzounis, C. A. (2001), Identification of thermophilic species by the amino acid compositions deduced from their genome. Nucleic acids Res. 29, 1608-1615).

The selected 965 proteins are a protein which does not contain 2 or more transmembrane domains, and 965 proteins which are common in the 5 species were extracted from the genome server of *G. stearothermophilus* (hereinafter abbreviated as GS) which has substantially the same upper limit temperature for growth as GK. The judgment whether or not a protein contains 2 or more transmembrane domains was performed by the PSORT program (Nakai, K. & Horton, P., PSORT: Trends Biochem. Sci., 24, 34-36 (1999)).

The values of the calculated "principal component score" from the result are shown in Table 1, shown in color in FIGS. 10A-10O. Each of the columns of the tables corresponds to, from the left, "GK ID" indicating an identification signal based on GK, "category" indicating the classification of each protein, "annotation" indicating the name or the like of each protein, and in the right side, the ID signal of each of the 5 species of microorganisms and the value of the "principal component score", being placed in the order of GK, BC, BH, BS and OI from the left. With regard to the color of the identification signal of each microorganism, (see FIGS. 10A-10O), red indicates the case in which the difference in the "principal component scores" of corresponding protein of GK and each of the other species (difference=(each score for each microorganism)−(each score for GK)) is −0.005 or lower, blue indicates the case in which the difference is −0.010 or lower, green indicates the case in which the difference is −0.015 or lower, and no color indicates the case in which the difference is greater than −0.015.

As is clear from the results, it has been demonstrated that even if a clear correlation cannot be observed in all the microorganisms, by comparing individual proteins corresponding to each other, there is a case where a clear correlation exists. In order to clarify it more clearly, the correlation between GK and each of the microorganisms is shown in a graph.

Figure 3:
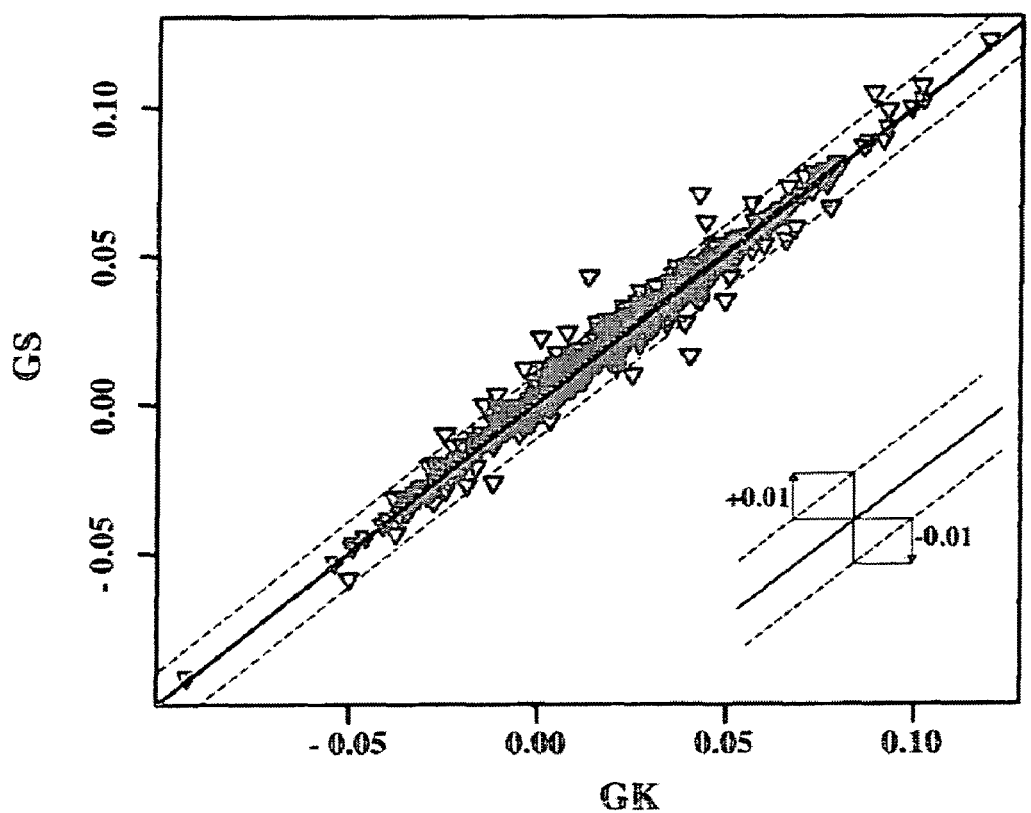
FIG. 3 shows a correlation chart based on the value of the "principal component score" of each protein for *Geobacillus stearothermophilus* (GS), which has substantially the same upper limit temperature for growth as that of thermophilic *Geobacillus kaustophilus* (GK).

In order to make a graph, an orthologous grouping with *G. stearothermophilus* (GS), which has substantially the same upper limit temperature for growth as GK was performed as follows. A draft genome sequence of GS was obtained from the FTP site at the University of Oklahoma. By using each translated sequence of GK as a query, a similar sequence was searched against these contig sequences with the TBLASTN program, and the resulting sequence with the best score was taken as an orthologue when it covered 70% or more of the length of the query sequence with 70% or more identity. Next, with regard to GK and GS, a correlation chart based on the value of the "principal component score" of each protein is shown in FIG. 3. In FIG. 3, the horizontal axis represents the values of the "principal component score" of GK, and the vertical axis represents the values of the "principal component score" of GS. The solid line in the graph indicates that both values are the same, and the dashed lines indicate the range within ±0.01 from the solid line. In this way, it is found that in the case of comparing proteins among thermophilic bacteria, the values of the "principal component scores" of the respective proteins have an extremely strong correlation. Similarly, graphs showing correlations of GK with mesophilic bacteria, BC, BH, BS and OI are shown in FIGS. 4A to 4D, respectively. FIG. 4A shows the correlation of GK with BC, FIG. 4B shows the correlation of GK with BH, FIG. 4C shows the correlation of GK with BS and FIG. 4D shows the correlation of GK with OI. The horizontal axes of the respective graphs represent the values of the "principal component score" for GK, and the vertical axes of the respective graphs represent the values of the "principal component score" for each mesophilic bacterium, respectively. From these graphs, it is found that with regard to mesophilic bacteria, some proteins show a good correlation with those of GK, but some proteins show completely different values depending on the types of the proteins.

With regard to the correlation of GK with GS, almost all the proteins show a strong correlation, however, comparison of GK with the mesophilic bacteria demonstrates that some proteins show almost no correlation. It might be considered that this is because the proteins do not have thermostability. On the contrary, mesophilic bacteria lack thermostability as a whole, however, it might be considered that not all the proteins produced by the microorganisms lack thermostability, but what lacks thermostability is some of the proteins. Suppose a protein that lacked thermostability was essential to life, even if all the other proteins have thermostability, the microorganism would no longer have thermostability as a whole organism.

This is a new finding in the invention of the inventors. In other words, conventionally, in the case of searching a thermostable protein, the search was performed by screening a thermostable microorganism. This is because a thermostable organism has a thermostable protein, otherwise, it cannot maintain its life under a high temperature condition. However, it is not always the case where all the proteins produced by a mesophilic bacterium must lack thermostability. It is not always the case where, even if a mesophilic bacterium produces a thermostable protein, a problem on maintaining its life will occur. It is quite considerable that the reason why a mesophilic bacterium is not thermostable is that not all the proteins lack thermostability, but a protein essential to life lost thermostability.

Figure 4:
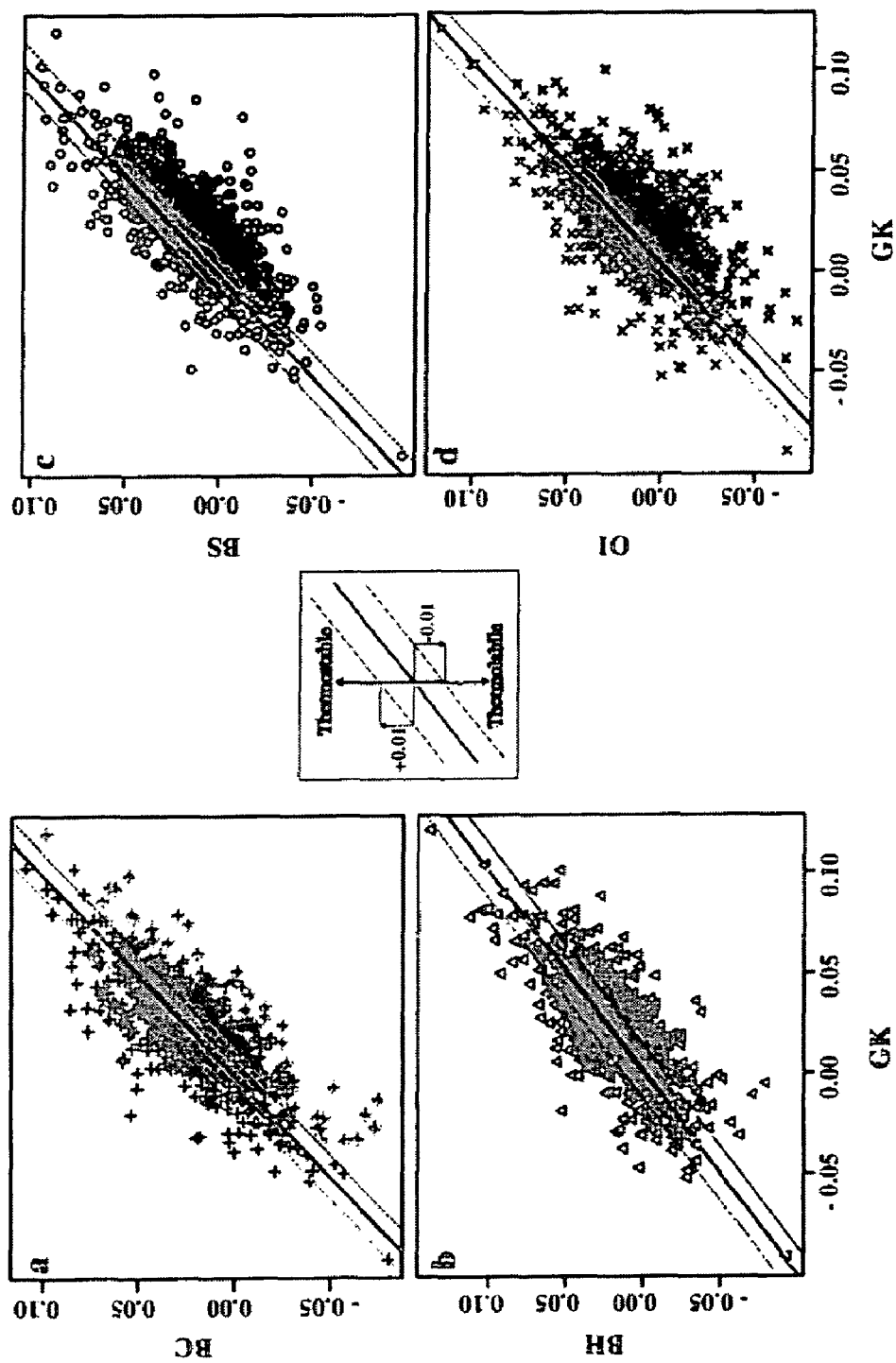
FIGS. 4A to 4D are graphs showing the correlations between thermophilic *G. kaustophilus* (GK) and mesophilic bacteria, *Bacillus cereus* (BC) (FIG. 4A), *Bacillus halodurans* (BH) (FIG. 4B), *Bacillus subtilis* (BS) (FIG. 4C) and *Oceanobacillus iheyensis* (OI) (FIG. 4D), respectively. The horizontal axes of the respective graphs represent the values of the "principal component score" of GK, and the vertical axes of the respective graphs represent the values of the "principal component score" of each mesophilic bacterium, respectively.

The results shown in Table 1 and FIG. 4 indicate the possibility that even a mesophilic bacterium produces a similar thermostable protein, which is produced by a thermophilic bacterium.

Figure 5:
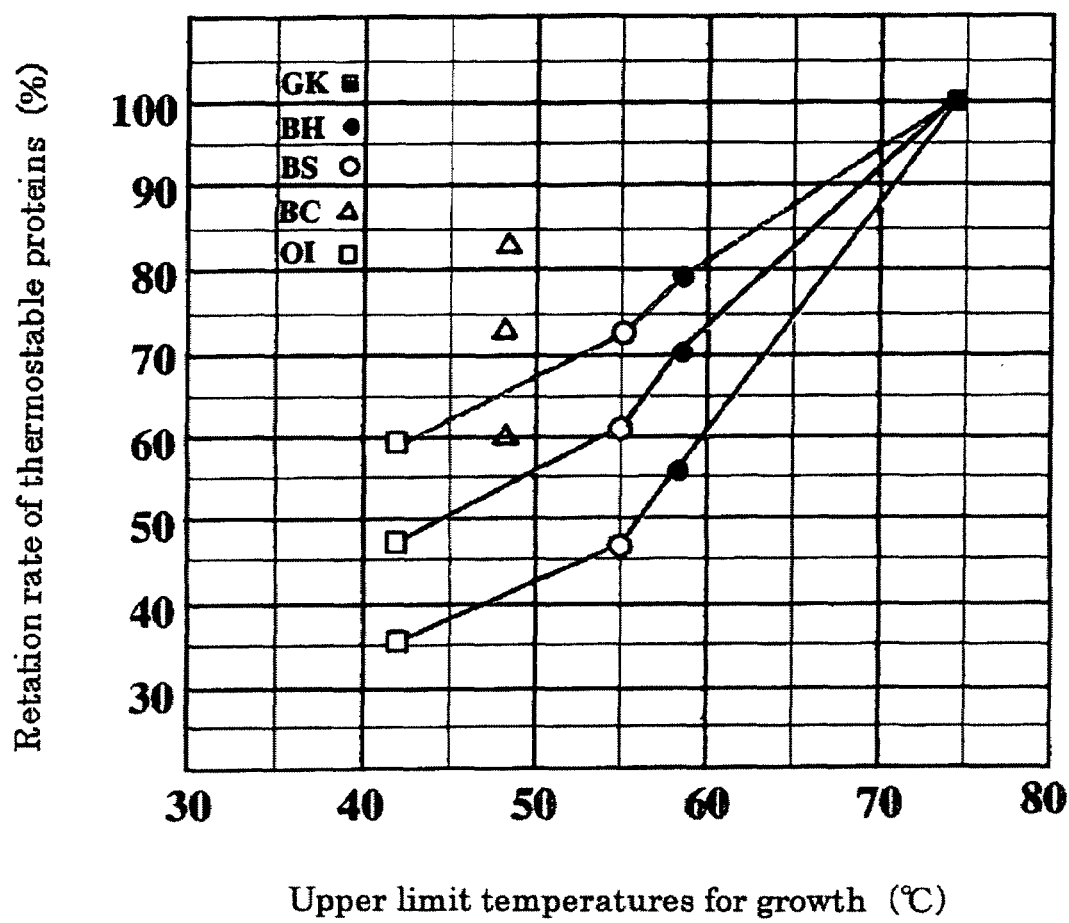
FIG. 5 is a graph summarizing the relationship between the upper limit temperatures for growth of the respective microorganisms, GK (closed square ■), BC (open triangle Δ), BH (closed circle ●), BS (open circle ○) and OI (open square □) and the ratio of the proteins among the 965 proteins in the case where the difference in the values of the "principal component scores" between GK and each of the other microorganisms varies.

These results are summarized based on the correlation with the upper limit temperatures for growth of the respective microorganisms and shown in FIG. 5. In FIG. 5, the horizontal axis represents the temperature and the vertical axis represents the ratio (%). In the graph, the closed square (■) represents GK, the closed circle (●) represents BH, the open circle (○) represents BS, the open triangle (△) represents BC and the open square (□) represents OI. On the horizontal axis, the upper limit temperatures for growth of the respective microorganisms are plotted. On the vertical axis, with regard to the upper line (indicated in green in the original figure), the ratios (%), relative to all the 965 proteins, of the number of proteins in the case where the difference in the values of the "principal component scores" between GK and each of the other microorganisms is greater than −0.015 are plotted for each of the microorganisms, with regard to the line in the middle (indicated in blue in the original figure), the ratios (%) of the number of proteins in the case where the difference is greater than −0.010 are plotted for each of the microorganisms, and with regard to the lower line (indicated in red in the original figure), the ratios (%) of the number of proteins in the case where the difference is greater than −0.005 are plotted for each of the microorganisms. A protein in the case where the difference in the values of the "principal component scores" is greater than −0.015 (i.e., −0.015 or higher, the absolute value becomes small, however, it is a minus number, therefore, it becomes large, hereinafter the same as above) is defined as a thermostable protein, and the number of proteins of these bacteria, BC, BH, BS and OI and the ratio are summarized and shown in Table 2.

Figure 6:
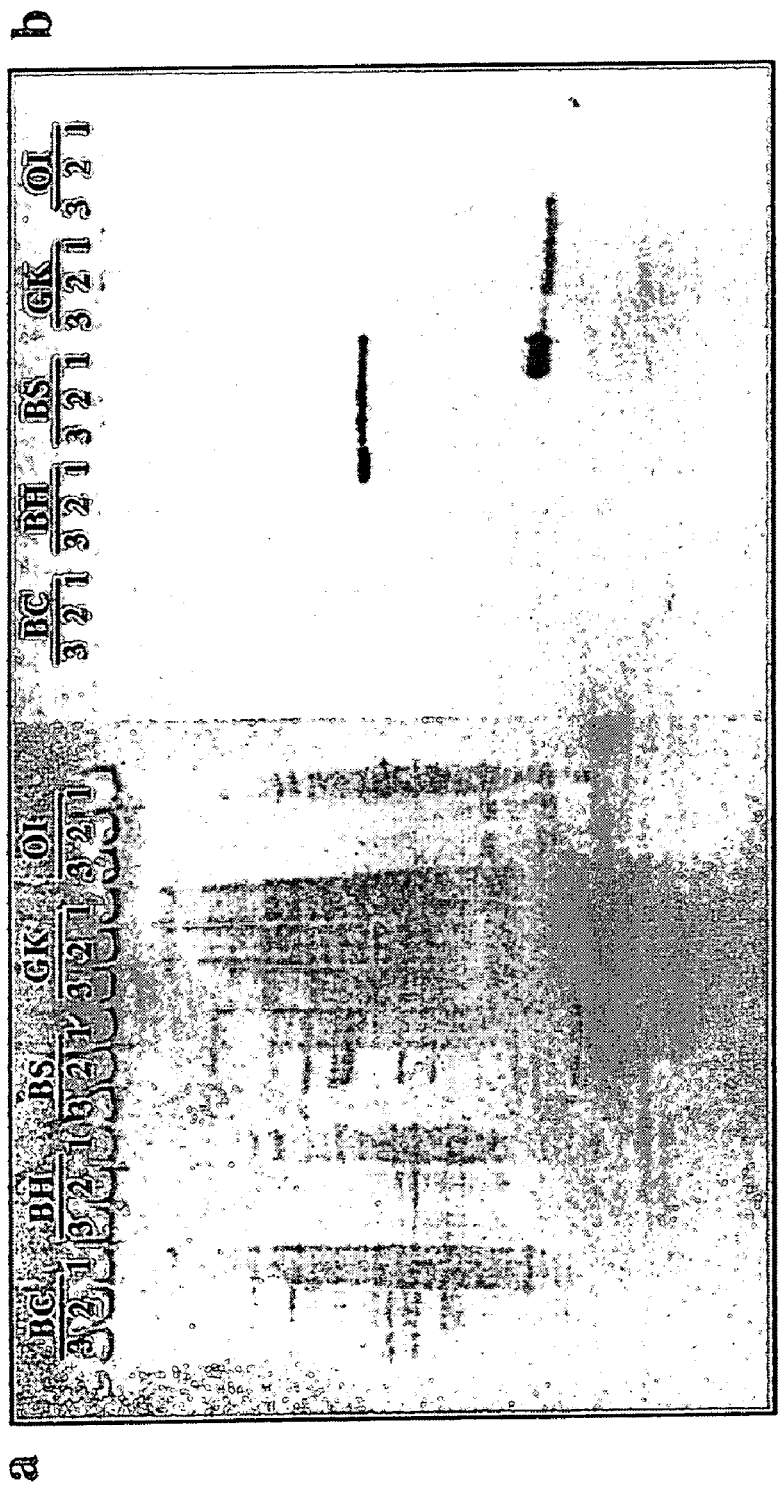
FIGS. 6A and 6B are photographs substituted for a drawing, which show the results of examining the native-PAGE patterns after separating the proteins of the respective microorganisms, GK, BC, BH, BS and OI.

Subsequently, in order to verify the foregoing results, proteins were isolated from these microorganisms, and subjected to the following treatments: (1) no heat treatment, (2) heat treatment at 60° C. for 10 minutes, or (3) heat treatment at 70° C. for 10 minutes, respectively, and the native-PAGE patterns were examined. The results are shown in the photographs substituted for a drawing in FIGS. 6A and 6B. FIG. 6A shows the native-PAGE patterns of all the proteins stained with Coomassie Brilliant Blue. From the result, with regard to GK, a thermophilic bacterium, almost all the protein bands could be confirmed even after the heat treatment (lanes 2 and 3), however, it is found that with regard to the other 4 species of mesophilic bacteria, a lot of protein bands were lost by the heat treatment. What is important here is that not all the protein bands were lost. It is found that some protein bands remained without being lost after the heat treatment. The

TABLE 2

Summary of prediction of thermostable proteins from bacteria belonging to mesophilic Bacillus species based on the principal component analysis

| prediction | BC (number) | BC (%) | BH (number) | BH (%) | BS (number) | BS (%) | OI (number) | OI (%) |
|---|---|---|---|---|---|---|---|---|
| − | 159 | 16.5 | 202 | 20.9 | 269 | 27.9 | 391 | 40.5 |
| + | 95 | 9.8 | 83 | 8.6 | 108 | 11.2 | 110 | 11.4 |
| ++ | 128 | 13.3 | 145 | 15 | 135 | 14 | 120 | 12.4 |
| +++ | 583 | 60.4 | 535 | 55.4 | 453 | 46.9 | 344 | 35.6 |
| ++, +++ | 711 | 73.7 | 680 | 70.5 | 688 | 60.9 | 464 | 48.1 |
| +, ++, +++ | 806 | 83.5 | 763 | 79.1 | 696 | 72.1 | 574 | 59.5 |

The Table 2 summarizes the results of prediction of thermostable proteins from bacteria belonging to mesophilic Bacillus species based on the principal component analysis. In Table 2, "−" indicates the case where the difference in PC2 values of the proteins of each microorganism and GK is lower than −0.015, thereby being judged lack of thermostability, and "+", "++", "+++" indicate the cases where the difference is greater than −0.015, −0.01 and −0.005, respectively, thereby being judged presence of thermostability. In Table 2, "++, +++" corresponds to the sum of the numbers of "++" and "+++", and "+, ++, +++" corresponds to the sum of the numbers of "+", "++" and "+++". Table 2 summarizes the results of analysis based on 965 orthologues having one-to-one correspondence among the 5 Bacillus-related species.

As a result, as shown in Table 2, the ratios of the proteins predicted to be thermostable among the 965 proteins are 83.5% for BC, 79.1% for BH, 72.1% for BS, and 59.5% for OI, respectively. In the graph of FIG. 5, BC (Δ) shows somewhat abnormal values, however, it is found that the other three species show similar tendencies. In other words, it is demonstrated that the more proteins with a value of "principal component score" equal to that of a protein produced by a thermophilic bacterium produces a microorganism, the higher becomes the upper limit temperature for growth of the microorganism. For example, with regard to OI that produces the fewest proteins with a value of "principal component score" equal to that of a protein produced by a thermophilic bacterium, its upper limit temperature for growth is the lowest among these microorganisms. Incidentally, BC (Δ) has the largest amount of the same types of proteins among the 4 mesophilic bacteria, however, it is found that its upper limit temperature for growth is abnormally low. It is considered that this is because a protein essential to life retained by BC happened to lose thermostability.

results demonstrate that not all the proteins produced even by a mesophilic bacterium are not thermostable.

FIG. 6B shows the results of detecting the bands of proteins with an esterase (EC 3.1.1.1) activity by active staining after all the proteins of each microorganism were separated by native PAGE in the same manner as in FIG. 6A. BC, BH, BS, GK and OI in the respective figures represent the respective microorganisms. With regard to the respective lanes 1 to 3 for each of the microorganisms, lane 1 corresponds to a sample without heat treatment, lane 2 corresponds to a sample with heat treatment at 60° C. for 10 minutes, and lane 3 corresponds to a sample with heat treatment at 70° C. for 10 minutes. In the case of OI in FIG. 6B with regard to esterase, the bands were lost by the heat treatment at 60° C. (lane 2). In addition, in the case of BC, the main band which had been most intensively stained in the case where heat treatment had not been applied was lost by the heat treatment. However, in the case of BS, the bands were not lost by the heat treatment, and in the case of BH, the bands, although they were faint, remained without being lost even by the heat treatment at 60° C.

Figure 7:
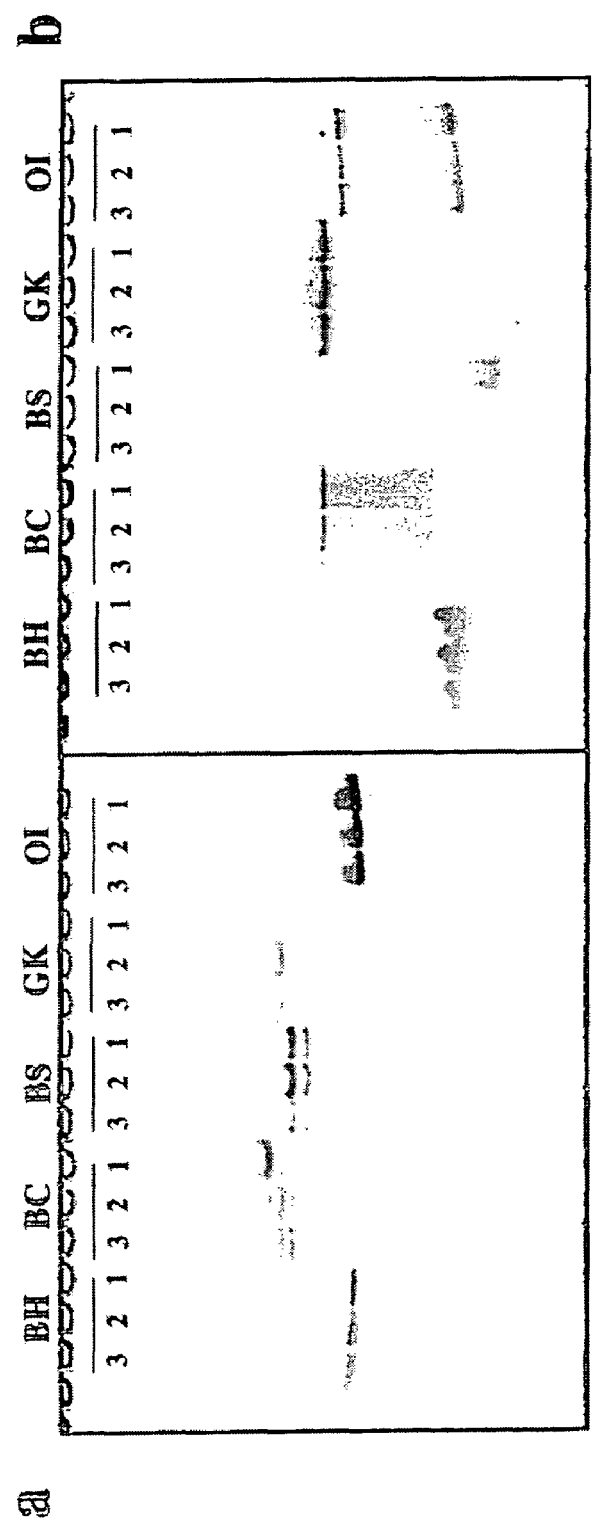
FIGS. 7A and 7B are photographs substituted for a drawing, which show the results of examining the native-PAGE patterns after separating Hag and GroES proteins of the respective microorganisms, GK, BC, BH, BS and OI.

In addition, with regard to GroES that is one of the proteins essential to growth for B. subtilis, and Hag (Flagellin) that is one of the representative proteins retained commonly by Bacillus-related species, the genes encoding these proteins were amplified by PCR from the respective microorganisms, and by using the cloned genes with E. coli, the same verification of thermostability as above was carried out. The cloned and purified proteins were subjected to the following treatments: (1) no heat treatment, (2) heat treatment at 60° C. for 10 minutes, and (3) heat treatment at 70° C. for 10 minutes, respectively, and then the native-PAGE patterns were examined. The results are shown in the photographs substituted for a drawing in FIGS. 7A and 7B. FIG. 7A shows the native- PAGE patterns of Hag, and FIG. 7B shows the native-PAGE patterns of GroES, which were obtained by separating the proteins with native PAGE and staining them with Coomassie Brilliant Blue. BC, BH, BS, GK and OI in the respective figures represent the respective microorganisms, and with regard to the respective lanes 1 to 3 for each of the microorganisms, lane 1 corresponds to a sample without heat treatment, lane 2 corresponds to a sample with heat treatment at 60° C. for 10 minutes, and lane 3 corresponds to a sample with heat treatment at 70° C. for 10 minutes.

Another problem is what types of proteins are thermostable. It was found that, in the case of esterase, it is difficult to specify which band corresponds to esterase specifically because plural proteins might be stained by a staining method, therefore, the inventors decided to focus on the proteins, Hag and GroES. The results of verification of Hag and GroES of each microorganism are shown in FIGS. 7A and 7B, respectively. These proteins have the identification signal of GK, GK3131 (Hag) and GK0248 (GroES) described in the Tables above.

The values of the principal component scores of these proteins for each microorganism are as follows: with regard to Hag, (GK, −0.0513; BC, −0.0622; BH, −0.0567; BS, −0.0578; OI, −0.0528) (see Table 1), with regard to GroES, (GK, 0.1018; BC, 0.0826; BH, 0.1012; BS, 0.0940; OI, 0.0988) (see Table 1). These are summarized and shown in the following Table 3.

TABLE 3

| | GK | BC | BH | BS | OI |
|---|---|---|---|---|---|
| Hag (GK3131) | −0.0513 | −0.0622 | −0.0567 | −0.0578 | −0.0528 |
| difference with GK | | 0.0109 | 0.0054 | 0.0065 | 0.0015 |
| GroES (GK0248) | 0.1018 | 0.0826 | 0.1012 | 0.0940 | 0.0988 |
| difference with GK | | 0.0192 | 0.0006 | 0.0078 | 0.0030 |

With regard to Hag protein, the bands were maintained even by the heat treatment at 70° C. in substantially the same manner as in the case of no heat treatment for all microorganisms except for BC. With regard to GroES protein, only faint bands were confirmed by the heat treatment at 60° C. or higher for BC and BS, therefore, it is considered that the proteins were decomposed by the heat treatment. For the other microorganisms, BH, OI and GK, the bands were maintained in the same manner as in the case of no heat treatment. These results demonstrated that in mesophilic bacteria, some proteins have thermostability, and some proteins do not depending on their types.

Subsequently, the protein bands remaining without being lost after the heat treatment at 70° C. for 10 minutes shown in FIG. 6A were cut out from the gel in the order from the upper part, and identification of the proteins contained in each band was performed using LC/MS/MS. The results are shown in Tables 4 to 7.

TABLE 4

List of thermostable proteins from *Bacillus subtilis* confirmed experimentally and its comparison with computational prediction of the thermostability

| Gene name of BS | Product name | Corresponding gene name of GK | Result of Prediction | Number of amino aids of the product | Difference in scores of principal Component analysis between gk and bs |
|---|---|---|---|---|---|
| nadE | NH3-dependent NAD+ synthetase (sporulation protein out B) (general stress protein 38) | GK2596 | − | 272 | −0.0340 |
| yjcG | hypothetical protein (yjcG) | GK0864 | − | 171 | −0.0200 |
| codY | transcriptional regulator | GK1215 | − | 259 | −0.0270 |
| ymfG | processing protease | GK1287 | − | 240 | −0.0420 |
| deoD | purine nucleoside phosphorylase | GK1580 | − | 233 | −0.0190 |
| ypfD | ribosomal protein S1 homolog (jofD) | GK2225 | − | 382 | −0.0155 |
| efp | elongation factor P | GK2410 | − | 185 | −0.0152 |
| yqhT | Xaa-Pro dipeptidase | GK2411 | − | 353 | −0.0233 |
| etfB | electron transfer flavoprotein (beta subunit) | GK2687 | − | 257 | −0.0205 |
| ytdI | hypothetical protein | GK2792 | − | 267 | −0.0243 |
| tyrS | tyrosyl-tRNA synthetase | GK2803 | − | 422 | −0.0156 |
| yugJ | NADH-dependent butanol dehydrogenase | GK2925 | − | 387 | −0.0290 |
| eno | enolase | GK3054 | − | 430 | −0.0184 |
| hutI | imidazolone-5-propionate hydrolase | GK1368 | − | 421 | −0.0296 |
| clpC | class III stress response-related ATPase | GK0078 | + | 810 | −0.0132 |
| rplB | ribosomal protein L2 | GK0109 | + | 277 | −0.0106 |
| acoB | acetoin dehydrogenase E1 component (TPP-dependent beta subunit) | GK0711 | + | 342 | −0.0112 |
| pycA | pyruvate carboxylase | GK1079 | + | 1148 | −0.0147 |
| ftsZ | cell-division initiation protein | GK1125 | + | 382 | −0.0113 |
| sucD | succinyl-CoA synthetase (alpha subunit) | GK1209 | + | 300 | −0.0111 |
| pnpA | polynucleotide phosphorylase (PNPase) | GK1269 | + | 705 | −0.0124 |
| hbs | non-specific DNA-binding protein HBsu | GK2215 | + | 92 | −0.0118 |
| drm | phosphodeoxyribomutase | GK2314 | + | 394 | −0.0144 |
| yqjM | NADH-dependent flavin oxidoreductase | GK2332 | + | 338 | −0.0101 |
| zwf | glucose-6-phosphate 1-dehydrogenase (pentose | GK2334 | + | 489 | −0.0147 |
| bcd | leucine dehydrogenase | GK2381 | + | 364 | −0.0109 |
| aspS | aspartyl-tRNA synthetase | GK2572 | + | 592 | −0.0108 |
| queA | S-adenosylmethionine tRNA ribosyltransferase | GK2588 | + | 342 | −0.0132 |
| yufO | ABC transporter | GK1284 | + | 510 | −0.0137 |
| yurX | hypothetical protein | GK2994 | + | 437 | −0.0118 |
| citG | fumarate hydratase | GK0250 | + | 462 | −0.0114 |
| hprK | hypothetical protein | GK3082 | + | 310 | −0.0133 |
| nfrA | NADPH-flavin oxidoreductase(ipa-43d) | GK1652 | + | 249 | −0.0141 |

TABLE 4-continued

List of thermostable proteins from *Bacillus subtilis* confirmed experimentally and its comparison with computational prediction of the thermostability

| Gene name of BS | Product name | Corresponding gene name of GK | Result of Prediction | Number of amino aids of the product | Difference in scores of principal Component analysis between gk and bs |
|---|---|---|---|---|---|
| mmsA | methylmalonate-semialdehyde dehydrogenase | GK1887 | + | 487 | −0.0104 |
| metS | methionyl-tRNA synthetase | GK0031 | ++ | 664 | −0.0052 |
| rplL | ribosomal protein L12 (BL9) | GK0096 | ++ | 123 | −0.0086 |
| rpoA | RNA polymerase (alpha subunit) | GK0133 | ++ | 314 | −0.0064 |
| ylbA | hypothetical protein (ylbA) | GK1089 | ++ | 120 | −0.0081 |
| proS | prolyl-tRNA synthetase | GK1257 | ++ | 564 | −0.0052 |
| infB | translation initiation factor IF-2 | GK1263 | ++ | 716 | −0.0065 |
| citB | aconitate hydratase | GK1347 | ++ | 909 | −0.0075 |
| odhA | 2-oxoglutarate dehydrogenase (E1 subunit) | GK1023 | ++ | 941 | −0.0099 |
| ribH | riboflavin synthase (beta subunit) | GK2294 | ++ | 154 | −0.0066 |
| yqkF | hypothetical proteins | GK2321 | ++ | 306 | −0.0060 |
| hemL | glutamate-1-semialdehyde 2,1-aminotransferase | GK2642 | ++ | 430 | −0.0081 |
| pyk | pyruvate kinase | GK2739 | ++ | 585 | −0.0074 |
| hag | flagellin protein | GK3131 | ++ | 304 | −0.0063 |
| rocF | arginase | GK0149 | ++ | 296 | −0.0059 |
| guaB | inositol-monophosphate dehydrogenase | GK0009 | +++ | 488 | −0.0003 |
| hprT | hypoxanthine-guanine phosphoribosyltransferase | GK0061 | +++ | 180 | 0.0098 |
| gltX | glutamyl-tRNA synthetase | GK0083 | +++ | 483 | 0.0061 |
| rpoB | RNA polymerase (beta subunit) | GK0098 | +++ | 1193 | −0.0021 |
| fusA | elongation factor G | GK0103 | +++ | 692 | 0.0066 |
| tufA | elongation factor Tu | GK0104 | +++ | 396 | 0.0041 |
| ybbT | phosphoglucomutase (glycolysis) | GK0154 | +++ | 448 | 0.0033 |
| groEL | class I heat-shock protein (molecular chaperonin) | GK0249 | +++ | 544 | −0.0003 |
| guaA | GMP synthetase | GK0254 | +++ | 513 | 0.0048 |
| gatB | glutamyl-tRNA(Gln) amidotransferase | GK0283 | +++ | 476 | 0.0071 |
| glpK | glycerol kinase | GK1360 | +++ | 496 | 0.0000 |
| yhxB | phosphomannomutase | GK0570 | +++ | 565 | 0.0067 |
| dat | D-alanine aminotransferase | GK0672 | +++ | 282 | −0.0031 |
| yheA | hypothetical protein (yheA) | GK0640 | +++ | 117 | 0.0429 |
| serC | phosphoserine aminotransferase | GK0649 | +++ | 359 | −0.0041 |
| argF | ornithine carbamoyltransferase | GK0796 | +++ | 319 | −0.0015 |
| yjbG | oligoendopeptidase | GK0822 | +++ | 609 | −0.0038 |
| ykrS | initiation factor eIF-2B (alpha subunit) | GK0949 | +++ | 353 | −0.0035 |
| ptsI | phosphotransferase system (PTS) enzyme I | GK0996 | +++ | 570 | 0.0090 |
| ampS | aminopeptidase | GK2140 | +++ | 410 | 0.0171 |
| pdhB | pyruvate dehydrogenase (E1 beta subunit) | GK1059 | +++ | 325 | −0.0034 |
| pdhD | dihydrolipoamide dehydrogenase E3 subunit of both pyruvate dehydrogenase and 2-oxoglutarate dehydrogenase complexes | GK1061 | +++ | 470 | 0.0072 |
| sucC | succinyl-CoA synthetase (beta chain) | GK1208 | +++ | 385 | −0.0030 |
| tsf | elongation factor Ts | GK1250 | +++ | 293 | −0.0036 |
| nusA | transcription termination (nusA) | GK1260 | +++ | 371 | 0.0195 |
| cinA | competence-damage inducible protein | GK1294 | +++ | 416 | 0.0143 |
| glnA | glutamine synthetase | GK1327 | +++ | 444 | 0.0074 |
| odhB | 2-oxoglutarate dehydrogenase complex | GK1024 | +++ | 417 | 0.0093 |
| asnS | asparaginyl-tRNA synthetase | GK2171 | +++ | 430 | 0.0035 |
| aspB | aspartate aminotransferase | GK2172 | +++ | 393 | 0.0069 |
| panC | pantothenate synthetase | GK2178 | +++ | 286 | 0.0086 |
| ndk | nucleoside diphosphate kinase | GK2209 | +++ | 149 | 0.0069 |
| lysA | diaminopimelate decarboxylase (DAP decarboxylase) | GK2300 | +++ | 439 | −0.0040 |
| yqjI | 6-phosphogluconate dehydrogenase (pentose | GK2344 | +++ | 469 | −0.0042 |
| sodA | superoxide dismutase | GK2457 | +++ | 202 | 0.0028 |
| sigA | RNA polymerase major sigma-43 factor (sigma-A) | GK2482 | +++ | 371 | −0.0007 |
| dnaK | class I heat-shock protein (chaperonin) | GK2504 | +++ | 611 | 0.0084 |
| yrbE | opine catabolism | GK1897 | +++ | 341 | 0.0102 |
| valS | valyl-tRNA synthetase | GK2638 | +++ | 880 | −0.0020 |
| hemB | delta-aminolevulinic acid dehydratase | GK2643 | +++ | 324 | −0.0031 |
| tig | trigger factor (prolyl isomerase) | GK2653 | +++ | 424 | 0.0062 |
| mdh | malate dehydrogenase | GK2734 | +++ | 312 | 0.0003 |
| icd | isocitrate dehydrogenase | GK2735 | +++ | 423 | −0.0047 |
| citZ | citrate synthase II | GK2736 | +++ | 372 | −0.0039 |
| tpx | thiol peroxidase | GK2787 | +++ | 167 | 0.0171 |
| acsA | acetyl-CoA synthetase | GK2806 | +++ | 572 | 0.0007 |
| pckA | phosphoenolpyruvate carboxykinase | GK2850 | +++ | 527 | 0.0113 |
| pgi | glucose-6-phosphate isomerase | GK2924 | +++ | 451 | −0.0047 |
| ald | L-alanine dehydrogenase | GK3448 | +++ | 378 | −0.0037 |
| yumC | thioredoxin reductase | GK2954 | +++ | 332 | 0.0113 |
| yurU | hypothetical protein | GK2991 | +++ | 465 | 0.0069 |
| yurY | ABC transporter (ATP-binding protein) | GK2995 | +++ | 261 | −0.0007 |
| yusJ | butyryl-CoA dehydrogenase | GK3006 | +++ | 594 | −0.0008 |

TABLE 4-continued

List of thermostable proteins from *Bacillus subtilis* confirmed experimentally and its comparison with computational prediction of the thermostability

| Gene name of BS | Product name | Corresponding gene name of GK | Result of Prediction | Number of amino aids of the product | Difference in scores of principal Component analysis between gk and bs |
|---|---|---|---|---|---|
| pgm | phosphoglycerate mutase | GK3055 | +++ | 511 | −0.0048 |
| yvbY | hypothetical protein | GK0393 | +++ | 240 | 0.0240 |
| clpP | ATP-dependent Clp protease proteolytic subunit (class III heat-shock protein) | GK3062 | +++ | 197 | 0.0157 |
| rbsK | ribokinase | GK3230 | +++ | 293 | 0.0075 |
| atpD | ATP synthase (subunit beta) | GK3358 | +++ | 473 | −0.0048 |
| atpA | ATP synthase alpha chain | GK3360 | +++ | 502 | −0.0043 |
| glyA | serine hydroxymethyltransferase | GK3369 | +++ | 415 | 0.0094 |
| ywjH | transaldolase (pentose phosphate) | GK3385 | +++ | 212 | −0.0014 |
| fbaA | fructose-1,6-bisphosphate aldolase | GK3386 | +++ | 285 | −0.0031 |
| pta | phosphotransacetylase | GK3415 | +++ | 323 | 0.0000 |
| fbaB | myo-inositol catabolism (yxdH) | GK1892 | +++ | 278 | 0.0033 |
| iolD | alternate gene name: yxdC~myo-inositol catabolism | GK1888 | +++ | 325 | 0.0157 |
| ahpC | alkyl hydroperoxide reductase (small subunit) | GK2575 | +++ | 187 | 0.0115 |
| ahpF | alkyl hydroperoxide reductase (large subunit) and NADH dehydrogenase | GK2574 | +++ | 509 | 0.0085 |
| purA | adenylosuccinate synthetase | GK3475 | +++ | 430 | −0.0049 |
| yyaF | hypothetical protein | GK3483 | +++ | 366 | −0.0049 |

Difference in scores of principal component analysis between gk and bs
−: <−0.015 to be judjed as lack of thermostability
+: >−0.015 to be judged to have thermostability
++: >−0.010 to be judged to have thermostability
+++: >− to be judged to have thermostability

TABLE 5

List of thermostable proteins from *Bacillus halodurans* confirmed experimentally and its comparison with computational prediction of the thermostability

| Gene name of BH | Product name | Corresponding gene name of GK | Result of Prediction | Number of amino aids of the product | Difference in scores of principal component analysis between gk and bh |
|---|---|---|---|---|---|
| BH3347 | polyribonucleotide nucleotidvltransferase (general stress | GK2927 | − | 138 | −0.0335 |
| BH3556 | enolase (2-phosphoglycerate | GK3054 | − | 429 | −0.0160 |
| BH2469 | succinyl-CoA synthetase (alpha subunit) | GK1209 | + | 302 | −0.0148 |
| BH3053 | trigger factor (prolyl isomerase) | GK2653 | + | 431 | −0.0112 |
| BH3099 | electron transfer flavoprotein (alpha | GK2686 | + | 325 | −0.0133 |
| BH3100 | electron transfer flavoprotein (beta | GK2687 | + | 256 | −0.0134 |
| BH0906 | catalase | GK1710 | ++ | 735 | −0.0098 |
| BH1309 | non-specific DNA-binding protein II | GK2215 | ++ | 90 | −0.0100 |
| BH1409 | superoxide dismutase | GK2457 | ++ | 202 | −0.0088 |
| BH1530 | phosphopentomutase | GK2314 | ++ | 393 | −0.0063 |
| BH3059 | ketol-acid reductoisomerase | GK2659 | ++ | 340 | −0.0070 |
| BH3257 | endo-1,4-beta-glucanase | GK2820 | ++ | 357 | −0.0051 |
| BH3560 | glyceraldehyde-3-phosphate | GK3058 | ++ | 335 | −0.0092 |
| BH0020 | inositol-monophosphate dehydrogenase | GK0009 | +++ | 485 | 0.0005 |
| BH0063 | translation initiation inhibitor | GK0041 | +++ | 124 | 0.0202 |
| BH0122 | 50S ribosomal protein L7/L12 | GK0096 | +++ | 121 | 0.0005 |
| BH0132 | translation elongation factor Tu (EF- | GK0104 | +++ | 396 | 0.0029 |
| BH0562 | class I heat-shock protein (chaperonin) | GK0249 | +++ | 544 | −0.0025 |
| BH0613 | endo-1,4-beta-glucanase | GK1868 | +++ | 807 | 0.0033 |
| BH1018 | stress-and starvation-induced gene controlled by sigma-B | GK2861 | +++ | 146 | −0.0005 |
| BH1149 | unknown conserved protein | GK0640 | +++ | 116 | −0.0008 |
| BH1177 | protein secretion (post-translocation | GK0656 | +++ | 333 | 0.0030 |
| BH1345 | heat-shock protein (activation of DnaK) | GK2505 | +++ | 194 | 0.0185 |
| BH1346 | class I heat-shock protein (chaperonin) | GK2504 | +++ | 614 | −0.0022 |
| BH1385 | ATP-dependent RNA helicase | GK2475 | +++ | 438 | −0.0028 |
| BH1515 | PTS system, glucose-specific enzyme II | GK3446 | +++ | 173 | 0.0004 |
| BH1604 | inorganic pyrophosphatase | GK2246 | +++ | 163 | 0.0049 |
| BH1636 | 30S ribosomal protein S1 | GK2225 | +++ | 383 | −0.0045 |
| BH1654 | nucleoside diphosphate kinase | GK2209 | +++ | 147 | 0.0213 |
| BH2360 | glutamine synthetase | GK1327 | +++ | 449 | 0.0031 |
| BH2426 | elongation factor Ts | GK1250 | +++ | 293 | 0.0235 |
| BH2470 | succinyl-CoA synthetase (beta subunit) | GK1208 | +++ | 386 | 0.0008 |

TABLE 5-continued

List of thermostable proteins from *Bacillus halodurans* confirmed experimentally and its comparison with computational prediction of the thermostability

| Gene name of BH | Product name | Corresponding gene name of GK | Result of Prediction | Number of amino aids of the product | Difference in scores of principal component analysis between gk and bh |
|---|---|---|---|---|---|
| BH2665 | 2-cys peroxiredoxin | GK2575 | +++ | 183 | 0.0110 |
| BH2800 | Xaa-Pro dipeptidase | GK2411 | +++ | 355 | 0.0006 |
| BH3558 | triosephosphate isomerase | GK3056 | +++ | 251 | 0.0162 |
| BH3616 | flagellin | GK3131 | +++ | 272 | −0.0045 |
| BH3786 | fructose-1,6-bisphosphate aldolase | GK3386 | +++ | 287 | −0.0021 |
| BH3793 | DNA-directed RNA polymerase delta | GK3390 | +++ | 164 | 0.0264 |

Difference in scores of principal component analysis between gk and bh
−: <−0.015 to be judjed as lack of thermostability
+: >−0.015 to be judged to have thermostability
++: >−0.010 to be judged to have thermostability
+++: >−0.005 to be judged to have thermostability

TABLE 6

List of thermostable proteins from *Oceanobacillus iheyensis* confirmed experimentally and its comparison with computational prediction of the thermostability

| Gene name of OB | Product name | Corresponding gene name of GK | Result of Prediction | Number of amino aids of the product | Difference in scores of principal component analysis between gk and oi |
|---|---|---|---|---|---|
| OB1216 | thimet oligopeptidase | GK0822 | − | 602 | −0.0179 |
| OB2345 | purine nucleoside phosphorylase | GK1580 | − | 235 | −0.0249 |
| OB1528 | chromosome segregation SMC protein | GK1193 | − | 1188 | −0.0166 |
| OB2002 | transcriptional elongation factor | GK2547 | − | 158 | −0.0169 |
| OB1800 | 30S ribosomal protein S1 | GK2225 | − | 376 | −0.0281 |
| OB1969 | heat shock protein | GK2505 | − | 190 | −0.0235 |
| OB2166 | malate dehydrogenase | GK2734 | + | 312 | −0.0139 |
| OB1414 | pyruvate dehydrogenase E2 | GK1060 | + | 427 | −0.0102 |
| OB0010 | inosine-5'-monophosphate | GK0009 | + | 489 | −0.0137 |
| OB1694 | DNA topoisomerase IV subunit A | GK1750 | + | 816 | −0.0149 |
| OB1896 | Xaa-Pro dipeptidase | GK2411 | + | 353 | −0.0144 |
| OB1367 | hypothetical protein | GK1982 | + | 178 | −0.0148 |
| OB1779 | hypothetical protein | GK2195 | + | 420 | −0.0111 |
| OB2118 | electron transfer flavoprotein alpha | GK2686 | ++ | 323 | −0.0080 |
| OB3225 | stage V sporulation protein N | GK3448 | ++ | 376 | −0.0080 |
| OB1349 | 1-pyrroline-5-carboxylate | GK0187 | ++ | 515 | −0.0053 |
| OB0140 | adenylate kinase | GK0127 | ++ | 215 | −0.0069 |
| OB0656 | class I heat shock protein | GK0249 | ++ | 545 | −0.0054 |
| OB1968 | class I heat shock protein 70 | GK2504 | ++ | 612 | −0.0070 |
| OB0093 | ATP-dependent Clp protease | GK0078 | ++ | 809 | −0.0077 |
| OB1427 | hypothetical protein | GK1076 | ++ | 149 | −0.0067 |
| OB2359 | hypothetical protein | GK2967 | ++ | 172 | −0.0057 |
| OB0002 | DNA-directed DNA polymerase III beta | GK0002 | +++ | 378 | 0.0103 |
| OB2380 | ABC transporter ATP-binding protein | GK2995 | +++ | 261 | −0.0021 |
| OB2117 | thioredoxin | GK2685 | +++ | 104 | 0.0068 |
| OB2119 | electron transfer flavoprotein beta | GK2687 | +++ | 257 | −0.0005 |
| OB2975 | H(+)-transporting ATP synthase beta | GK3358 | +++ | 464 | 0.0026 |
| OB1483 | cell-division initiation protein | GK1135 | +++ | 167 | 0.0008 |
| OB2475 | glycerol kinase | GK1360 | +++ | 500 | 0.0065 |
| OB1415 | pyruvate dehydrogenase E3 | GK1061 | +++ | 468 | 0.0061 |
| OB1090 | 2-oxoglutarate dehydrogenase E2 | GK1024 | +++ | 422 | 0.0259 |
| OB1543 | class I heat shock protein | GK1208 | +++ | 386 | 0.0020 |
| OB2167 | isocitrate dehydrogenase (NADP+) | GK2735 | +++ | 422 | 0.0020 |
| OB2388 | Glycine cleavage system H protein | GK3004 | +++ | 126 | 0.0003 |
| OB1787 | nucleoside-diphosphate kinase | GK2209 | +++ | 148 | 0.0111 |
| OB1886 | acetyl-CoA carboxylase biotin carboxyl carrier subunit | GK2400 | +++ | 159 | 0.0147 |
| OB1168 | ferrochelatase | GK0662 | +++ | 312 | 0.0109 |
| OB2590 | DNA topoisomerase III | GK1688 | +++ | 720 | −0.0019 |
| OB1551 | transcriptional pleiotropic repressor | GK1215 | +++ | 259 | −0.0015 |
| OB3452 | two-component response regulator | GK3474 | +++ | 233 | −0.0014 |
| OB0060 | 50S ribosomal protein L25 | GK0045 | +++ | 215 | 0.0037 |
| OB0110 | 50S ribosomal protein L7/L12 | GK0096 | +++ | 120 | 0.0004 |
| OB0116 | translation elongation factor EF-G | GK0103 | +++ | 692 | 0.0024 |
| OB0117 | elongation factor EF-Tu | GK0104 | +++ | 395 | 0.0064 |
| OB1587 | elongation factor EF-Ts | GK1250 | +++ | 294 | 0.0280 |
| OB1410 | formylmethionine deformylase | GK1057 | +++ | 183 | −0.0011 |
| OB1508 | hypothetical protein | GK1175 | +++ | 254 | 0.0078 |

TABLE 6-continued

List of thermostable proteins from *Oceanobacillus iheyensis* confirmed experimentally and its comparison with computational prediction of the thermostability

| Gene name of OB | Product name | Corresponding gene name of GK | Result of Prediction | Number of amino aids of the product | Difference in scores of principal component analysis between gk and oi |
|---|---|---|---|---|---|
| OB0655 | class I heat shock protein | GK0248 | +++ | 93 | −0.0036 |
| OB2078 | trigger factor | GK2653 | +++ | 428 | 0.0054 |
| OB1932 | manganese superoxide dismutase | GK2457 | +++ | 203 | 0.0040 |
| OB1444 | hypothetical protein | GK1089 | +++ | 121 | −0.0010 |
| OB3023 | hypothetical protein | GK3416 | +++ | 249 | 0.0376 |

Difference in scores of principal component analysis between gk and ob
−: <−0.015 to be judjed as lack of thermostability
+: >−0.015 to be judged to have thermostability
++: >−0.010 to be judged to have thermostability
+++: >−0.005 to be judged to have thermostability

TABLE 7

List of thermostable proteins from *Bacillus cereus* confirmed experimentally and its comparison with computational prediction of the thermostability

| Gene name of BC | Product name | Corresponding gene name of GK | Result of Prediction | Number of amino aids of the product | Difference in scores of principal component analysis between gk and bc |
|---|---|---|---|---|---|
| BC0152 | Adenylate kinase | GK0127 | − | 215 | −0.0200 |
| BC0294 | 10 kDa chaperonin GroES | GK0248 | − | 95 | −0.0213 |
| BC1510 | DNA-binding protein HU | GK2215 | − | 113 | −0.0231 |
| BC4471 | Porphobilinogen deaminase | GK2645 | − | 308 | −0.0213 |
| BC2488 | Propionyl-CoA carboxylase beta chain | GK1603 | + | 512 | −0.0116 |
| BC4163 | Phosphate butyryltransferase | GK2382 | + | 298 | −0.0123 |
| BC0013 | Inosine-5'-monophosphate dehydrogenase | GK0009 | ++ | 486 | −0.0068 |
| BC1021 | CMP-binding factor | GK0646 | ++ | 313 | −0.0094 |
| BC4523 | Electron transfer flavoprotein beta-subunit | GK2687 | ++ | 256 | −0.0093 |
| BC4571 | Deblocking aminopeptidase | GK2713 | ++ | 362 | −0.0062 |
| BC0102 | Negative regulator of genetic competence | GK0078 | +++ | 810 | −0.0034 |
| BC0108 | Glutamyl-tRNA synthetase | GK0083 | +++ | 495 | 0.0051 |
| BC0110 | Cysteinyl-tRNA synthetase | GK0085 | +++ | 464 | 0.0055 |
| BC0295 | 60 kDa chaperonin GROEL | GK0249 | +++ | 543 | −0.0012 |
| BC0377 | Alkyl hydroperoxide reductase C22 | GK2575 | +++ | 186 | −0.0027 |
| BC0380 | L-fuculose phosphate aldolase | GK1906 | +++ | 212 | 0.0211 |
| BC0778 | Thioredoxin | GK0567 | +++ | 149 | 0.0215 |
| BC1127 | Malate synthase | GK1533 | +++ | 519 | 0.0214 |
| BC1168 | ClpB protein | GK0799 | +++ | 865 | 0.0068 |
| BC1338 | Oligoendopeptidase F | GK0963 | +++ | 563 | 0.0062 |
| BC1406 | Histidinol dehydrogenase | GK3075 | +++ | 428 | 0.0034 |
| BC1511 | GTP_cyclohydrol, GTP cyclohydrolase I | GK2214 | +++ | 188 | 0.0003 |
| BC2011 | Non-specific DNA-binding protein Dps/ Iron-binding ferritin-like antioxidant protein/Ferroxidase | GK2861 | +++ | 146 | 0.0084 |
| BC2778 | Acetoin dehydrogenase E1 component | GK0711 | +++ | 343 | −0.0032 |
| BC2833 | Dihydrodipicolinate synthase | GK1961 | +++ | 297 | 0.0414 |
| BC3652 | Histidine ammonia-lyase | GK0385 | +++ | 505 | 0.0112 |
| BC3824 | Protein Translation Elongation Factor Ts | GK1250 | +++ | 294 | 0.0094 |
| BC4162 | Leucine dehydrogenase | GK2381 | +++ | 365 | 0.0043 |
| BC4198 | Xaa-Pro dipeptidase | GK2411 | +++ | 352 | −0.0028 |
| BC4312 | Chaperone protein dnaK | GK2504 | +++ | 610 | 0.0057 |
| BC4600 | 6-phosphofructokinase | GK2740 | +++ | 318 | −0.0017 |
| BC4661 | Acetoin utilization acuB protein | GK2808 | +++ | 213 | 0.0080 |
| BC4702 | Xaa-His dipeptidase | GK2831 | +++ | 467 | 0.0005 |
| BC4902 | Transcriptional regulator, AsnC family | GK2929 | +++ | 164 | 0.0042 |
| BC5190 | Probable Sigma (54) modulation protein | GK3109 | +++ | 179 | 0.0090 |
| BC5280 | (3R)-hydroxymyristoyl-[acyl carrier protein] dehydratase | GK3329 | +++ | 143 | 0.0309 |
| BC5343 | 3-hydroxybutyryl-CoA dehydrogenase | GK3395 | +++ | 272 | 0.0041 |
| BC5474 | S30P Probable Sigma (54) modulation protein/SSU ribosomal protein | GK3480 | +++ | 76 | 0.0117 |

Difference in scores of principal component analysis between gk and bc
−: <−0.015 to be judged as lack of thermostability
+: >−0.015 to be judged to have thermostability
++: >−0.010 to be judged to have thermostability
+++: >− to be judged to have thermostabitity Tables 4 to 7 show the details of proteins confirmed to have thermostability by the heat treatment study, which were derived from *B. subtilis* (BS) (Table 4), *B. halodurans* (BH) (Table 5), *O. iheyensis* (OI) (Table 6), and *B. cereus* (BC) (Table 7), respectively. The columns of the respective tables indicate, from the left, "gene name of BS, BH, OI or BC", "product name thereof", "corresponding gene name of GK", "result of prediction", "number of amino acids of the product", and "difference in scores of principal component analysis between GK and BS, BH, OI or BC", respectively. In the column of "result of prediction", "−" indicates the case where the difference in PC2 values between each microorganism and GK is lower than −0.015, thereby being judged lack of thermostability, and "+", "++", "+++" indicate the cases where the difference is greater than −0.015, −0.01 and −0.005, respectively, thereby being judged presence of thermostability.

As shown in Tables 4 to 7, at least 38 thermostable proteins for BC and BH, 117 thermostable proteins for BS and 52 thermostable proteins for OI were identified. Then, how the presence of or lack of thermostability of the proteins, which were confirmed to have thermostability had been predicted by comparison of the principal component scores between GK and other *Bacillus*-related species was investigated. As described above, when the difference in the principal component scores between the respective *Bacillus*-related species and GK≧−0.015 is defined to have thermostability, it is found that 34 out of 38 proteins (89.5%) for BC shown in Table 7, 36 out of 38 proteins (94.7%) for BH shown in Table 5, 103 out of 117 proteins (88.0%) for BS shown in Table 4, and 46 out of 52 proteins (88.5%) for OI shown in Table 6 were predicted to have thermostability by the method of the invention.

These results are summarized and shown in the following Table 8. The respective signals in Table 8 are the same as in Table 2. Accordingly, the method of the invention capable of judging the thermostability of a protein produced by a mesophilic bacterium by calculating the correlation with a corresponding protein of a thermophilic bacterium indicates the thermostability of the protein.

thermostable organism which has a relationship with an organism producing a test protein is preferred. As the "relationship" referred to here, similarity in a biological classification, genetic similarity in embryology, functional similarity retained by the test protein and the like can be exemplified.

A "protein retained by a thermostable organism" in the invention is a protein produced by a thermostable organism, and may be any protein as long as it is produced by a thermostable organism whether or not it is essential to life.

In addition, a "protein which is retained by a thermostable organism and corresponds to a test protein" in the invention may be a protein with the same type of function as that of a test protein, preferably with the function equal to that of a test protein. It is not necessary to have a biological or embryological relationship, however, a protein with a biological or embryological relationship may be preferably exemplified. For example, as described above, a correlation based on a biological orthologous gene, a correlation of proteins with the same type of function among organisms of the same genus or the same species, etc. are exemplified.

The "protein which is retained by a thermostable organism and corresponds to a test protein" in the method of the invention is not always one protein, and may be 2 or more proteins. In the case where 2 or more proteins can be selected as such a protein, it is possible to compare these one another, and to perform judgment comprehensively.

As the method of calculating a "thermostability index of a test protein based on the amino acid composition" in the method of the invention, a method based on a principal component analysis comprising the steps of extracting a protein based on a gene encoding a protein, which is identified in the genome of an organism as described above as an example, excluding a protein whose amino acid sequence length is less than 50 amino acids from these proteins, further excluding a protein which has been predicted to contain 2 or more transmembrane domains by the PSORT program, calculating an average amino acid composition on a species basis by using the amino acid sequences of the remaining proteins, and with regard to the calculated average amino acid composition,

TABLE 8

| prediction | BC (number) | BC (%) | BH (number) | BH (%) | BS (number) | BS (%) | OI (number) | OI (%) |
|---|---|---|---|---|---|---|---|---|
| − | 4 | 10.5 | 2 | 5.3 | 14 | 12.0 | 6 | 11.5 |
| + | 2 | 5.3 | 4 | 10.5 | 20 | 17.1 | 7 | 13.5 |
| ++ | 4 | 10.5 | 7 | 18.4 | 14 | 12.0 | 9 | 17.3 |
| +++ | 28 | 73.7 | 25 | 65.8 | 69 | 59.0 | 30 | 57.7 |
| ++, +++ | 32 | 84.2 | 32 | 84.2 | 83 | 70.9 | 39 | 75.0 |
| +, ++, +++ | 34 | 89.5 | 36 | 94.7 | 103 | 88.0 | 46 | 88.5 |
| total | 38 | | 38 | | 117 | | 52 | |

The method of the invention was explained based on the *Bacillus*-related species. However, it is easily understood by those skilled in the art that the method of the invention is not limited to the *Bacillus*-related species, and can be applied to any species as long as a thermostable protein corresponding to a test protein exists.

A "thermostable organism" in the invention may be an organism that can maintain its life at a temperature where human can maintain his/her life or higher, however, the term is referred to as an organism that can maintain its life at specifically about 50° C. or higher, preferably 60° C. or higher, more preferably 65° C. or higher. Examples include thermophilic bacteria, spring organisms and the like. As the "thermostable organism" in the method of the invention, a using the princomp function in the R statistical analysis package by using a matrix, as input, in which each row and column corresponds to the species and an amino acid, respectively (Kreil D. P. and Ouzounis, C. A. (2001), Identification of thermophilic species by the amino acid compositions deduced from their genome. Nucleic Acids Res. 29, 1608-1615) is effective. However, the method is not limited thereto, and if there are predetermined number or more of proteins whose thermostability has been verified experimentally, it is possible to improve the method by incorporating a technique such as a discrimination analysis or a regression analysis. In addition, it is preferred to use an entire protein (whole length) in the invention, however, it is possible to use each domain or a partial length of a protein as a target.

As the "comparison of analytical values" in the method of the invention, a method of obtaining a difference between the analytical values as described above is convenient and preferred, however, it is not limited thereto. In the case where a large amount of data is accumulated, it is possible to perform comparison based on a difference with the average value of all elements or a value processed statistically such as deviation.

In addition, a judgment criterion in the comparison can be set within a range where it can be confirmed that a test protein has thermostability practically. In the foregoing example, it can be judged that a protein has thermostability when a difference in principal component scores calculated by the value of an eigenvector (weighting factor of each amino acid) and the number of amino acids of each protein is in a range of about 0.005 to 0.015 or lower. Such judgment is not only represented by the presence of or lack of thermostability, but can be represented by a ratio (%) of the possibility of having thermostability.

As the data for calculating a specific analytical value by a principal component analysis based on the amino acid composition of a test protein in the method of the invention, data of the amino acid sequence or the nucleotide sequence of the protein and the like are exemplified, however, it is not limited thereto and may only be its amino acid composition. As such data, in order to increase judgment accuracy, data with a large amount of information is preferred, however, the nucleotide sequence encoding the protein as described above as an example can be cited as a convenient and preferred example. Other than this, three-dimensional data of a protein can be further added, however, what data is required depends on not only improvement of judgment accuracy but also an approach for processing the data.

Specifically, the method of the invention comprises the following steps (1) to (6):

(1) a step of obtaining the amino acid sequence of a protein and/or the nucleotide sequence encoding the protein, (2) a step of calculating the "specific analytical value" of the protein based on the data of the amino acid sequence and/or the nucleotide sequence, (3) a step of selecting a "protein which is retained by a thermostable organism and corresponds to a test protein" by using the protein as the test protein, (4) a step of obtaining data of the analytical value of the selected "corresponding protein", (5) a step of comparing both analytical values, and (6) a step of performing judgment based on the results of comparison.

With regard to these steps, except for the determination of the sequence in the step (1) and the selection in the step (3), their processing methods can be specified in advance, and processing in a computer is possible. In addition, with regard to the step (3), if classification has been performed in advance based on an enzyme classification, a "corresponding protein" which is a subject to be selected can be selected from accumulated data. Accordingly, all the steps except for the step (1) can be processed in a computer.

In other words, in the invention, the method of the invention described above is programmed so as to be processed in a computer, and the invention provides a processing method in a computer comprising (a) a method of calculating a specific analytical value by processing in a computer by inputting data of the amino acid sequence or the nucleotide sequence of the protein into the program, (b) a method of extracting a "corresponding protein" to the protein from accumulated data based on the classification signal, function data, origin data or the like, (c) a method of referring to the specific analytical value of the "corresponding protein" extracted in the step (b) as a value of calculated or accumulated data, (d) a method of comparing the specific analytical value of the protein and the specific analytical value of the "corresponding protein", and (e) a method of displaying (outputting) the result of comparison.

In the processing in a computer, the analytical value of a protein which is retained by a thermostable organism and corresponds to a test protein can be calculated in each case, however, it is also possible that a value calculated by a principal component analysis based on the amino acid composition of the protein is classified according to the type of each protein and listed to create accumulated data. Such accumulated data can be stored in a computer readable recording medium so as to utilize it as the information for processing in a computer. Examples of such a recording medium include a hard disk, DVD disc, CD-ROM, MO, floppy disc and the like.

As the program of the invention for judging whether or not a test protein has thermostability by allowing a computer to execute each of the following steps, for example a program for judging whether or not a test protein has thermostability by comparing a specific analytical value based on the amino acid composition of a test protein and a specific analytical value of a known corresponding protein by the steps of:

(1) inputting the amino acid sequence of the test protein, (2) searching a known protein related to a corresponding protein produced by another species different from the one producing the test protein (corresponding protein), (3) calculating a specific analytical value by a principal component analysis based on the amino acid composition of the test protein, (4) calculating the specific analytical value of the corresponding protein searched in the step (2) and the specific analytical value of the test protein calculated in the step (3), and calculating the difference between both values, (5) judging whether or not the test protein is similar to the corresponding protein searched in the step (2) based on the difference calculated in the step (4), and (6) displaying the corresponding protein searched in the step (2) and the result of judgment in the step (5)

is exemplified.

Hereunder, the program of the invention will be explained. In the following, explanation will be made by using a protein which is in an orthologous relationship as an example of the corresponding protein, and a second principal component score of the principal component analysis as an example of the specific analytical value based on the amino acid composition. In addition, the program of the invention can be executed as a stand-alone program, however, in the following, explanation will be made by using a server-type program as an example. The following explanation is only an example of the invention, and the invention is not limited to these examples.

Figure 8:
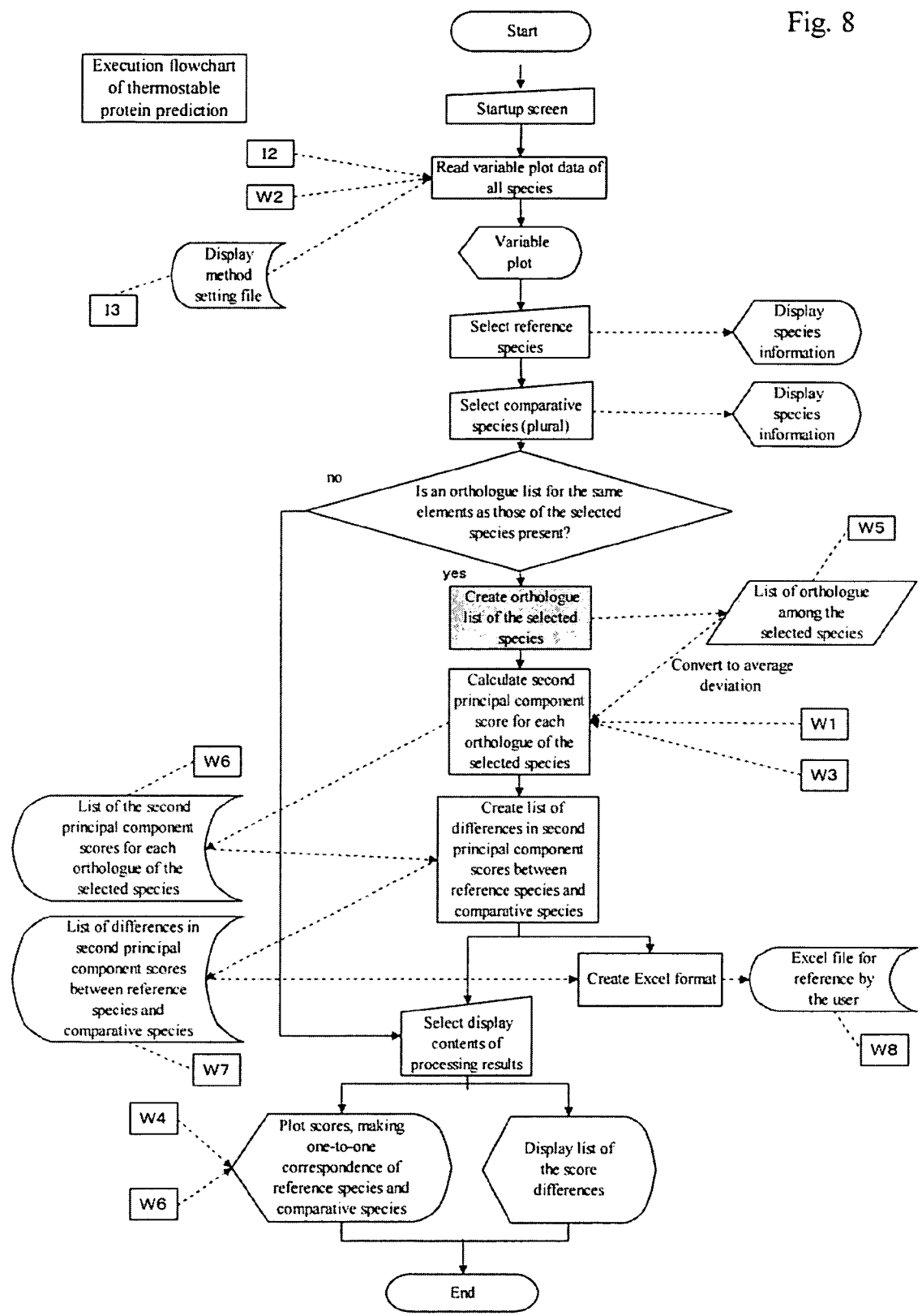
FIG. 8 is a flowchart showing processing from the user viewpoint in the program of the invention.

FIG. 8 shows an execution flowchart of the client. When it starts up, the startup screen is displayed, and data necessary for an orthologue search is read. After startup setting is completed, the screen for input from a terminal is displayed. The input of a test protein may be performed by any method such as type in, FD, CD and online, and the amino acid sequence and/or the nucleotide sequence of a test protein and its origin are input. In FIG. 8, they are indicated as a "variable plot".

After completing the input, an orthologue search is executed, however, it is optionally designed that an organism to be searched can be selected. The selection of a species is not essential, and all the accumulated species can be also used as a target. An orthologue search is executed for a designated species.

As a method of an orthologue search, a variety of parameters such as the amino acid sequence, amino acid composition, function, origin and expressed organ of a test protein can be adopted, however, in this example, an orthologue search is executed by a homology search based on the amino acid sequence. A protein, which has a high homology to a test protein, for example, with a homology of 70% or higher, 80% or higher, or 85% or higher and is derived from a species different from that of the test protein, is selected as an orthologue candidate in this example.

In the case where a protein to become a corresponding orthologue could not be retrieved from the orthologue search result, comparison cannot be performed (in FIG. 8, "Is an orthologue list present?"→"no"), therefore the processing is finished.

In the case where one or more orthologues were retrieved (in FIG. 8, "Is an orthologue list present?"→"yes"), an orthologue list is created and a second principal component score based on the amino acid composition for each orthologue is calculated. Then, The second principal component score of the test protein and the second principal component score of the corresponding protein are compared to obtain the difference, and judgment is performed.

With regard to the judgment at this time, in this example, three stages, ±0.005, ±0.010, ±0.015 of the difference in both scores are set as default, however, a user can set it optionally. This result is displayed in an excel format or a screen display format.

This result is basically displayed in a table format, however, it can be displayed in a graph designated by a user based on this table format. In addition, depending on the degree of difference, it may be colored. In this case, as the color, red, blue, green or the like may be used to indicate default values.

Figure 9:
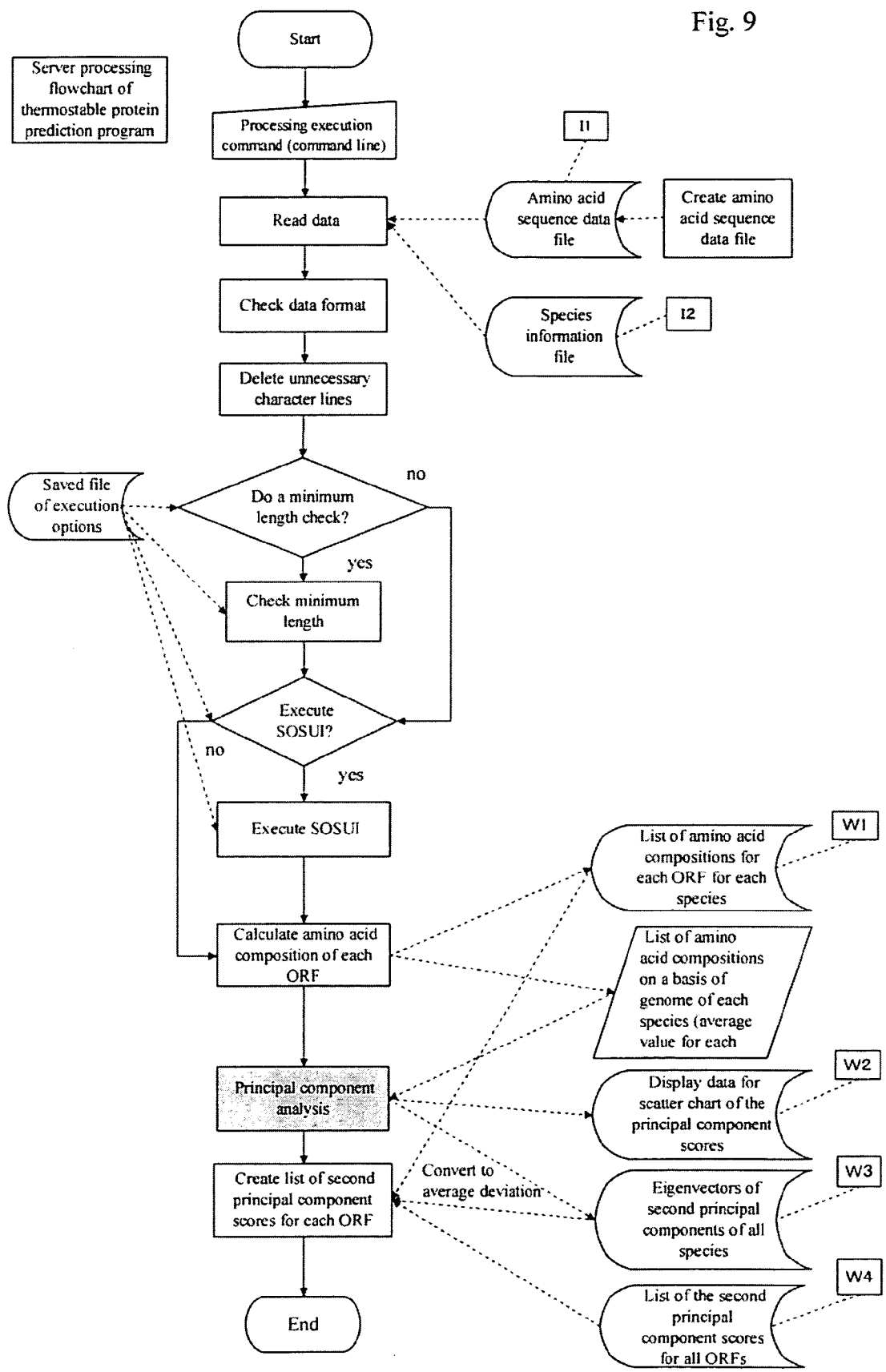
FIG. 9 is a flowchart showing input processing from the server viewpoint in the program of the invention.

FIG. 9 shows a flowchart from the server until data input. A startup request is issued by a client, a program is started, and data is read. After completing data format check, a character string other than that of an amino acid is deleted, and recognition of the amino acid is performed. Based on the input amino acid sequence, the number of amino acids is counted. In the case where the number of amino acids is less than 50, the processing is finished (In FIG. 9, "Minimum length check"). Subsequently, whether or not the input protein has a transmembrane domain is detected by the "SOSUI" program. This program is a program for deducing a transmembrane domain from the sequence of a hydrophobic amino acid. In the case where the input protein was judged to have 2 or more transmembrane domains by the "SOSUI" program, the protein is considered to be a membrane protein and excluded from the subjects of processing of this program, and the processing is finished.

In the case where the number of the amino acids of the input protein is 50 or more and the site deduced to be a transmembrane domain is one or less, an analysis of the amino acid composition is carried out. With regard to the analysis of the amino acid composition, for each of the 20 types of amino acids in the open reading frame (ORF), the ratio of content of each amino acid is calculated at a percentage. Subsequently, a principal component analysis is carried out. In this principal component analysis, a commercially available program for statistical processing can be used. A second principal component score is calculated by a principal component analysis, and data input processing is completed.

With regard to a corresponding protein search, a homology search is executed from the N-terminal side and the C-terminal side of a protein by using, for example, BLASTP, and a protein with the highest homology is defined as a corresponding protein. The case where only a protein with a homology of 70% or lower as default is searched is defined as no corresponding protein, however, the lower limit of homology can be set by a user.

The program of the invention refers to a database of known proteins for a corresponding protein search. In order to this, it is necessary to accumulate data of known proteins, therefore, the program of the invention can also include a step of inputting data of a known protein for a corresponding protein search. As a data source of such data, a paper published in an academic journal, a database available on the Internet and the like are exemplified. In the case of a database available on the Internet, it is possible to program a computer to automatically access the Internet on a regular or irregular basis and to automatically download new information. Data obtained in this way can be stored in a reference file of the program of the invention as accumulated data through the same flow as shown in FIG. 9.

In addition, the program of the invention refers to a database of the second principal component scores of a principal component analysis based on the amino acid composition of a known protein. The second principal component score can be calculated based on the amino acid sequence in the database of known proteins for a corresponding protein search. Therefore, when a known protein is input for the foregoing corresponding protein search, the score can be calculated and input as accumulated data.

The program of the invention can further include such an input step.

The main functions of the program of the invention are summarized and shown below.

The amino acid sequences of a microorganism with thermostability and of several species of closely related microorganisms without thermostability are used as input, and the results of a principal component analysis based on the amino acid compositions are displayed as a scatter chart. From the scatter chart of the principal component scores on a microorganism basis, a microorganism with thermostability can be deduced, further, an exceptional microorganism candidate whose deduction results from the actual growth temperature and the principal component analysis disagree with each other can be obtained.

By the function of comparing the second principal components of proteins in an orthologous relationship between a thermophilic bacterium and a mesophilic bacterium, a thermostable protein in a mesophilic bacterium can be deduced. In addition, in the case of an exceptional microorganism whose deduction results from the actual growth temperature and the principal component analysis disagree with each other, deduction of a gene closely related to thermostability can be performed.

Further, the program of the invention comprises two steps: one is a calculation step for creating a data set necessary for prediction of thermostability, and the other is a step of predicting thermostability based on the amino acid composition of a protein, for which the presence of or lack of thermostability is desired to be known, and the contents and the order of processing are as follows.

(1) Data Set Creation Step (a) Minimum sequence exclusion: Exclude an amino acid sequence shorter than a predetermined length.

(b) Hydrophobic domain exclusion: Exclude a sequence containing 2 or more transmembrane domain based on the data hit by SOSUI (transmembrane domain prediction program).

(c) Determination of an orthologue among the respective species:

Execute BLASTP against all the entries, and acquire the one with the best score from the results one by one.

Create FASTA file in which only the result of orthologue was left (W1).

(d) Calculation of Amino Acid Composition:

Calculate an amino acid composition on an orthologue basis, and calculate the average on a species basis.

Execute calculation based on W1 File. Store the amino acid compositions on an orthologue basis as W2 file.

(e) Principal component analysis: Calculate a principal component score based on the amino acid composition.

Based on the principal component score on a species basis, output the display data for a scatter chart of the principal component scores into W3 file.

By using the eigenvector of the second principal component and W2 file, calculate the score for each orthologue and store it in W4 file.

(2) Thermostability Prediction Step (a) Display of the whole distribution chart:

Read I2, I3 and W3 files, and create and display a scatter chart on a species basis (each parameter can be selected).

From the whole distribution chart, a reference organism (an organism having a corresponding protein) and a comparable species (the plural organisms is also applicable) can be selected.

(b) Compare the scores of proteins in an orthologous relationship among all the proteins of an organism having a corresponding protein and an organism having a test protein.

(c) With regard to the selected species, read W1 and W4 files and obtain the information.

(d) Display a list of the differences in the scores of the proteins in an orthologous relationship among all the proteins retained in an organism having a corresponding protein and the respective comparative species (depending on the difference degree, the differences are distinguished by using three different colors).

(e) In addition, display the differences in the scores of orthologues showing one-to-one correspondence of an organism having a corresponding protein and a comparative organism as a scatter chart.

The main functions of the program of the invention are summarized and shown in the following Table 9.

TABLE 9

| | Name of function | Contents |
|---|---|---|
| 1 | Input data creation support function | Function of automatically downloading a default format and further supporting creation of an input file of a system. |
| 2 | Parameter control function | Function of setting and storing a processing method of executing project data creation processing and orthologue search processing |
| 3 | Input data check function | Function of executing, with regard to the input data, (1) format check, (2) deletion of unnecessary character string, (3) length check, and (4) exclusion of hydrophobic amino acid sequence. |
| 4 | Principal component analysis function | Function of calculating the amino acid composition of each microorganism, and executing a principal component analysis based on the results. |
| 5 | Display function of scatter chart of principal component analysis results | Function of displaying the principal component analysis results as a scatter chart, and further outputting the image of the scatter chart as an image file in an editable layer. |
| 6 | Orthologue search function | Function of detecting an orthologue among microorganisms selected by a user by executing simplex or duplex BLAST. |
| 7 | Orthologue list creation function | Function of displaying an orthologue list and the second principal component score for each orthologue and the score after comparison. Direct printing from the screen or output in an Excel format can be performed. |
| 8 | Display function of orthologue scatter chart | Function of displaying the second principal component scores for each orthologue between 2 organisms as a scatter chart, and further outputting the image of the scatter chart as an image file in an editable layer. |
| 9 | Input function of sequence of comparison | Function of executing processing corresponding to input data check function and orthologue search function with regard to the plural amino acid sequences input in Multi FastA format from the screen, and further calculating the second principal component scores and displaying the list and the scatter chart. |

The program of the invention can be stored on a computer readable recording medium in order to allowing a computer to execute the program. Examples of such a recording medium include a hard disk, DVD disc, CD-ROM, MO, floppy disc and the like.

Therefore, the invention also provides a computer readable recording medium having stored thereon the program of the invention.

In the recording medium of the invention, a database of known proteins and a database of specific analytical values based on the amino acid compositions of known proteins for a corresponding protein search, which the program of the invention refers to, can be recorded.

The method of the invention enables prediction of the thermostability of a protein by calculating a specific analytical value of the protein without conducting an experiment, or more conveniently, on a personal computer, therefore, it is very rapid and inexpensive. In addition, the invention enables the judgment not on a basis of an organism, but on a basis of a protein produced by the organism. Therefore, the search scope of a thermostable enzyme whose source was conventionally limited to a thermophilic bacterium can be extended to the scope of a protein produced by a mesophilic bacterium, whereby the range of screening for thermostable proteins can be expanded. Further, with regard to the screening of a thermostable enzyme from a mesophilic bacterium which had taken enormous time and effort before, since candidates of thermostable enzymes can be narrowed down in advance, whereby it becomes possible to easily perform search or screening of a thermostable enzyme, which can be applied to various processes.

Further, by using the computer program developed by the invention, a thermostable protein derived from a mesophilic bacterium closely related to a thermophilic bacterium is conveniently predicted, whereby it is possible to shorten the time required for a search of a wider variety of thermostable enzymes than ever to a large extent. In addition, the program of the invention enables prediction of the thermostability of a protein for which the presence of or lack of thermostability is desired to be known on a personal computer working with Windows™, therefore, it can be easily used by, in particular, even a person who has no knowledge of computer language.

Hereunder, the invention will be explained more specifically with reference to the Examples, however, the invention is by no means limited to these Examples.

EXAMPLES

Example 1

Calculation Method of Data of 120 Species of Bacteria

From the database at NCBI, the genome data of 119 species of microorganisms was obtained, and the sequences of proteins identified in the 120 types of genomes including the obtained 119 types of genomes and the genome of *G. kaustophilus* HTA426, which had been determined in the invention were used for an analysis. From these sequences of proteins, a protein with a sequence length of less than 50 amino acids was excluded, further a protein which had been predicted to contain 2 or more transmembrane domains by the PSORT program (K. Nakai, P. Horton, Trends Biochem. Sci., 24, 34-6, 1999) was also excluded. By using the sequences of the remaining proteins, an average amino acid composition was calculated on a species basis, a matrix in which each row and column corresponds to a species and an amino acid, respectively was input, and a principal component analysis was performed in accordance with the method of Kreil et al. (D. Kreil, C. Ouzounis, Nucleic Acids Res, 29, 1608-15, 2001). In the analysis, the princomp function in the R statistical analysis package was used.

Example 2

Calculation Method of Data of Specific Analytical Values of 965 Proteins

Orthologous grouping of 5 species of microorganisms, GK, BC, BH, BS and OI was performed using the clustering program on MBGD (I. Uchiyama, Nucleic Acids Res, 31, 58-62, 2003) server by Uchiyama. Only an orthologous group present in all the 5 species and showing one-to-one correspondence was used for the analysis. Further, a group containing 4 or more proteins which had been predicted to contain 2 or more transmembrane domains by PSORT was excluded. By using the eigenvector of the second principal component obtained in the principal component analysis described in Example 1, the thermostability index of each protein was calculated as an inner-product of the amino acid composition vector with the eigenvector.

Example 3

Analysis of All the Proteins

A liquid culture was performed aerobically for 18 hours by using LB medium (pH 7) for GK, BS and BC, and Horikoshi II medium (pH 9.5) (Takami, H, Kobayashi, T., Aono, R., and Horikoshi, K. Appl. Microbiol. Biotechnol. 38, 101-108, 1992) for BH and OI. The culture was performed at 55° C. for GK and at 37° C. for the other microorganisms. The cultured cells were harvested by centrifugation, washed with 50 mM phosphate buffer, and resuspended in the same buffer, whereby a cell suspension was obtained. Then, the cell suspension was subjected to a French press, and the obtained homogenized cell suspension was centrifuged to remove the cell debris. The obtained supernatant was used as a protein solution for the analysis of all the proteins. In addition, this protein solution was treated with heat at 60° C. or 70° C. for 10 minutes, then rapidly cooled down to obtain a heat-treated protein solution. The analysis of all the proteins was carried out by native gel electrophoresis. The gel concentration was 12.5%. After the electrophoresis, the gel was stained with Coomassie Brilliant Blue.

Example 4

Identification of Thermostable Protein

By using the protein solutions of the respective organisms prepared by the method described in Example 3, the proteins were separated by native gel electrophoresis, stained with Coomassie Brilliant Blue in the same manner as in Example 3. From the lanes 3 of 4 species except for GK in FIG. 6, which were obtained by subjecting the protein solutions treated with heat at 70° C. for 10 minutes to electrophoresis, the bands of proteins that were not lost after the heat treatment were cut out from the gel with a length of 3 mm each. Then, in accordance with the usual methods, the proteins in the gel were treated with trypsin, and the peptides were fractionated by an LC/MS/MS system, whereby the mass was calculated. The mass analysis was carried out by using Bioworks 3.1, Xcalibour system manufactured by Thermo Electron Co., and comparing the results and the database of the proteins of each *Bacillus*-related species. In this way, identification of the proteins contained in each band was carried out.

The results are shown in Tables 4 to 7.

Example 5

Analysis of Esterase

By using the protein solutions of the respective organisms prepared by the method described in Example 3, the proteins were separated by native gel electrophoresis in the same manner. Then, detection of only the band having an esterase activity was carried out by the method shown below.

Two milliliter of 1% α-naphtyl acetate dissolved in 50% acetone and 100 mg of fast blue BB salt were added to 100 ml of 0.05 M Tris-HCl buffer (pH 7.4), mixed well, and the solution was transferred to a plastic container. Then, the gel after the electrophoresis was immersed in the solution and incubated at 37° C. for 10 minutes in the dark. When the band having an esterase activity appeared, the solution was removed, and the gel was washed with distilled water.

By using the obtained esterase from each organism, a protein solution without heat treatment, protein solutions with heat treatment at 60° C. and 70° C. for 10 minutes, which had been rapidly cooled down after the heat treatment, were prepared, and native gel electrophoresis was carried out. The gel concentration was 12.5%.

Example 6

Analysis of Flagellin

By using a primer set designed from the nucleotide sequences of hag genes of the 5 strains, the hag genes were amplified by PCR. Then, these PCR products were ligated to a plasmid vector for TA cloning with His-tag at the N-terminal end (pCRT7 TOPOTA), and transformation of *E. coli* (*E. coli* BL21 DE3) was carried out. The transformed *E. coli* was cultured until OD 600 reached 0.6. Then, 0.5 mM IPTG was added and the protein was expressed at 30° C. for 3 to 5 hours. The cells were homogenized with a French press in the same manner as above, and the obtained homogenized cell suspension was applied to a Talon metal affinity column for conveniently purifying only a protein with His-tag, and the protein was allowed to adhere to the column. Then, the target protein was purified with 150 mM imidazole, 50 mM sodium phosphate and 300 mM NaCl. The purified protein was subjected to SDS-PAGE electrophoresis and the degree of purification was confirmed.

By using the purified protein, heat treatment was carried out in accordance with the method described in Example 4. Then, the proteins were separated by native gel electrophoresis, and stained with Coomassie Brilliant Blue.

Example 7

Analysis of GroES

By using a primer set designed from the nucleotide sequences of groES genes of the 5 strains, the groES genes were amplified by PCR. Then, the proteins were produced and purified in the same manner as in Example 6. In addition, by using the purified protein, heat treatment and electrophoresis were carried out in the same manner, whereby analysis of GroES protein was carried out.

A thermostable protein such as a thermostable enzyme is utilized in various industrial fields such as sugar industry, protein industry and fertilizer industry, and its importance is extremely high. In addition, as a DNA polymerase or the like, it is considered to be indispensable to use a thermostable enzyme in genetic engineering techniques.

The method of the invention provides a novel method of searching a thermostable protein such as a thermostable enzyme by a convenient approach, and is an extremely useful method in industry. In addition, the method of the invention indicates that the search scope of thermostable proteins can be further expanded from the conventional proteins derived from thermophilic bacteria, and makes an extremely significant contribution in industry.

What is claimed is:

1. A method of determining whether or not a test protein has thermostability, comprising the steps of:
    identifying (i) a thermostability index of the test protein based upon an amino acid sequence of the test protein and (ii) a thermostability index of a corresponding protein produced by a thermophilic microorganism selected from a plurality of thermophilic microorganisms, the corresponding protein being in an orthologous relationship with the test protein, wherein the proteins have amino acid sequences greater than 50 amino acids and are not predicted to contain two or more transmembrane domains;
    comparing the thermostability indices of the test protein and the corresponding protein;
    determining that the test protein has thermostability when the difference between the thermostability index of the test protein and the thermostability index of the corresponding protein falls within a predetermined range; and
    outputting the result of said determining step, wherein all steps are performed on a suitably programmed computer.

2. The method of claim 1, wherein the identifying step further comprises:
    obtaining amino acid sequences of all proteins of said plurality of thermophilic microorganisms from complete known genome sequences of said plurality of thermophilic microorganisms;
    obtaining amino acid sequences of all proteins of a plurality of non-thermophilic microorganisms from complete genome sequences of non-thermophilic microorganisms;
    obtaining amino acid compositions which said plurality of thermophilic microorganisms have based on the amino acid sequences of all proteins which said plurality of thermophilic microorganisms have;
    obtaining amino acid compositions which said plurality of non-thermophilic microorganisms have based on the amino acid sequences of all proteins which said plurality of non-thermophilic microorganisms have;
    obtaining a weighting factor of amino acid by performing a principle component analysis on the amino acid compositions of said plurality of thermophilic and non-thermophilic microorganisms;
    selecting proteins having an orthologous relationship in all of the thermophilic and non-thermophilic microorganisms;
    selecting, as the test protein, a protein which one of said plurality of non-thermophilic microorganisms has, from the selected proteins;
    selecting, as the corresponding protein, a protein which one of said plurality of thermophilic microorganisms has, from proteins with which the test protein is in the orthologous relationship;
    obtaining the thermostability index of the test protein based on the weighting factor and the amino acid composition of the test protein; and
    obtaining the thermostability index of the corresponding protein based on the weighting factor and the amino acid composition of the corresponding protein.

3. The method of claim 2, wherein the step of obtaining said amino acid compositions which said plurality of thermophilic microorganisms have is conducted after excluding proteins whose amino acid sequence is 50 amino acids or less and after excluding proteins which are predicted to contain two or more transmembrane domains, and
    wherein the step of obtaining said amino acid compositions which said plurality of non-thermophilic microorganisms have is conducted after excluding proteins whose amino acid sequence is 50 amino acids or less and after excluding proteins which are predicted to contain two or more transmembrane domains.

4. The method of claim 2, wherein the step of obtaining said amino acid compositions which said plurality of thermophilic microorganisms have is conducted after excluding proteins whose amino acid sequence is 50 amino acids or less and after excluding proteins which are predicted to contain two or more transmembrane domains.

5. The method of claim 2, wherein the predetermined range is −0.01 to +0.01.

6. The method of claim 2, wherein the test protein is an enzyme.

7. The method of claim 2, wherein the thermophilic microorganisms are selected from the group consisting of *Bacillus, Marinococcus, Halobacillus, Virgibacillus, Salibacillus, Amphibacillus, Gracilibacillus, Oceanobacillus, Saccharoccus, Geobacillus, Thermoactinomyces, Brevibacillus, Aneurinibacillus, Paenibacillus,* and *Alicyclobacillus*.

8. A computer program product stored in a computer readable storage medium, for determining whether or not a test protein has thermostability, that permits a computer to implement the following steps of:
   identifying (i) a thermostability index of the test protein based upon an amino acid sequence of the test protein and (ii) a thermostability index of a corresponding protein produced by a thermophilic microorganism selected from a plurality of thermophilic microorganisms, the corresponding protein being in an orthologous relationship with the test protein, wherein the proteins have amino acid sequences greater than 50 amino acids and are not predicted to contain two or more transmembrane domains;
   comparing the thermostability indices of the test protein and the corresponding protein;
   determining that the test protein has thermostability when the difference between the thermostability index of the test protein and the thermostability of the corresponding protein falls within a predetermined range; and
   outputting a result of said determining step.

9. The computer program product of claim 8, wherein the identifying step further comprises:
   obtaining amino acid sequences of all proteins of said plurality of thermophilic microorganisms from complete known genome sequences of said plurality of thermophilic microorganisms;
   obtaining amino acid sequences of all proteins of a plurality of non-thermophilic microorganisms from complete genome sequences of non-thermophilic microorganisms;
   obtaining amino acid compositions which said plurality of thermophilic microorganisms have based on the amino acid sequences of all proteins which said plurality of thermophilic microorganisms have;
   obtaining amino acid compositions which said plurality of non-thermophilic microorganisms have based on the amino acid sequences of all proteins which said plurality of non-thermophilic microorganisms have;
   obtaining a weighting factor of amino acid by performing a principle component analysis on the amino acid compositions of said plurality of thermophilic and non-thermophilic microorganisms;
   selecting proteins having an orthologous relationship in all of the thermophilic and non-thermophilic microorganisms;
   selecting, as the test protein, a protein which one of said plurality of non-thermophilic microorganisms has, from the selected proteins;
   selecting, as the corresponding protein, a protein which one of said plurality of thermophilic microorganisms has, from proteins with which the test protein is in the orthologous relationship;
   obtaining the thermostability index of the test protein based on the weighting factor and the amino acid composition of the test protein; and
   obtaining the thermostability index of the corresponding protein based on the weighting factor and the amino acid composition of the corresponding protein.

10. The computer program product of claim 9, wherein the step of obtaining said amino acid compositions which said plurality of thermophilic microorganisms have is conducted after excluding proteins whose amino acid sequence is 50 amino acids or less and after excluding proteins which are predicted to contain two or more transmembrane domains, and
   wherein the step for obtaining said amino acid compositions which said plurality of said non-thermophilic microorganisms have is conducted after excluding proteins whose amino acid sequence is 50 amino acids or less and after excluding proteins which are predicted to contain two or more transmembrane domains.

11. The computer program product of claim 9, wherein the step of obtaining said amino acid compositions which said plurality of thermophilic microorganisms have is conducted after excluding proteins whose amino acid sequence is 50 amino acids or less and after excluding proteins which are predicted to contain two or more transmembrane domains.

12. The computer program product of claim 9, wherein the predetermined range is −0.01 to +0.01.

13. The method of claim 2, further comprising the step of confirming the thermostability of the test protein if the test protein is determined to have thermostability.

14. The method of claim 3, further comprising the step of confirming the thermostability of the test protein if the test protein is determined to have thermostability.

15. The method of claim 4, further comprising the step of confirming the thermostability of the test protein if the test protein is determined to have thermostability.

16. The method of claim 5, further comprising the step of confirming the thermostability of the test protein if the test protein is determined to have thermostability.

17. The method of claim 6, further comprising the step of confirming the thermostability of the test protein if the test protein is determined to have thermostability.

18. The method of claim 7, further comprising the step of confirming the thermostability of the test protein if the test protein is determined to have thermostability.

* * * * *